US009260521B2

(12) United States Patent
Kelm et al.

(10) Patent No.: US 9,260,521 B2
(45) Date of Patent: *Feb. 16, 2016

(54) TREATMENT OF TUMORS USING SPECIFIC ANTI-L1 ANTIBODY

(71) Applicants: Deutsches Krebsforschungszentrum Stiftung des Oeffentlichen Rechts, Heidelberg (DE); Medigene AG, Martinsried (DE)

(72) Inventors: Daniela Kelm, Steinheim an der Murr (DE); Peter Altevogt, Neckargemuend (DE); Gerhard Moldenhauer, Bad Arolsen (DE); Frank Breitling, Heidelberg (DE); Achim Krueger, Munich (DE); Silke Baerreiter, Weinheim (DE); Sandra Luettgau, Schongau (DE); Ulrich Moebius, Gauting (DE); Yi Li, Wantage (GB); Susanne Sebens, Kiel (DE); Heiner Schaefer, Kiel (DE)

(73) Assignees: MEDIGENE AG, Martinsried (DE); DEUTSCHES KREBSFORSCHUNGSZENTRUM STIFUNG DES OFFENTLICHEN RECHTS, Heidelberg (DE)

( * ) Notice: Subject to any disclaimer, the term of this patent is extended or adjusted under 35 U.S.C. 154(b) by 180 days.

This patent is subject to a terminal disclaimer.

(21) Appl. No.: 14/045,019

(22) Filed: Oct. 3, 2013

(65) Prior Publication Data
US 2014/0120117 A1 May 1, 2014

Related U.S. Application Data

(60) Continuation of application No. 13/367,178, filed on Feb. 6, 2012, now Pat. No. 8,580,258, which is a division of application No. 12/139,006, filed on Jun. 13, 2008, now Pat. No. 8,138,313.

(60) Provisional application No. 60/944,359, filed on Jun. 15, 2007.

(51) Int. Cl.
*C07K 16/00* (2006.01)
*C12P 21/08* (2006.01)
*A61K 39/395* (2006.01)
*A61K 39/00* (2006.01)
*C07K 16/28* (2006.01)
*A61K 45/06* (2006.01)
*A61N 5/02* (2006.01)
*A61N 5/06* (2006.01)
*A61N 5/10* (2006.01)
*G01N 33/574* (2006.01)

(52) U.S. Cl.
CPC ....... *C07K 16/2803* (2013.01); *A61K 39/39558* (2013.01); *A61K 45/06* (2013.01); *A61N 5/02* (2013.01); *A61N 5/0613* (2013.01); *A61N 5/10* (2013.01); *G01N 33/57492* (2013.01); *A61K 2039/505* (2013.01); *A61N 2005/0661* (2013.01); *A61N 2005/1087* (2013.01); *A61N 2005/1089* (2013.01); *C07K 2317/24* (2013.01); *C07K 2317/41* (2013.01); *C07K 2317/622* (2013.01); *C07K 2317/73* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 5,223,409 A | 6/1993 | Ladner et al. | |
| 5,225,539 A | 7/1993 | Winter | |
| 5,545,806 A | 8/1996 | Lonberg et al. | |
| 5,545,807 A | 8/1996 | Surani et al. | |
| 5,569,825 A | 10/1996 | Lonberg et al. | |
| 5,585,089 A | 12/1996 | Queen et al. | |
| 5,589,369 A | 12/1996 | Seidman et al. | |
| 5,591,669 A | 1/1997 | Krimpenfort et al. | |
| 5,624,821 A | 4/1997 | Winter et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,859,205 A | 1/1999 | Adair et al. | |
| 6,114,507 A | 9/2000 | Shirakawa et al. | |
| 6,248,516 B1 | 6/2001 | Winter et al. | |
| 6,407,213 B1 | 6/2002 | Carter et al. | |
| 6,455,043 B1 | 9/2002 | Grillo-Lopez | |
| 6,737,056 B1 | 5/2004 | Presta | |
| 6,811,779 B2 | 11/2004 | Rockwell et al. | |

(Continued)

FOREIGN PATENT DOCUMENTS

EP  0 368 684 B1  5/1990
EP  1293514  3/2003

(Continued)

OTHER PUBLICATIONS

Adamis, A. et al., "Angiogenesis and ophthalmic disease," 3 Angiogenesis pp. 9-14 (1999).
Amarzguioui, M., et al., "Hammerhead ribozyme design and application", Cell. Mol. Life Sci., vol. 54, pp. 1175-1202, (1999).
Antibodies—A Laboratory manual, E. Harlow et al., Cold Spring Harbor Laboratory Press, 8 pgs., 1998.
Arlt, A., et al., "Autocrine production of interleukin 1beta confers constitutive nuclear factor kappaB activity and chemoresistance in pancreatic carcinoma cell lines", Cancer Res., vol. 62, pp. 910-916, (2002).

(Continued)

Primary Examiner — Hong Sang
(74) Attorney, Agent, or Firm — The Marbury Law Group, PLLC

(57) ABSTRACT

The present invention relates to the anti-L1 monoclonal antibody 9.3 as well as to related antibodies or binding molecules and well as to the uses thereof, especially in tumor treatment.

20 Claims, 29 Drawing Sheets

(56) References Cited

U.S. PATENT DOCUMENTS

Figure 1:
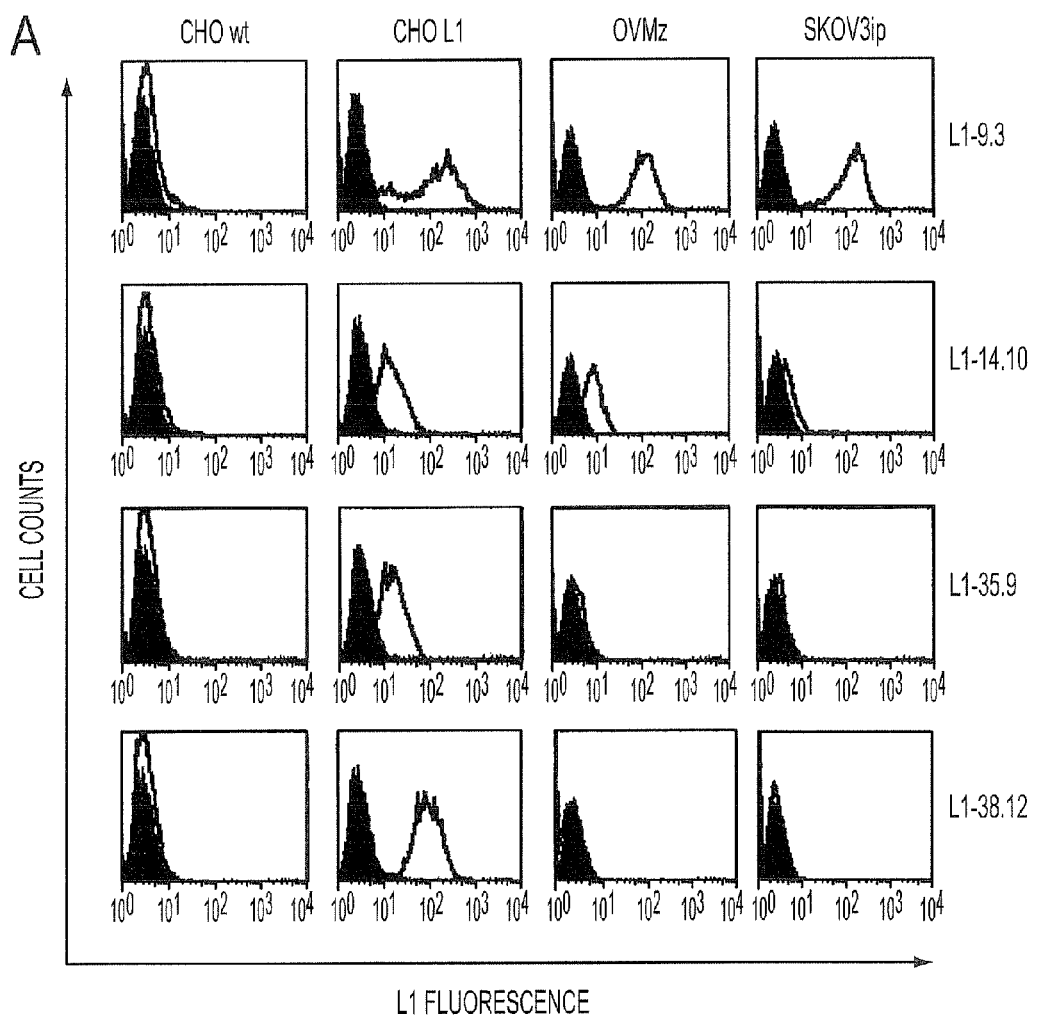
Figure 1:
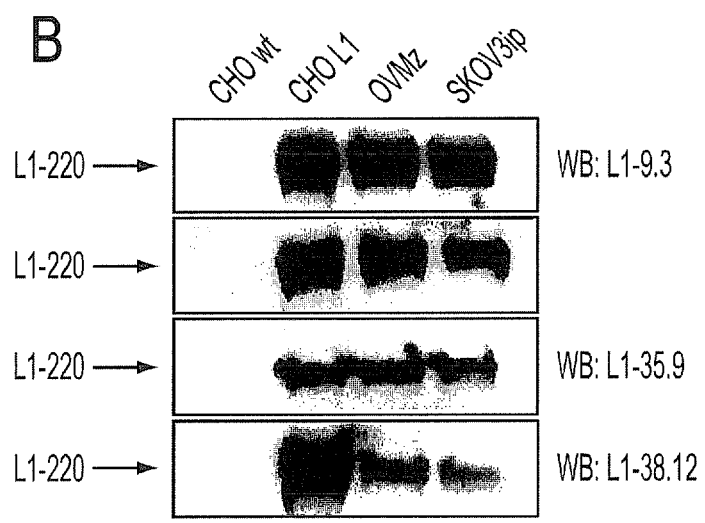

| | | |
|---|---|---|
| 7,670,601 B2 | 3/2010 | Altevogt et al. |
| 2004/0115206 A1 | 6/2004 | Primiano et al. |
| 2004/0259084 A1 | 12/2004 | Altevogt et al. |
| 2005/0074426 A1 | 4/2005 | Corti et al. |
| 2007/0031436 A1 | 2/2007 | Little et al. |

FOREIGN PATENT DOCUMENTS

| | | |
|---|---|---|
| EP | 1 623 995 A1 | 2/2006 |
| EP | 1 172 654 B2 | 10/2007 |
| WO | WO 88/01649 | 3/1988 |
| WO | WO 90/02809 | 3/1990 |
| WO | WO 90/12592 | 11/1990 |
| WO | WO 91/17271 | 11/1991 |
| WO | WO 91/18619 | 12/1991 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 93/06213 | 4/1993 |
| WO | WO 93/11161 | 6/1993 |
| WO | WO 94/04189 | 3/1994 |
| WO | WO 98/24884 | 6/1998 |
| WO | WO 98/40052 | 9/1998 |
| WO | WO 99/57150 | 11/1999 |
| WO | WO 99/58572 | 11/1999 |
| WO | WO 02/04952 A2 | 1/2002 |
| WO | WO 2004/003183 A1 | 1/2004 |
| WO | WO 2004/037198 A2 | 5/2004 |
| WO | WO 2004/067038 A1 | 8/2004 |
| WO | WO 2004/083373 A2 | 9/2004 |
| WO | WO 2006/013051 A1 | 2/2006 |
| WO | WO 2007/030642 A2 | 3/2007 |
| WO | WO 2007/114550 A1 | 10/2007 |
| WO | WO 2008/023946 A1 | 2/2008 |
| WO | WO 2008/046529 A1 | 4/2008 |

OTHER PUBLICATIONS

Allory et al., "The L1 Cell Adhesion Molecule is Induced in Renal Cancer Cells and Correlates with Metastasis in Clear Cell Carcinomas," Clin. Canc. Res., vol. 11, pp. 1190-1197 (2005).
Arlt et al., "Efficient Inhibition of Intra-Peritoneal Tumor Growth and Dissemination of Human Ovarian Carcinoma Cells in Nude Mice by Anti-L1 Cell Adhesion Molecule Monoclonal Antibody Treatment," Cancer Res., 66, pp. 936-943 (2006).
Bird et al., "Single-Chain Antigen-Binding Proteins," Science, 242, pp. 423-426 (1988).
Brennan et al., "Preparation of Bispecific Antibodies by Chemical Recombination of Monoclonal Immunoglobulin $G_1$ Fragments," Science, 229, p. 81 (1985).
Bar-Eli, M., "Gene regulation in melanoma progression by the AP-2 transcription factor", Pigment Cell Res., vol. 14, pp. 78-85 (2001).
Bendig, "Humanization of Rodent Monoclonal Antibodies by CDR Grafting", Methods: A Companion to Methods in Enzymology,; 8:83-93 (1995).
Beste, G., et al., "Small antibody-like proteins with prescribed ligand specificities derived from the lipocalin fold", Proc. Natl. Acad. Sci, USA, vol. 96, pp. 1898-1903, (1999).
Blood, C. et al., "Tumor interactions with the vasculature: angiogenesis and tumor metastasis," 1032 Biochim. Biophys. Acta 89-118 (1990).
Brummendorf, T., et al., "Neural cell recognition molecule L1: from cell biology to human hereditary brain malformations", Curr Opin Neurobiol, vol. 8, pp. 87-97, (1999).
Brunner, G., et al., "Sulfated glycosaminoglycans enhance tumor cell invasion in vitro by stimulating plasminogen activation", Exp Cell Res., vol. 239, pp. 301-310 (1998).
Cannistra, S. A., "Cancer of the Ovary", N. Engl J. Med, vol. 351 pp. 2519-2529 (2004).

Carmeliet, P., "Angiogenesis in life, disease and medicine," 438 Nature 932 (2005).
Carmeliet, P., "Supplemental Information to: Angiogenesis in life, disease and medicine," 438 Nature pp. 932-936 (Suppl. pp. 1-14) (2005).
Castellani, V., et al., "Cis and trans interactions of L1 with neuropilin-1 control axonal responses to semaphoring 3A", Embo J., vol. 21, pp. 6348-6357 (2002).
Chen, S., et al., "Prevention of neuronal cell death by neural adhesion molecules L1 and CHL1", J. Neurobiol, vol. 38, pp. 428-439 (1999).
Cheng, L., et al., "L1-mediated branching is regulated by two ezrin-radixin-moezin (ERM)—binding sites, the RSLE region and a novel juxtamembrane ERM-binding region", J Neurosci., vol. 26, pp. 395-403 (2005).
Cheng, L., et al., "RanBPM is an L1-interacting protein that regulates L1-mediated mitogen-activated protein kinase activation", J Neurochem, vol. 94, pp. 1102-1110 (2005).
Colucci-D'Amato, L., et al., "Chronic activation of ERK and neurodegenerative diseases", Bioessays, vol. 26, pp. 1085-1095 (2003).
Costa, C. et al., "Angiogenesis and chronic inflammation: cause or consequence?" 10 Angiogenesies 149-166 (2007).
Couture, L. A., et al., "Anti-gene therapy: the use of ribozymes to inhibit gene function", Trends Genet, vol. 12, pp. 510-515 (1996).
Carter, "Potent Antibody Therapeutics by Design," Nature Rev. Immunol., 6, pp. 343-357 (2006).
Chase, "Medical Applications of Radioisotopes," Remington's Pharmaceutical Sciences, Chap. 33, 18$^{th}$ Ed., pp. 624-652 (1990).
Clackson et al., "Making Antibody Fragments Using Phage Display Libraries," Nature, 352, pp. 624-628 (1991).
Colman, "Effects of amino acid sequence changes on antibody-antigen interactions", Research in Immunology, 145:33-36, 1994.
Corvalan et al., "Tumor Therapy with Vinca Alkaloids Targeted by a Hybrid-Hybrid Monoclonal Antibody Recognising both CEA and VINCA Alkaloids," Intl. J. Cancer Suppl., 2, p. 22 (1988).
Diamond, B.A., et al., "Monoclonal Antibodies", N. England J. Medicine, pp. 1344-1349 (1981).
Ebeling, O. et al., "L1 adhesion molecule on human lymphocytes and monocytes: expression and involvement in binding to alpha v beta 3 integrin," 26 Eur. J. Immunol. 2508-2516 (1996).
Eichmann, A. et al., "Neural guidance molecules regulate vascular remodeling and vessel navigation," 19 Genes Dev. 1013-1021 (2005).
Elbashir, S.M., et al., "Duplexes of 21-nucleotide RNAs mediate RNA interference in cultured mammalian cell", Nature, vol. 411, p. 494-498 (2001).
Elbashir, S.M., et al., "RNA interference is mediated by 21- and 22-nucleotide RNAs", Genes Dev., vol. 15, p. 188-200 (2001).
Felding-Habermann B. et al., "A single immunoglobulin-like domain of the human neural cell adhesion molecule L1 supports adhesion by multiple vascular and platelet integrins," 139 J Cell Biol. 1567-1581 (1997).
Ferrara N. et al., "Angiogenesis as a therapeutic target," 438 Nature 967-974 (2005).
Fischer, O. M., et al., "Oxidative and osmotic stress signaling in tumor cells is mediated by ADAM proteases and heparin-binding epidermal growth factor", Mol Cell Biol, vol. 24, No. 12, pp. 5172-5183 (2004).
Folkman J., "Angiogenesis in cancer, vascular, rheumatoid and other disease," 1 Nat Med., 27-31 (1995).
Folkman, J. et al., "Angiogenic factors," 235 Science, 442-447 (1987).
Folkman, J. et al., "Induction of angiogenesis during the transition from hyperplasia to neoplasia," 339 Nature 58-61 (1989).
Folkman, J., "The role of angiogenesis in tumor growth," 3 Semin. Cancer Biol. 65-71 (1992).
Fukahi, K., et al., "Aberrant expression of neuropilin-1 and -2 in human pancreatic cancel cells", Clin Cancer Res, vol. 10, pp. 581-590 (2004).
Fogel et al., "L1 Adhesion Molecule (CD 171) in Development and Progression of Human Malignant Melanoma," Cancer Lett., 189, pp. 237-247 (2003).

(56) References Cited

OTHER PUBLICATIONS

Fogel et al., "11 Expression as a Predictor of Progression and Survival in Patients with Uterine and Ovarian Carcinomas," Lancet, 362, pp. 869-875 (2003).
Foote, J. et al.—"Antibody Framework Residues Affecting the Conformation of the Hypervariable Loops", J. Molecular Biology, 1992, vol. 224, pp. 487-499.
Fuchs et al., Targeting Recombinant Antibodies to the Surface of Escherichia coli: Fusion to a Peptidoglycan Associated Lipoprotein, Bio/Technology, 9, pp. 1370-1372 (1991).
Gavert et al., "L1, A Novel Target of Beta-Catenin Signaling, Transforms Cells and is Expressed at the Invasive Front of Colon Cancers," Cell Biol., 168, pp. 633-642 (2005).
Griffiths et al., "Human Anti-Self Antibodies with High Specificity from Phage Display Libraries," The EMBO Journ., 12, pp. 725-734 (1993).
Gast D. et al., "The cytoplasmic part of L1-CAM controls growth and gene expression in human tumors that is reversed by therapeutic antibodies," 27 Oncogene 1281-1289 (2008).
Gast, D., et al., "The cytoplasmic protion of L1-CAM controls gene expression in tumor cells that is reversed by therapeutic L1 antibodies", Oncogene, pp. 1-9 (2007).
Gast, D., et al.,"L1 augments cell migration and tumor growth but not beta3 integrin expression in ovarian carcinomas", Int., J. Cancer, vol. 115, pp. 658-665 (2002).
Gutwein, P., et al., "ADAM10-mediated cleavage of L1 adhesion molecule at the cell surface and in released membrane vesicles", FASEB J, vol. 17, pp. 1-22 (2005).
Gutwein, P., et al., "Cleavage of L1 in exosomes and apoptotic membrane vesicles released from ovarian carcinoma cells", Clin Cancer Res, vol. 11, pp. 2492-2501 (2005).
Gutwein, P., et al., "Role of Src kinases in the ADAM-mediated release of L1 adhesion molecule from human tumor cells", J Biol Chem, vol. 275, pp. 15490-15497 (2000).
Hall, H. et al., "Matrix-bound sixth Ig-like domain of cell adhesion Molecule L1 acts as an angiogenic factor by ligating alphavbeta3-integrin and activating VEGF-R2" 68 Microvacular Research 169-178 (2004).
Huszar, M., et al., "Expression profile analysis in multiple human tumors identifies L1 (CD171) as molecular marker for differential diagnosis and targeted therapy", Human Pathol., vol. 37, pp. 1000-1008 (2006).
Hay et al., "Bacteriophage Cloning and Escherichia coli Expression of a Human IgM Fab," Hum. Antibod. Hybridomas, 3, pp. 81-85 (1992).
Honda et al., "A Human Hybrid Hybridoma Producing a Bispecific Monoclonal Antibody that can Target Tumor Cells for Attack by Pseudomonas aeruginosa Exotoxin A," Cytotechnology, 4, pp. 59-68 (1990).
Hortsch, "Structural and Functional Evolution of the L1 Family: Are Four Adhesion Molecules Better Than One," Mol. Cell Neurosci., 15, pp. 1-10 (2000).
Huse et al., "Generation of a Large Combinatorial Library of the Immunoglobulin Repertoire in Phage Lambda," Science, 246, pp. 1275-1281 (1989).
Huszar et al., "Expression Profile Analysis in Multiple Human Tumors Identifies L1 (CD171) as a Molecular Marker for Differential Diagnosis and Targeted Therapy," Hum. Pathol., 37, pp. 1000-1008 (2006).
Ignelzi, M. A., et al., "Impaired neurite outgrowth of src-minus cerebellar neurons on the cell adhesion molecule LI", Neuron, vol. 12, pp. 873-884 (1994).
Issa, Y. et al. "Enhanced L1CAM expression on pancreatic tumor endothelium mediates selective tumor cell transmigration" 87 J. Mol. Med. 99-112 (2008).
Izumoto, S., et al., "Gene expression of neural cell adhesion molecule L1 in malignant gliomas and biological significance of L1 in glioma invasion", Cancer Res, vol. 56, pp. 1440-1444 (1996).
Kaifi, J. et al., "L1 is associated with micrometastatic spread and poor outcome in colorectal cancer," 20 Mod. Pathol. 1183-1190 (2007).
Kaifi, J. T., et al., "Absence of L1 in Pancreatic Masses Distinguishes Adenocarcinomas from Poorly Differentiated Neuroendocrine Carcinomas", Anticancer Res., vol. 26, pp. 1167-1170 (2006).
Kaifi, J. T., et al., L1 (CD171) is highly expressed in gastrointestinal stromal tumors, Mod Pathol, vol. 19, pp. 399-406 (2006).
Kaifi, J. T., et al., "L1 is a potential marker for poorly-differentiated pancreatic neuroendocrine carcinoma", World J. Gastroenteral, vol. 12, pp. 94-98 (2006).
Kalthoff, H., et al., p53 and K-RAS alterations in pancreatic epithelial cell lesions, Oncogene, vol. 8, pp. 289-298 (1993).
Kamiguchi, H., "The mechanism of axon growth: what we have learned from the cell adhesion molecule L1", Mol. Neurobiol., vol. 28, pp. 219-227 (2003).
Kenwrick, S., et al., "Neural cell recognition molecule L1: relating biological complexity to human disease mutations", Hum.Mol. Genet, vol. 9, pp. 879-886 (2005).
Kim, S., et al, "Current status of the molecular mechanisms of anti-cancer drug-induced apoptosis", cancer, Cancer Chemother. Pharmacol., vol. 50, pp. 343-352 (20002).
Kim, S., et al., "ERK1/2 is an endogenous negative regulator of the y-secretase activity", FASEB J., vol. 20, pp. 1-22 (2005).
Katayama et al., "Expression of Neural Cell Adhesion Molecule L1 in Human Lung Cancer Cell Lines," Cell Struct. Funct., 22, pp. 511-516 (1997).
Knogler, et al., "Copper-67 Radioimmunotherapy and Growth Inhibition by Anti-L1-Cell Adhesion Molecule Monoclonal Antibodies in a Therapy Model of Ovarian Cancer Metastasis", Clinical Cancer Research, American Association for Cancer, clincancerres.aacrjournals.org, pp. 602-611, (2007).
Kurokawa et al., "Enhanced Fibrinolysis by a Bispecific Monoclonal Antibody Reactive to Fibrin and Tissue Plasminogen Activator," Biotechnology, 7, pp. 1163-1167 (1989).
Langer, "New Methods of Drug Delivery," Science, 249, pp. 1527-1533 (1990).
Landman, N., et al., "Got RIP? Presenilin-dependent intramembrane proteolysis in growth factor receptor signaling", Cytokine Growth Factor Rev., vol. 15, pp. 337-351 (2004).
Lockhart, A. C., et al., "Treatment for pancreatic cancer: current therapy and continued progress", Gastroenterology, vol. 128, pp. 1642-1654 (2005).
Loers, G., et al., "Signal transduction pathways implicated in neural recognition molecule L1 triggered neuroprotection and neuritogenesis", J. Neurochem, vol. 92, pp. 1463-1476 (2005).
Lotan, R., "Retinoids in cancer chemoprevention", FASEB J., vol. 10, pp. 1031-1039 (1996).
Manor, D., et al., "Mammary carcinoma suppression by cellular retinoic acid binding protein-II", Cancer Res., vol. 63, pp. 4426-4433 (2003).
Marambaud, P., et al., "A CBP binding transcriptional repressor produced by the PS1/epsilon-cleavage of N-cadherin is inhibited by PS1 FAD mutations", Cell, vol. 114, pp. 635-645 (2003).
Maretzky, T., et al., "L1 is sequentially processed by two differently activated metalloproteases and presenilin/gamma-secretase and regulates neural cell adhesion, cell migration, and neurite outgrowth", Mol. Cell Biol., vol. 25, pp. 9040-9053 (2005).
Matter, et al., A signaling pathway from the alpha5betal and alpha(v)beta3 integrins that elevates bcl-2 transcription, J Biol Chem, vol. 276, pp. 27757-27763 (2001).
Mechtersheimer, S., et al., "Ectodomain shedding of L1 adhesion molecule promotes cell migration by autocrine binding to integrins", J. Cell Biol., vol. 155, pp. 66-673 (2001).
Meier, F., et al., "The adhesion molecule L1 (CD171) promotes melanoma progression", Int. J. Cancer, vol. 119, pp. 549-555 (2006).
Miyamoto, H., et al., "Tumor-stroma interaction of human pancreatic cancer: acquired resistance to anticancer drugs and proliferation regulation is dependent on extracellular matrix proteins", Pancreas, vol. 28, pp. 38-44 (2004).
Moldenhauer, G., et al., "Epithelium-specific surface glycoprotein of Mr 34,000 is a widely distributed human carcinoma marker", Br. J. Cancer, vol. 56, pp. 714-721 (1987).
Morrison, D. K., et al., "Regulation of MAP kinase signaling modules by scaffold proteins in mammals", Annu. Rev. Cell Dev. Biol., vol. 19, pp. 91-118 (2003).

(56) References Cited

OTHER PUBLICATIONS

Müerköster, S., et al., "Acquired chemoresistance in pancreatic carcinoma cells: induced secretion of IL-1beta and NO lead to inactivation of caspases", Oncogene, vol. 25, pp. 3973-3981 (2006).
Müerköster, S., et al., "Drug-induced expression of the cellular adhesion molecule L1CAM confers anti-apoptotic protectin and chemoresistance in pancreatic ductal adenocarcinoma cells", Oncogene, vol. 26 (19), pp. 2759-2768 (2007).
Mujoo, K. et al., "Characterization of a unique glycoprotein antigen expressed on the surface of a human neuroblastoma cells," 261 J. Biol. Chem. 10299-10305 (1986).
Meli et al., "Anti-neuroblastoma Antibody chCE7 Binds to an Isoform of L1-CAM Present in Renal Carcinoma Cells," Int. J. Cancer, 83, pp. 401-408 (1999).
Moos et al., "Neural Adhesion Molecule L1 as a Member of the Immunoglobulin Superfamily with Binding Domains Similar to Fibronectin," Nature, 334, pp. 701-703 (1988).
Neufeld, G. et al., "The neuropilins: multifunctional semaphorin and VEGF receptors that modulate axon guidance and angiogenesis," 12 Trends Cardiovasc. Med. 13-19 (2002).
Nicoletti, I., et al., "A rapid and simple method for measuring thymocyte apoptosis by propidium iodide staining and flow cytometry", J Immunol Methods, vol. 139, pp. 271-279. (1991).
Nishimune, H., et al., "Neural adhesion molecules Li and CHL1 are survival factors for motoneurons", J Neurosci Res, vol. 80, pp. 593-599 (2005).
Nitecki, S. et al., "Long-term survival after resection for ductal adenocarcinoma of the pancreas. Is it really improving?" 221 Ann. Surg. 59-66 (1995).
Novak-Hofer, I. et al., "Antibodies directed against L1-CAM synergize with Genistein in inhibiting growth and survival pathways in SKOV3ip human ovarian cancer cells," 261 Cancer Lett. 193-204 (2008).
Nummer, D. et al, "Role of tumor endothelium in CD4+ CD25+ regulatory T cell infiltration of human pancreatic carcinoma," 99 J. Nat'l Cancer Inst. 1188-1199 (2007).
Oleszewski et al., "Characterization of the L1-Neurocan Binding Site, Implications for L1-L1 Homophilic Binding," J. Biol. Chem., 275, pp. 34478-34485 (2000).
Orlandi et al., "Cloning Immunoglobulin Variable Domains for Expression by the Polymerase Chain Reaction," Proc. Natl. Acad. Sci. USA, 86, pp. 3833-3837 (1989).
Pastan et al., "Immunotoxin Treatment of Cancer," Annu. Rev. Med., 58, pp. 221-237 (2007).
Patel et al., "The 200/220 kDa Antigen Recognized by Monoclonal Antibody (MAb) UJ127.11 on Neural Tissues and Tumors is the Human L1 Adhesion Molecule," Hybridoma, 10, pp. 481-491 (1991).
Paul, Fundamental Immunology, 31rd Edition, 292-295 (1993).
Pimm et al., "A Bispecific Monoclonal Antibody Against Methotrexate and a Human Tumour Associated Antigen Augments Cytotoxicity of Methotrexate-Carrier Conjugate," British J. Of Cancer, 61, pp. 508-513 (1990).
Patel, K. et al., "X-linked gene MIC5 codes for the L1 adhesion molecule recognized by monoclonal antibody R1," 60 Cancer Genet. Cytogenet. 20-22 (1992).
Perez-Atayde, A. et al., "Spectrum of tumor angiogenesis in the bone marrow of children with acute lymphoblastic leukemia," 150 Am. J. Pathol. 815-821 (1997).
Persidis, A., "Ribozyme therapeutics", Nat. Biotechnol., vol. 15, pp. 921-922 (1997).
Primiano, T., et al., "Identification of potential anticancer drug targets through the selection of growth-inhibitory genetic suppressor elements", Cancer Cell, vol. 4, pp. 41-53 (2003).
Remmington'S Pharmaceutical Sciences, 5$^{th}$ Ed., Chapter 33, In Particular pp. 624-652, (1990).
Raso et al., "Hybrid Antibodies with Dual Specificity for the Delivery of Ricin to Immunoglobulin-Bearing Target Cells[1]," Cancer Res., 41, pp. 2073-2078 (1981).
Rudikoff et al., "Single amino acid substitution altering antigen-binding specificity", Proc. Natl. Acad. Sci. USA, 79(6):1979-1983, Mar. 1982.
Schachner, "Recognition Molecules and Synaptic Plasticity," Curr. Opin. Cell Biol., 9, pp. 627-634 (1997).
Segal et al., " Bispecific Antibodies in Cancer Therapy," Current Opin. Immunol., 11, pp. 558-562 (1999).
Senner et al., "L1 Expressed by Glioma Cells Promotes Adhesion but not Migration," Glia, 38, pp. 146-154 (2002).
Songsivilai et al., "Bispecific Antibody: A Tool for Diagnosis and Treatment of Disease," Clin. Exp. Immunol., 79, pp. 315-321 (1990).
Schaefer, A. W., et al., "Activation of the MAPK signal cascade by the neural cell adhesion molecule L1 requires L1 internalization", J Biol Chem, vol. 274, pp. 37965-37973 (1999).
Schaeffer, H. J., et al., "Mitogen-activated protein kinases: specific messages from ubiquitous messengers", Mol. Cell Biol., vol. 19, pp. 2435-2444 (1999).
Schafer, H., et al, "The putative apoptosis inhibitor IEX-1L is a mutant nonspliced variant of p22(PRG1/IEX-1) and is not expressed in vivo", Biochem Biophys Res Commun, vol. 262, pp. 139-145 (1999).
Schmid, R., et al., "A MAP kinase-signaling pathway mediates neurite outgrowth on L1 and requires Src-dependent endocytosis", J. Neurosci, vol. 20, pp. 4177-4188 (2000).
Schmidt-Zachmann, M. S., et al., "Molecular characterization of a novel, widespread nuclear protein that colocalizes with spliceosome components", Mol. Biol. Cell, vol. 9, pp. 143-160 (1998).
Schneider, G., et al., "Pancreatic cancer: basic and clinical aspects", Gastroenterology, vol. 128, pp. 1606-1625 (2005).
Sebens Muerkoster, S. et al, "Drug-induced expression of the cellular adhesion molecule L1CAM confers anti-apoptotic protection and chemoresistance in pancreatic ductal adenocarcinoma cells," 26 Oncogene. 2759 (2007).
Silletti, S., et al., "Extracellular signal-regulated kinase (ERK)-dependent gene expression contributes to L1 cell adhesion molecule-dependent motility and invasion", J Biol Chem, vol. 279, pp. 28880-28888 (2004).
Skerra, A., "Engineered protein scaffolds for molecular recognition", Mol. Recognit., vol. 13, pp. 167-187, (2000).
Skerra, A., "Lipocalins as a scaffold", Biochim. Biophys. Acta, vol. 1482, pp. 337-350 (2000).
St. Croix, B., et al., "Cell adhesion and drug resistance in cancer", Curr Opin Oncol, vol. 9, pp. 549-556, (1997).
Stoeck, A., et al., "A role for exosomes in the constitutive and stimulus-induced ectodomain cleavage of L1 and CD44", Biochem J., vol. 393, pp. 609-618 (2006).
Stoeck, A., et al., "L1-CAM in a membrane-bonund or soluble form augments protectin from apoptosis in ovarian carcinoma cells", Gyn. Oncol., vol. 104, pp. 461-469 (2007).
Tang, N., et al., "Ethanol inhibits L1 cell adhesion molecule activation of mitogen-activated protein kinases", J. Neurochem., vol. 96, pp. 1480-1490 (2006).
Thelen, K., et al., "The neural cell adhesion molecule L1 potentiates integrin-dependent cell migration to extracellular matrix proteins", J Neurosci, vol. 22, pp. 4918-4931 (2002).
Thies et al., "Overexpression of the Cell Adhesion Molecule L1 is Associated with Metastasis in Cutaneous Malignant Melanoma," Eur. J. Cancer, 38, pp. 1708-1716 (2002),.
Van Spriel et al., "Immunotherapeutic Perspective for Bispecific Antibodies," Immunology Today, 21, pp. 391-397 (2000).
Vaish, N. et al., "Recent developments in the hammerhead ribozyme field," 26, Nucleic Acids Res. 5237-5242 (1998).
Vergote, I., et al., "Neoadjuvant chemotherapy for ovarian cancer", Oncology, vol. 19, No. 12, pp. 1615-1622 (2005).
Villedieu, M., et al., "Acquisition of chemoresistance following discontinuous exposures to cisplatin is associated in ovarian carcinoma cells with progressive alteration of FAK, ERK and p38 activation in response to treatment", Gynecol Oncol, vol. 101, pp. 507-519 (2006).
Voura, E. et al., "Involvement of integrin alpha(v)beta(3) and cell adhesion molecule L1 in transendothelial migration of melano ma cells," 12, Mol. Biol. Cell. 2699-2710 (2001).
Winter et al., "Man-Made Antibodies," Nature, 349, pp. 293-299 (1991).

(56) References Cited

OTHER PUBLICATIONS

Winter, G. et al. "Humanized antibodies", antibody-based therapy, Immunology Today, 1993, vol. 14, No. 6, pp. 243-246.

Wolff et al., "A Human Brain Glycoprotein Related to the Mouse Cell Adhesion Molecule L1," *J. Biol. Chem.*, 363, pp. 11943-11947 (1988).

Wu et al., "Receptor-Mediated in Vitro Gene Transformation by a Soluble DNA Carrier System," *J. Biol. Chem.*, 262, pp. 4429-4432 (1987).

Wu et al., "Arming Antibodies: Prospects and Challenges for Immunoconjugates," *Nature Biotechnol.*, 23, pp. 1137-1146 (2005).

Wey, J. S., et al., "Overexpression of neuropilin-1 promotes constitutive MAPK signaling and chemoresistance in pancreatic cancer cells", Br. J. Cancer, vol. 93, pp. 233-241 (2005).

Zhang, et al., "Glucocorticoid-mediated inhibition of chemotherapy in ovarian carcinomas", Int J Oncol, vol. 28, pp. 551-558 (2006).

International Search Report cited in related International Patent Application No. PCT/EP2008/004773, completed Oct. 29, 2008.

Haspel et al., "Critical and Optimal Ig Domains for Promotion of Neurite Outgrowth by L1/Ng-CAM", *J. Neurobiol*; p. 287-302 (2000).

Figure 2
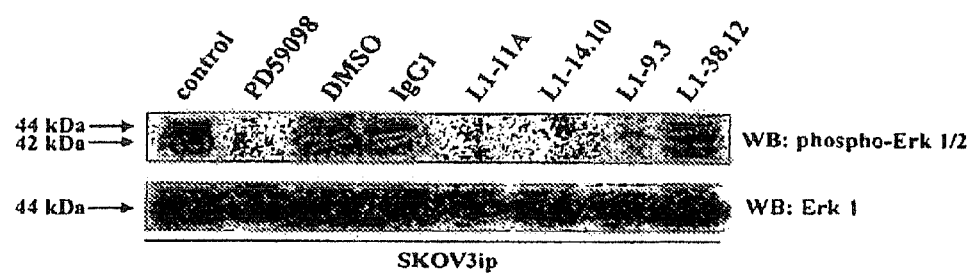
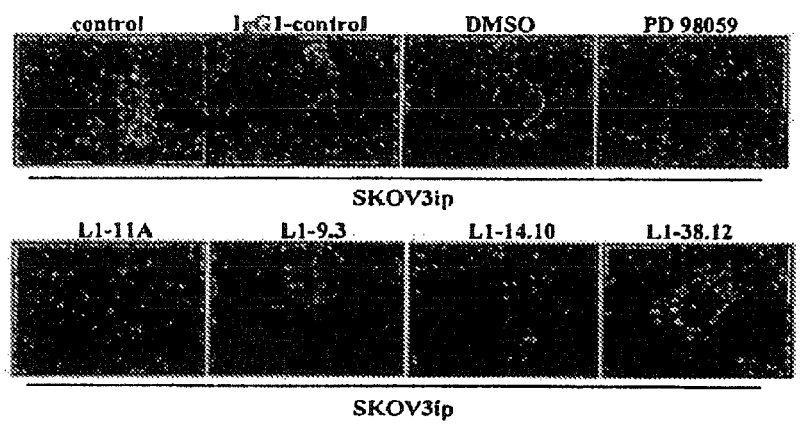

Figure 4:
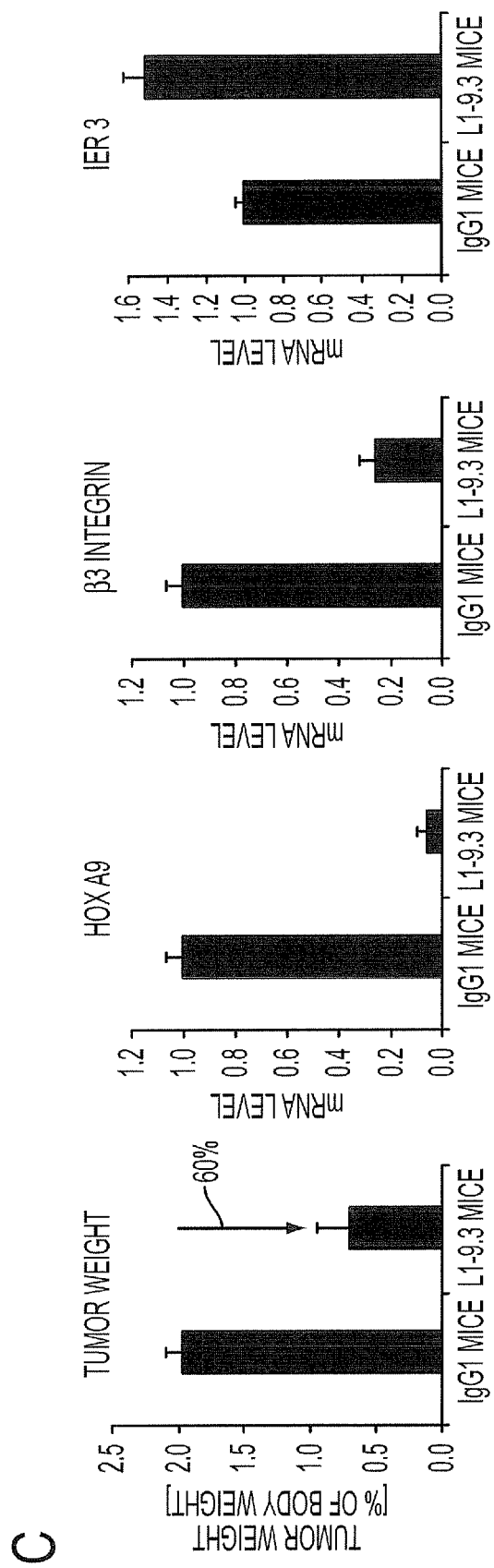

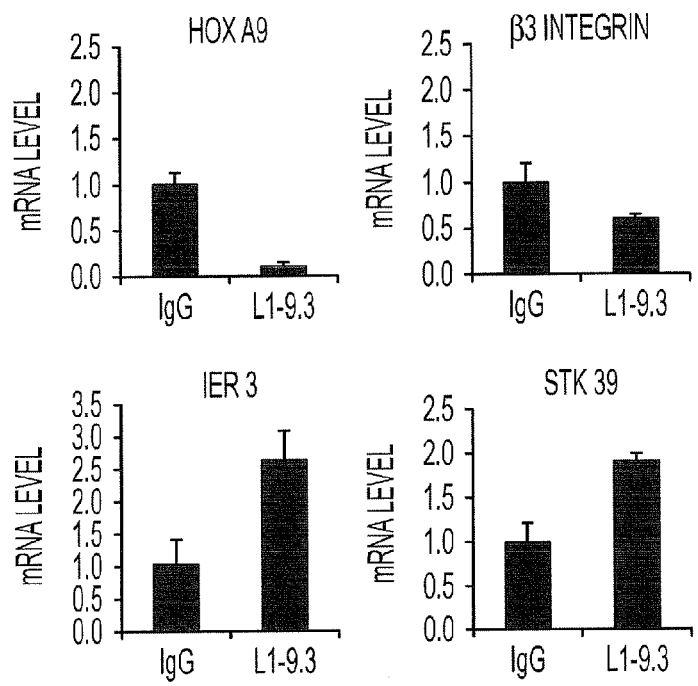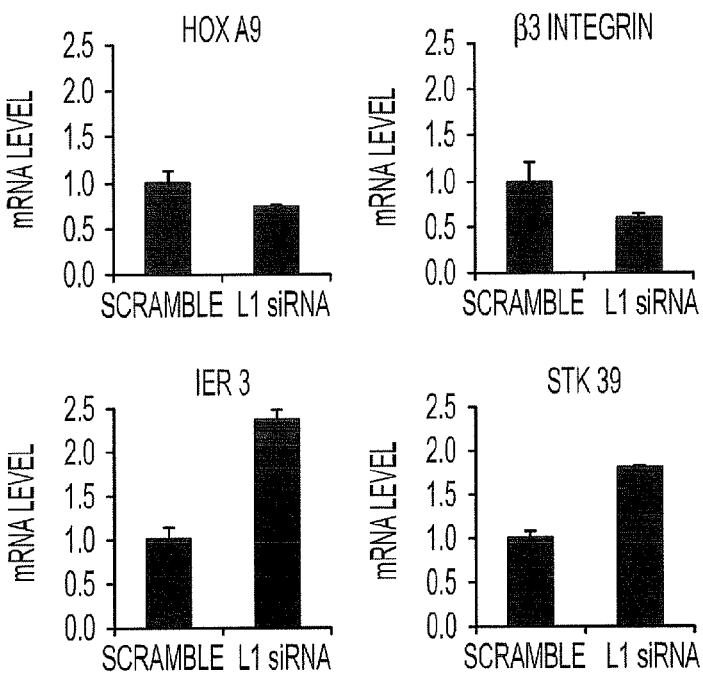
FIG. 4

Figure 6
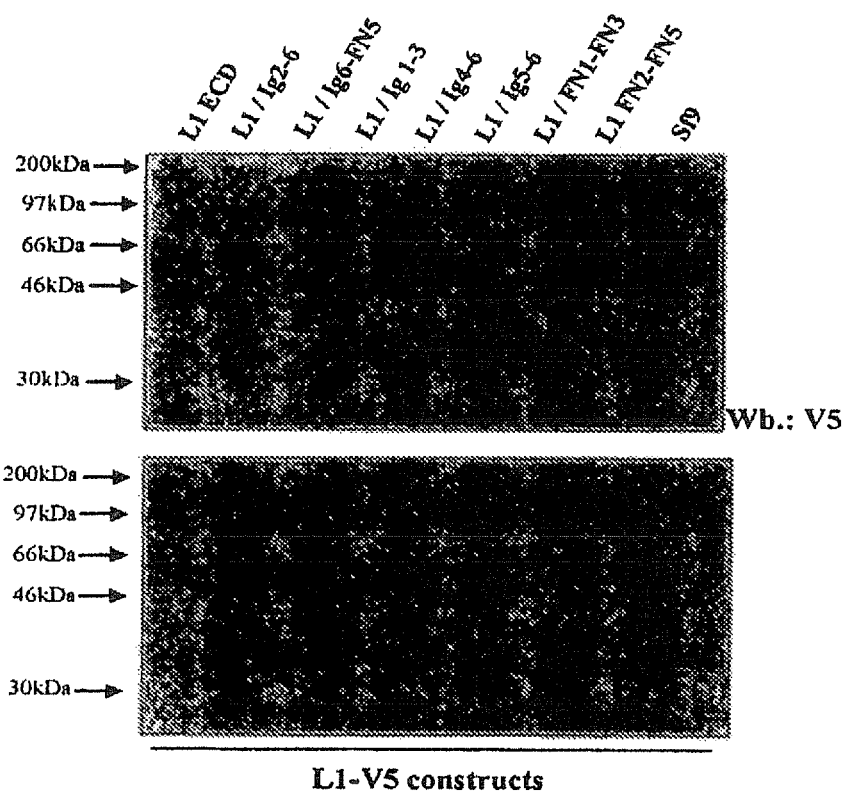
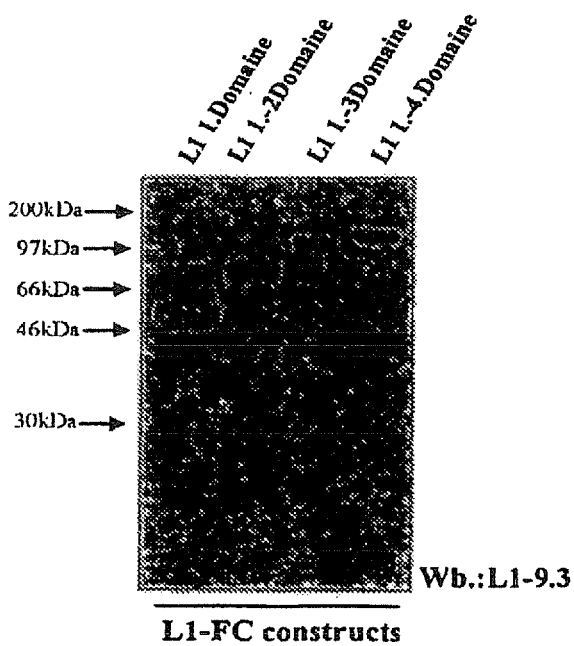

Figure 7
A
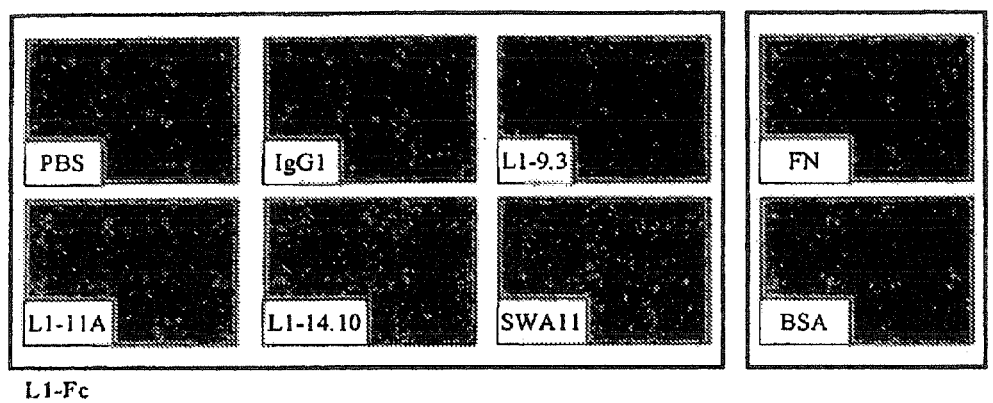
L1-Fc
B

FIG. 8 a) ANTIBODY LIGHT CHAIN AMINO ACID SEQUENCES

| NAME | 1<br>1234567890 | 2<br>1234567890 | 3<br>4567ABCDEF8901234 | CDR1 | 4<br>5678901234567890 | 5<br>0123456 | CDR2 | 6<br>7890123456789012345678 | 7 | 8 | 9<br>9012345ABCDEF67 | CDR3 | 10<br>8901234567890 | 1<br>1 |
|---|---|---|---|---|---|---|---|---|---|---|---|---|---|---|
| L1_9.3 | DIQMTQTTSSLSAFLGDRVTISC | | RASQ | DISNYLN | WYQQKPDGTVKLLIY | YTSRLHS | | GVPSRFSGSGSGTDYSLTISNLEQEDFATYFC | | | QQGNTLP | | FGGGTKLEIKR | |
| humkl | DIQMTQSPSSLSASVGDRVTITC | | RASQSV | DISSYLN | WYQQTPGKAPKLLIY | AASSLES | | GVPSRFSGSGSGTDFTLTISSLQPEDFATYYC | | | QQVNSLP | YT | FGQGTKVEIK | |
| REI | DIQMTQSPSSLSASVGDRVTITC | | QASQ | DIIKYLN | WYQQTPGKAPKLLIY | EASNLQA | | GVPSRFSGSGSGTDYTFTISSLQPEDIATYC | | | QQYQSLP | YT | FGQGTKLQITR | |
| L1_9.3hu | DIQMTQSPSSLSASVGDRVTITC | | RASQ | DISNYLN | WYQQKPGKAPKLLIY | YTSRLHS | | GVPSRFSGSGSGTDYTFTISSLQPEDFATYFC | | | QQGNTLP | WT | FGGGTKLEIKR | |
| L1_9.3hu3 | DIQMTQSPSSLSASVGDRVTITC | | RASQ | DISNYLN | WYQQKPGKAPKLLIY | YTSRLHS | | GVPSRFSGSGSGTDYTLTISSLQPEDFATYFC | | | QQGNTLP | WT | FGGGTKLEIKR | | b) ANTIBODY HEAVY CHAIN AMINO ACID SEQUENCES

| NAME | 1<br>1234567890 | 2<br>1234567890 | 3<br>1234567890 | CDR1<br>12345AB | 4<br>6789012345678 | 5<br>012ABC345678901234 | CDR2<br>5 | 6<br>6789012345 | 7<br>6789012345678901234 | 8<br>5ABC3456789012ABC | 9<br>3456789012345678 | CDR3<br>567890ABCDEFGHIJK12 | 10<br>1 | 3456789012<br>3 |
|---|---|---|---|---|---|---|---|---|---|---|---|---|---|---|
| L1_9.3 | QVQLQQPGAELVKSGASVNLSCRASGYTFT | | RYWML | WVQQRPGHGLEWIG | EINP | RNDRTNYNEKFKT | | KATLTVDRSSSTAYMQLTSLTSEDSAVYFCAL | | | GGGYAM | DY | WGQGTSVTVSS | |
| HumIII | EVQLVESGGGLVQPGGSLRLSCAASGFTFS | | KDYAMSI | WVRQAPGKGLEWVA | VIS | NGSDTYYADSVKG | | RFTISRDDSKNTLYLQMNSLRAEDTAVYYCAR | | | DSRFFD | VI | WGQGTLVTVSS | |
| L1_9.3hu | EVQLVQSGGGLVQSGGSLRLSCRASGYTFT | | RYWML | WVRQPGKGLEWVA | EINP | RNDRTNYNEKFKT | | RFTISVDRSKSTAYLQMDSLRAEDTAVYFCAL | | | GGGYAM | DY | WGQGTLVTVSS | |
| L1_9.3hu3 | EVQLVQSGGGLVQSGGSLRLSCRASGYTFT | | RYWML | WVRQPGKGLEWVA | EINP | RNDRTNYNEKFKT | | RFTISVDRSKNTLYLQMDSLRAEDTAVYFCAL | | | GGGYAM | DY | WGQGTLVTVSS | |

Figure 9 a)

L1_9.3 scFv
DIQMTQTTSSLSAFLGDRVTISCRASQDISNYLNWYQQKPDGTVKLLIYYTSRLHSGVPSRFSGSGSGTDYSLTI
SNLEQEDFATYFCQQGNTLPWTFGGGTKLEIKRTSGPGDGGKGGPGKGPGGEGTKGTGPGGQVQLQQPGAELVKS
GASVNLSCRASGYTFTRYWMLWVRQRPGHGLEWVGEINPRNDRTNYNEKFKTKATLTVDRSSSTAYMQLTSLTSE
DSAVYFCALGGGYAMDYWGQGTSVTVSS b)

L1_9.3Hu
DIQMTQSPSSLSASVGDRVTITCRASQDISNYLNWYQQKPGKAPKLLIYYTSRLHSGVPSRFSGSGSGTDYTLTI
SSLQPEDFATYFCQQGNTLPWTFGGGTKLEIKRTSGPGDGGKGGPGKGPGGEGTKGTGPGGEVQLVQSGGGLVQS
GGSLRLSCRASGYTFTRYWMLWVRQRPGHGLEWVGEINPRNDRTNYNEKFKTRFTISVDRSKSTAYLQMDSLRAD
DTAVYFCALGGGYAMDYWGQGTLVTVSS c)

L1_9.3Hu3
DIQMTQSPSSLSASVGDRVTITCRASQDISNYLNWYQQKPGKAPKLLIYYTSRLHSGVPSRFSGSGSGTDYTLTI
SSLQPEDFATYFCQQGNTLPWTFGGGTKLEIKRTSGPGDGGKGGPGKGPGGEGTKGTGPGGEVQLVQSGGGLVQS
GGSLRLSCRASGYTFTRYWMLWVRQRPGKGLEWVAEINPRNDRTNYNEKFKTRFTISVDRSKNTLYLQMDSLRAE
DTAVYFCALGGGYAMDYWGQGTLVTVSS

Figure 10 a)

L1-9.3 murine single chain antibody
```
             NdeI
             M   K   Y   L   L   P   T   A   A   A   G   L   L   L   L   A ·
  1   ACATATGAAA TACCTATTGC CTACGGCAGC CGCTGGATTG TTATTACTCG
      TGTATACTTT ATGGATAACG GATGCCGTCG GCGACCTAAC AATAATGAGC
                SfiI
                        NcoI
      · A   Q   P   A   M   A   D   I   Q   M   T   Q   T   T   S   S
 51   CGGCCCAGCC GGCCATGGCC GATATTCAGA TGACCCAGAC CACGAGCAGC
      GCCGGGTCGG CCGGTACCGG CTATAAGTCT ACTGGGTCTG GTGCTCGTCG
         L   S   A   F   L   G   D   R   V   T   I   S   C   R   A   S   Q
101   CTGAGCGCGT TTCTGGGCGA TCGTGTGACC ATTAGCTGCC GTGCGAGCCA
      GACTCGCGCA AAGACCCGCT AGCACACTGG TAATCGACGG CACGCTCGGT
      · D   I   S   N   Y   L   N   W   Y   Q   Q   K   P   D   G   T   V ·
151   GGATATTAGC AACTATCTGA ACTGGTATCA GCAGAAACCG GATGGCACCG
      CCTATAATCG TTGATAGACT TGACCATAGT CGTCTTTGGC CTACCGTGGC
      ·  K   L   L   I   Y   Y   T   S   R   L   H   S   G   V   P   S
201   TGAAACTGCT GATTTATTAT ACCAGCCGTC TGCATAGCGG TGTGCCGAGC
      ACTTTGACGA CTAAATAATA TGGTCGGCAG ACGTATCGCC ACACGGCTCG
         R   F   S   G   S   G   S   G   T   D   Y   S   L   T   I   S   N ·
251   CGTTTTAGCG GCAGCGGTAG CGGCACCGAT TATAGCCTGA CCATTTCTAA
      GCAAAATCGC CGTCGCCATC GCCGTGGCTA ATATCGGACT GGTAAAGATT
      · L   E   Q   E   D   F   A   T   Y   F   C   Q   Q   G   N   T   L ·
301   CCTGGAACAG GAAGATTTTG CGACCTATTT TTGCCAGCAG GGCAACACGC
      GGACCTTGTC CTTCTAAAAC GCTGGATAAA AACGGTCGTC CCGTTGTGCG
      ·  P   W   T   F   G   G   G   T   K   L   E   I   K   R   T   S
351   TGCCGTGGAC CTTTGGCGGT GGCACCAAAC TGGAAATTAA ACGTACTAGT
      ACGGCACCTG GAAACCGCCA CCGTGGTTTG ACCTTTAATT TGCATGATCA
       · G   P   G   D   G   G   K   G   G   P   G   K   G   P   G   G   E ·
401   GGTCCGGGCG ATGGCGGTAA AGGCGGTCCG GGCAAAGGTC CGGGTGGCGA
      CCAGGCCCGC TACCGCCATT TCCGCCAGGC CCGTTTCCAG GCCCACCGCT
                                  SmaI
                                  XmaI
                                  AvaI          PstI
      · G   T   K   G   T   G   P   G   G   Q   V   Q   L   Q   Q   P   G ·
451   AGGCACCAAA GGCACTGGGC CCGGGGGTCA GGTTCAGCTG CAGCAGCCGG
      TCCGTGGTTT CCGTGACCCG GGCCCCCAGT CCAAGTCGAC GTCGTCGGCC
      ·  A   E   L   V   K   S   G   A   S   V   N   L   S   C   R   A
501   GTGCGGAACT GGTGAAAAGC GGCGCGAGCG TGAACCTGAG CTGTCGTGCG
      CACGCCTTGA CCACTTTTCG CCGCGCTCGC ACTTGGACTC GACAGCACGC
         S   G   Y   T   F   T   R   Y   W   M   L   W   V   R   Q   R   P ·
551   AGCGGCTATA CCTTTACCCG TTATTGGATG CTGTGGGTGC GTCAGCGTCC
      TCGCCGATAT GGAAATGGGC AATAACCTAC GACACCCACG CAGTCGCAGG
      · G   H   G   L   E   W   V   G   E   I   N   P   R   N   D   R   T ·
601   GGGCCACGGC CTGGAATGGG TGGGCGAAAT TAATCCGCGT AACGATCGTA
      CCCGGTGCCG GACCTTACCC ACCCGCTTTA ATTAGGCGCA TTGCTAGCAT
      ·  N   Y   N   E   K   F   K   T   K   A   T   L   T   V   D   R
651   CCAACTATAA CGAAAAATTC AAAACCAAAG CGACCCTGAC CGTGGATCGT
      GGTTGATATT GCTTTTTAAG TTTTGGTTTC GCTGGGACTG GCACCTAGCA
         S   S   S   T   A   Y   M   Q   L   T   S   L   T   S   E   D   S ·
701   AGCAGCAGCA CCGCGTATAT GCAGCTGACG AGCCTGACCT CTGAAGATAG
      TCGTCGTCGT GGCGCATATA CGTCGACTGC TCGGACTGGA GACTTCTATC
                BssHII
      · A   V   Y   F   C   A   L   G   G   G   Y   A   M   D   Y   W   G ·
751   CGCGGTGTAT TTCTGCGCGC TGGGCGGTGG CTATGCGATG GATTATTGGG
      GCGCCACATA AAGACGCGCG ACCCGCCACC GATACGCTAC CTAATAACCC
                                                            NotI
      · Q   G   T   S   V   T   V   S   S   G   A   A   A   P
801   GCCAGGGCAC CAGCGTTACC GTGAGCAGCG GCGGTGCGGC CGCTGCACCA
      CGGTCCCGTG GTCGCAATGG CACTCGTCGC CGCCACGCCG GCGACGTGGT
         S   V   F   I   F   P   P   S   D   E   Q   L   K   S   G   T   A ·
851   TCTGTCTTCA TCTTCCCGCC ATCTGATGAG CAGTTGAAAT CTGGAACTGC
      AGACAGAAGT AGAAGGGCGG TAGACTACTC GTCAACTTTA GACCTTGACG
      · S   V   V   C   L   L   N   N   F   Y   P   R   E   A   K   V   Q ·
901   CTCTGTTGTG TGCCTGCTGA ATAACTTCTA TCCCAGAGAG GCCAAAGTAC
      GAGACAACAC ACGGACGACT TATTGAAGAT AGGGTCTCTC CGGTTTCATG
      ·  W   K   V   D   N   A   L   Q   S   G   N   S   Q   E   S   V
```

Figure 10 a) cont.

```
 951  AGTGGAAGGT GGATAACGCC CTCCAATCGG GTAACTCCCA GGAGAGTGTC
      TCACCTTCCA CCTATTGCGG GAGGTTAGCC CATTGAGGGT CCTCTCACAG

T   E   Q   D    S   K   D    S   T   Y    S   L   S   S    T   L   T ·
1001  ACAGAGCAGG ACAGCAAGGA CAGCACCTAC AGCCTCAGCA GCACCCTGAC
      TGTCTCGTCC TGTCGTTCCT GTCGTGGATG TCGGAGTCGT CGTGGGACTG
         · L   S   K    A   D   Y   E    K   H   K    V   Y   A    C   E   V   T ·
1051  GCTGAGCAAA GCAGACTACG AGAAACACAA AGTCTACGCC TGCGAAGTCA
      CGACTCGTTT CGTCTGATGC TCTTTGTGTT TCAGATGCGG ACGCTTCAGT
         · H   Q   G    L   S   S    P   V   T   K    S   F   N    R   G   E
1101  CCCATCAGGG CCTGAGTTCG CCCGTCACAA AGAGCTTCAA CCGCGGAGAG
      GGGTAGTCCC GGACTCAAGC GGGCAGTGTT TCTCGAAGTT GGCGCCTCTC
           S   H   H   H    H   H   H    *   *
1151  TCACACCACC ACCACCACCA CTAGTAAT
      AGTGTGGTGG TGGTGGTGGT GATCATTA
```

Figure 10 b)

L1-9.3Hu humanized single chain antibody

```
          NdeI
           M  K   Y  L  L  P   T  A  A   A  G  L   L  L  L  A ·
  1  ACATATGAAA TACCTATTGC CTACGGCAGC CGCTGGATTG TTATTACTCG
     TGTATACTTT ATGGATAACG GATGCCGTCG GCGACCTAAC AATAATGAGC
          SfiI

NcoI                            AvaI
     ·  A  Q  P   A  M  A   D  I  Q  M   T  Q  S   P  S  S
 51  CGGCCCAGCC GGCCATGGCC GATATTCAGA TGACCCAGAG CCCGAGCAGC
     GCCGGGTCGG CCGGTACCGG CTATAAGTCT ACTGGGTCTC GGGCTCGTCG
        L  S  A  S   V  G  D   R  V  T   I  T  C   R  A  S  Q ·
101  CTGAGCGCGA GCGTGGGTGA TCGTGTGACC ATTACCTGCC GTGCGAGCCA
     GACTCGCGCT CGCACCCACT AGCACACTGG TAATGGACGG CACGCTCGGT
     ·  D  I  S   N  Y  L  N   W  Y  Q   Q  K  P   G  K  A  P ·
151  GGATATTAGC AACTATCTGA ACTGGTATCA GCAGAAACCG GGCAAAGCGC
     CCTATAATCG TTGATAGACT TGACCATAGT CGTCTTTGGC CCGTTTCGCG
     ·  K  L  L   I  Y  Y   T  S  R  L   H  S  G   V  P  S
201  CGAAACTGCT GATTTATTAT ACCAGCCGTC TGCATAGCGG TGTGCCGAGC
     GCTTTGACGA CTAAATAATA TGGTCGGCAG ACGTATCGCC ACACGGCTCG
        R  F  S  G   S  G  S   G  T  D   Y  T  F  T   I  S  S ·
251  CGTTTTAGCG GCAGCGGTAG CGGCACCGAT TATACCTTTA CCATTAGCAG
     GCAAAATCGC CGTCGCCATC GCCGTGGCTA ATATGGAAAT GGTAATCGTC
                Pst I
     ·  L  Q  P   E  D  F   A  T  Y  F   C  Q  Q   G  N  T  L ·
301  CCTGCAGCCG GAAGATTTTG CGACCTATTT TTGCCAGCAG GGCAACACGC
     GGACGTCGGC CTTCTAAAAC GCTGGATAAA AACGGTCGTC CCGTTGTGCG
     ·  P  W  T   F  G  G   G  T  K  L   E  I  K   R  T  S
351  TGCCGTGGAC CTTTGGCGGT GGCACCAAAC TGGAAATTAA ACGTACTAGT
     ACGGCACCTG GAAACCGCCA CCGTGGTTTG ACCTTTAATT TGCATGATCA
        G  P  G  D   G  G  K   G  G  P   G  K  G  P   G  G  E ·
401  GGTCCGGGCG ATGGCGGTAA AGGCGGTCCG GGCAAAGGTC CGGGTGGCGA
     CCAGGCCCGC TACCGCCATT TCCGCCAGGC CCGTTTCCAG GCCCACCGCT
                SmaI
                XmaI
                AvaI
     ·  G  T  K   G  T  G  P   G  G  E   V  Q  L   V  Q  S  G ·
451  AGGCACCAAA GGCACTGGGC CCGGGGGTGA AGTTCAGCTG GTGCAGAGCG
     TCCGTGGTTT CCGTGACCCG GGCCCCCACT TCAAGTCGAC CACGTCTCGC
     ·  G  G  L   V  Q  S   G  G  S  L   R  L  S   C  R  A
501  GCGGTGGTCT GGTTCAGAGC GGTGGCAGCC TGCGTCTGAG CTGTCGTGCG
     CGCCACCAGA CCAAGTCTCG CCACCGTCGG ACGCAGACTC GACAGCACGC
        S  G  Y  T   F  T  R   Y  W  M   L  W  V  R   Q  R  P ·
551  AGCGGCTATA CCTTCACCCG TTATTGGATG CTGTGGGTGC GTCAGCGTCC
     TCGCCGATAT GGAAGTGGGC AATAACCTAC GACACCCACG CAGTCGCAGG
     ·  G  H  G   L  E  W  V   G  E  I   N  P  R   N  D  R  T ·
601  GGGCCACGGC CTGGAATGGG TGGGCGAAAT TAATCCGCGT AACGATCGTA
     CCCGGTGCCG GACCTTACCC ACCCGCTTTA ATTAGGCGCA TTGCTAGCAT
     ·  N  Y  N   E  K  F   K  T  R  F   T  I  S   V  D  R
651  CCAACTATAA CGAAAAATTT AAAACCCGCT TCACCATTAG CGTGGATCGT
     GGTTGATATT GCTTTTTAAA TTTTGGGCGA AGTGGTAATC GCACCTAGCA
                                      PstI
        S  K  S  T   A  Y  L   Q  M  D   S  L  R  A   E  D  T ·
701  AGCAAAAGCA CCGCGTATCT GCAGATGGAT AGCCTGCGTG CGGAAGATAC
     TCGTTTTCGT GGCGCATAGA CGTCTACCTA TCGGACGCAC GCCTTCTATG
             BssHII
     ·  A  V  Y   F  C  A  L   G  G  G   Y  A  M   D  Y  W  G ·
751  CGCGGTGTAT TTTTGCGCGC TGGGCGGTGG CTATGCGATG GATTATTGGG
     GCGCCACATA AAAACGCGCG ACCCGCCACC GATACGCTAC CTAATAACCC
                                                   NotI
     ·  Q  G  T   L  V  T   V  S  S  G   G  A  A   A  A  P
801  GCCAGGGCAC CCTGGTTACC GTGAGCAGCG GCGGTGCGGC CGCTGCACCA
     CGGTCCCGTG GGACCAATGG CACTCGTCGC CGCCACGCCG GCGACGTGGT
        S  V  F  I   F  P  P   S  D  E   Q  L  K  S   G  T  A ·
851  TCTGTCTTCA TCTTCCCGCC ATCTGATGAG CAGTTGAAAT CTGGAACTGC
```

Figure 10 b) cont.

```
          AGACAGAAGT AGAAGGGCGG TAGACTACTC GTCAACTTTA GACCTTGACG
          · S   V  V    C  L  L  N    N  F  Y    P  R  E    A  K  V  Q ·
    901   CTCTGTTGTG TGCCTGCTGA ATAACTTCTA TCCCAGAGAG GCCAAAGTAC
          GAGACAACAC ACGGACGACT TATTGAAGAT AGGGTCTCTC CGGTTTCATG
          · W   K  V    D  N  A    L  Q  S  G    N  S  Q    E  S  V
    951   AGTGGAAGGT GGATAACGCC CTCCAATCGG GTAACTCCCA GGAGAGTGTC
          TCACCTTCCA CCTATTGCGG GAGGTTAGCC CATTGAGGGT CCTCTCACAG
            T   E  Q  D    S  K  D    S  T  Y    S  L  S  S    T  L  T ·
    1001  ACAGAGCAGG ACAGCAAGGA CAGCACCTAC AGCCTCAGCA GCACCCTGAC
          TGTCTCGTCC TGTCGTTCCT GTCGTGGATG TCGGAGTCGT CGTGGGACTG
          · L   S  K    A  D  Y  E    K  H  K    V  Y  A    C  E  V  T ·
    1051  GCTGAGCAAA GCAGACTACG AGAAACACAA AGTCTACGCC TGCGAAGTCA
          CGACTCGTTT CGTCTGATGC TCTTTGTGTT TCAGATGCGG ACGCTTCAGT
          · H   Q  G    L  S  S    P  V  T  K    S  F  N    R  G  E
    1101  CCCATCAGGG CCTGAGTTCG CCCGTCACAA AGAGCTTCAA CCGCGGAGAG
          GGGTAGTCCC GGACTCAAGC GGGCAGTGTT TCTCGAAGTT GGCGCCTCTC
            S   H  H  H    H  H  H    *   *
    1151  TCACACCACC ACCACCACCA CTAGTAATT
          AGTGTGGTGG TGGTGGTGGT GATCATTAA
```

Figure 10 c)

L1-9.3Hu3 humanized single chain antibody

```
        NdeI
        M   K   Y   L   L   P   T   A   A   A   G   L   L   L   L   A  ·
  1  ACATATGAAA TACCTATTGC CTACGGCAGC CGCTGGATTG TTATTACTCG
     TGTATACTTT ATGGATAACG GATGCCGTCG GCGACCTAAC AATAATGAGC
        SfiI
                Ncol                                 AvaI
     ·  A   Q   P   A   M   A   D   I   Q   M   T   Q   S   P   S   S
  51 CGGCCCAGCC GGCCATGGCC GATATTCAGA TGACCCAGAG CCCGAGCAGC
     GCCGGGTCGG CCGGTACCGG CTATAAGTCT ACTGGGTCTC GGGCTCGTCG
            L   S   A   S   V   G   D   R   V   T   I   T   C   R   A   S   Q ·
 101 CTGAGCGCGA GCGTGGGTGA TCGTGTGACC ATTACCTGCC GTGCGAGCCA
     GACTCGCGCT CGCACCCACT AGCACACTGG TAATGGACGG CACGCTCGGT
     · D   I   S   N   Y   L   N   W   Y   Q   Q   K   P   G   K   A   P ·
 151 GGATATTAGC AACTATCTGA ACTGGTATCA GCAGAAACCG GGCAAAGCGC
     CCTATAATCG TTGATAGACT TGACCATAGT CGTCTTTGGC CCGTTTCGCG
     · K   L   L   I   Y   Y   T   S   R   L   H   S   G   V   P   S
 201 CGAAACTGCT GATTTATTAT ACCAGCCGTC TGCATAGCGG TGTGCCGAGC
     GCTTTGACGA CTAAATAATA TGGTCGGCAG ACGTATCGCC ACACGGCTCG
        R   F   S   G   S   G   S   G   T   D   Y   T   L   T   I   S   S ·
 251 CGTTTTAGCG GCAGCGGTAG CGGCACCGAT TATACCCTGA CCATTAGCAG
     GCAAAATCGC CGTCGCCATC GCCGTGGCTA ATATGGGACT GGTAATCGTC
        PstI
        ------
        · L   Q   P   E   D   F   A   T   Y   F   C   Q   Q   G   N   T   L ·
 301 CCTGCAGCCG GAAGATTTTG CGACCTATTT TTGCCAGCAG GGCAACACGC
     GGACGTCGGC CTTCTAAAAC GCTGGATAAA AACGGTCGTC CCGTTGTGCG
     · P   W   T   F   G   G   G   T   K   L   E   I   K   R   T   S
 351 TGCCGTGGAC CTTTGGCGGT GGCACCAAAC TGGAAATTAA ACGTACTAGT
     ACGGCACCTG GAAACCGCCA CCGTGGTTTG ACCTTTAATT TGCATGATCA
        G   P   G   D   G   G   K   G   G   P   G   K   G   P   G   G   E ·
 401 GGTCCGGGCG ATGGCGGTAA AGGCGGTCCG GGCAAAGGTC CGGGTGGCGA
     CCAGGCCCGC TACCGCCATT TCCGCCAGGC CCGTTTCCAG GCCCACCGCT
                SmaI
                XmaI
                AvaI
        · G   T   K   G   T   G   P   G   G   E   V   Q   L   V   Q   S   G ·
 451 AGGCACCAAA GGCACTGGGC CCGGGGGTGA AGTTCAGCTG GTGCAGAGCG
     TCCGTGGTTT CCGTGACCCG GGCCCCCACT TCAAGTCGAC CACGTCTCGC
     · G   G   L   V   Q   S   G   G   S   L   R   L   S   C   R   A
 501 GCGGTGGTCT GGTTCAGAGC GGTGGCAGCC TGCGTCTGAG CTGTCGTGCG
     CGCCACCAGA CCAAGTCTCG CCACCGTCGG ACGCAGACTC GACAGCACGC
        S   G   Y   T   F   T   R   Y   W   M   L   W   V   R   Q   R   P ·
 551 AGCGGCTATA CCTTTACCCG TTATTGGATG CTGTGGGTGC GTCAGCGTCC
     TCGCCGATAT GGAAATGGGC AATAACCTAC GACACCCACG CAGTCGCAGG
     · G   K   G   L   E   W   V   A   E   I   N   P   R   N   D   R   T ·
 601 GGGTAAAGGC CTGGAATGGG TGGCGGAAAT TAATCCGCGT AACGATCGTA
     CCCATTTCCG GACCTTACCC ACCGCCTTTA ATTAGGCGCA TTGCTAGCAT
     · N   Y   N   E   K   F   K   T   R   F   T   I   S   V   D   R
 651 CCAACTATAA CGAAAAATTT AAAACCCGCT TCACCATTAG CGTGGATCGT
     GGTTGATATT GCTTTTTAAA TTTTGGGCGA AGTGGTAATC GCACCTAGCA
                                PstI
        S   K   N   T   L   Y   L   Q   M   D   S   L   R   A   E   D   T ·
 701 AGCAAAAACA CCCTGTATCT GCAGATGGAT AGCCTGCGTG CGGAAGATAC
     TCGTTTTTGT GGGACATAGA CGTCTACCTA TCGGACGCAC GCCTTCTATG
                BssHII
        · A   V   Y   F   C   A   L   G   G   G   Y   A   M   D   Y   W   G ·
 751 CGCCGTGTAT TTTTGCGCGC TGGGCGGTGG CTATGCGATG GATTATTGGG
     GCGGCACATA AAAACGCGCG ACCCGCCACC GATACGCTAC CTAATAACCC
                                                                NotI
        · Q   G   T   L   V   T   V   S   S   G   A   A   A   A   P
 801 GCCAGGGCAC CCTGGTTACC GTGAGCAGCG GCGGTGCGGC CGCTGCACCA
```

Figure 10 c) cont.

```
            CGGTCCCGTG GGACCAATGG CACTCGTCGC CGCCACGCCG GCGACGTGGT
             S  V  F  I  F  P  P  S  D  E  Q  L  K  S  G  T  A  ·
       851  TCTGTCTTCA TCTTCCCGCC ATCTGATGAG CAGTTGAAAT CTGGAACTGC
            AGACAGAAGT AGAAGGGCGG TAGACTACTC GTCAACTTTA GACCTTGACG
             ·  S  V  V  C  L  L  N  N  F  Y  P  R  E  A  K  V  Q  ·
       901  CTCTGTTGTG TGCCTGCTGA ATAACTTCTA TCCCAGAGAG GCCAAAGTAC
            GAGACAACAC ACGGACGACT TATTGAAGAT AGGGTCTCTC CGGTTTCATG
             ·  H  K  V  D  N  A  L  Q  S  G  N  S  Q  E  S  V
       951  AGTGGAAGGT GGATAACGCC CTCCAATCGG GTAACTCCCA GGAGAGTGTC
            TCACCTTCCA CCTATTGCGG GAGGTTAGCC CATTGAGGGT CCTCTCACAG
             T  E  Q  D  S  K  D  S  T  Y  S  L  S  S  T  L  T  ·
      1001  ACAGAGCAGG ACAGCAAGGA CAGCACCTAC AGCCTCAGCA GCACCCTGAC
            TGTCTCGTCC TGTCGTTCCT GTCGTGGATG TCGGAGTCGT CGTGGGACTG
             ·  L  S  K  A  D  Y  E  K  H  K  V  Y  A  C  E  V  T  ·
      1051  GCTGAGCAAA GCAGACTACG AGAAACACAA AGTCTACGCC TGCGAAGTCA
            CGACTCGTTT CGTCTGATGC TCTTTGTGTT TCAGATGCGG ACGCTTCAGT
             ·  H  Q  G  L  S  S  P  V  T  K  S  F  N  R  G  E
      1101  CCCATCAGGG CCTGAGTTCG CCCGTCACAA AGAGCTTCAA CCGCGGAGAG
            GGGTAGTCCC GGACTCAAGC GGGCAGTGTT TCTCGAAGTT GGCGCCTCTC
             S  H  H  H  H  H  H  ·  ·
      1151  TCACACCACC ACCACCACCA CTAGTAATT
            AGTGTGGTGG TGGTGGTGGT GATCATTAA
```

Figure 12 a)

GAAGAGTTAGCCTTGCAGCTGTGCTCAGCCCTAAATAGTTCCCAAAAATTTGCATGCTCTCACTTC
CTATCTTTGGGTACTTTTTCATATACCAGTCAGATTGTGAGCCATTGTAATTGAAGTCAAGACTCA
GCCTGGAC*ATGATGTCCTCTGCTCAGTTCCTTGGTCTCCTGTTGCTCTGTCTTCAAGG*TAAAAGT
TACTACAATGGGAATTTTGCTGTTGCACAGTGATTCTTGTTGACTGGAATTTTGGAGGGGTCCTTT
CTTTTCCTGCTTAACTCTGTGGGTATTTATTGTGTCTCCACTCCTAGGTACCAGATGTGATATCCA
GATGACACAGACTACATCCTCCCTGTCTGCCTTTCTGGGAGACAGAGTCACCATCAGTTGCAG
GGCAAGTCAGGACATTAGCAATTATTTAAACTGGTATCAGCAGAAACCAGATGGAACTGTTAAA
CTCCTTATCTATTACACATCAAGATTACACTCAGGAGTCCCCTCAAGGTTCAGTGGCAGTGGGT
CTGGAACAGATTATTCTCTCACCATTAGCAACCTGGAGCAAGAAGATTTTGCCACTTACTTTTGC
CAACAGGGTAATACGCTTCCGTGGACATTCGGTGGAGGCACCAAGCTGGAAATCAAACGTAAA
TAGAATCCAAAGTCTCTTTCTTCCGTTGTCTATGTCTGTGGCTTCTATGTCTACAAATGATGTAT b)

TTCAGCATCCTGATTCCTGACCCAGGTGTCCCTTCTTCTCCAGCAGGAGTAGGTGCTCATCTAAT
ATGTATCCTGCTCATGAATATGCAAATCCTCTGAATCTACATGGTAAATGTAGGTTTGTCTATATCA
CACACAGAAAAACATGAGATCACAGTTCTCTCTACAGTTACTGAACACACAGGACCTCACC*ATGG
GATGGAGCTATATCATCCTCTTTTTGGTAGCAACAGCTAC*AGGTAAGGGGCTCACAGTAGAAGG
CTTGAGGTCTGGCCATATACATGGGTGACAGTGACATCCACTTTGCCTTTCTTTCCACAGATGTC
CACTCCCAGGTCCAACTGCAGCAGCCTGGGGCTGAACTGGTGAAGTCTGGGGCTTCAGTGAAC
CTGTCCTGCAGGGCTTCTGGCTACACCTTCACCAGATACTGGATGCTCTGGGTGAGGCAGAGG
CCTGGACATGGCCTTGAGTGGGTTGGAGAGATTAATCCTCGCAACGATCGTACTAATTACAATG
AGAAATTCAAGACCAAGGCCACACTGACTGTAGACCGATCCTCCAGCACAGCCTACATGCAAC
TCACCAGCCTGACATCTGAGGACTCTGCGGTCTATTTCTGTGCCCTGGGGGGGGCTATGCTAT
GGACTATTGGGGTCAAGGAACCTCAGTCACCGTCCTCAGGTAAGAATGGCCTCTCCAGGTCT
TAATTTTTAACCTTTGTTATGGAGTTTTCTGAGCATTGCAGACTAATCTTGGATATTTGTCCCTGAG
GGAGCCGGCTGAGAGAAGTTGGGAAATAAACTGTCTAGGGATCTCAGAGCCTTTAGGACAGATT
A

A)

B)

Figure 14
A)
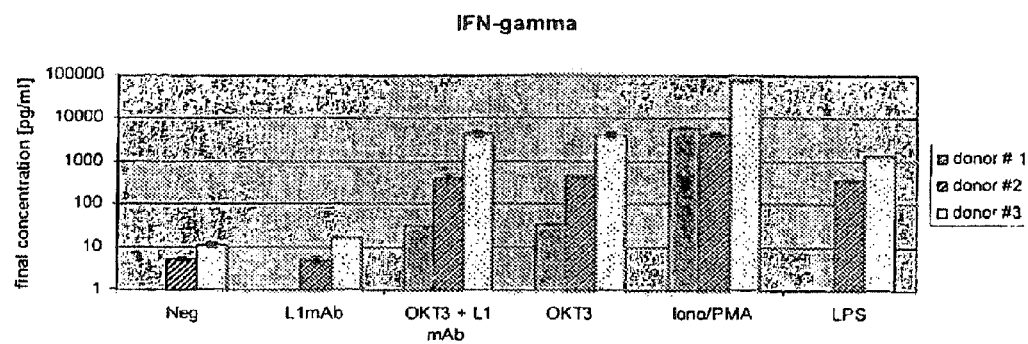
B)
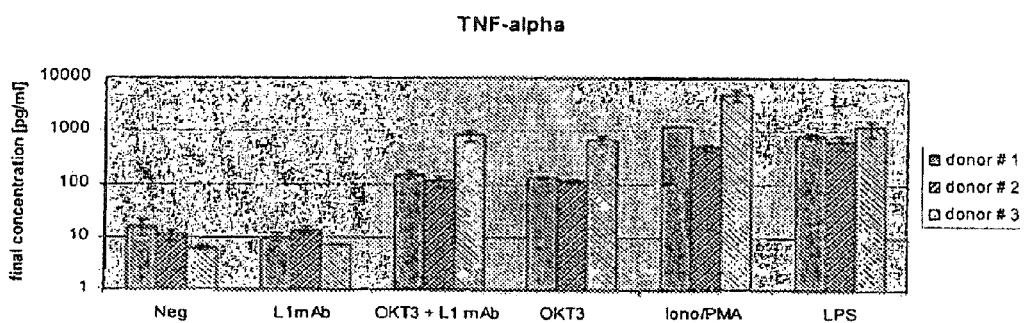

Caspase-3/-7 activity:
in PT45res cells after stimulation with gemcitabine and L1-9.3 antibody Caspase-3/-7 activity:
in PT45res cells after stimulation with etoposide and L1-9.3 antibody

TREATMENT OF TUMORS USING SPECIFIC ANTI-L1 ANTIBODY

This application is a continuation of U.S. patent application Ser. No. 13/367,178, filed Feb. 6, 2012, now U.S. Pat. No. 8,580,258, which is a divisional of U.S. patent application Ser. No. 12/139,006, filed Jun. 13, 2008, now U.S. Pat. No. 8,138,313, which application claims benefit of U.S. provisional application Ser. No. 60/944,359 filed Jun. 15, 2007. U.S. patent application Ser. Nos. 13/367,178 and 12/139,006 and U.S. provisional application Ser. No. 60/944,359 are incorporated herein by reference in their entireties.

SEQUENCE LISTING

The instant application contains a Sequence Listing which has been submitted electronically in ASCII format and is hereby incorporated by reference in its entirety. Said ASCII copy, created on Dec. 27, 2013, is named 8167-108DVC_S-L.txt and is 51,219 bytes in size.

The present invention relates to the treatment of tumors by the use of a specific anti-L1 antibody.

The standard treatment of advanced cancer is often chemotherapy or radiotherapy. However, despite initial response to therapy, it is often observed that different carcinomas acquire resistance to chemotherapeutic drugs or radiotherapy leading to tumor recurrence and frequent death of the patients. Often, it is then decided to switch to another chemotherapeutic drug or to higher dosages. However, often no improvement of the clinical situation is observed.

L1 is a type I membrane glycoprotein of 200 to 230 kDa structurally belonging to the Ig superfamily (Moos M, Tacke R, Scherer H, Teplow D, Fruh K, Schachner M. Neural adhesion molecule L1 as a member of the immunoglobulin superfamily with binding domains similar to fibronectin. Nature 1988; 334:701-3). L1 plays a crucial role in axon guidance and cell migration in developing nervous system (Hortsch M. Structural and functional evolution of the L1 family: are four adhesion molecules better than one? Mol Cell Neurosci 2000; 15:1-10, Schachner M. Neural recognition molecules and synaptic plasticity. Curr Opin Cell Biol 1997; 9:627-34). Recent studies have also implicated L1 expression in the progression of human carcinomas. L1 expression was found on different tumors including lung cancer (Katayama M, Iwamatsu A, Masutani H, Furuke K, Takeda K, Wada H, et al. Expression of neural cell adhesion molecule L1 in human lung cancer cell lines. Cell Struct Funct 1997; 22:511-6), gliomas (Senner V, Kismann E, Puttmann S, Hoess N, Baur I, Paulus W. L1 expressed by glioma cells promotes adhesion but not migration. Glia 2002; 38:146-54), melanomas (Thies A, Schachner M, Moll I, Berger J, Schulze H J, Brunner G, et al. Overexpression of the cell adhesion molecule L1 is associated with metastasis in cutaneous malignant melanoma. Eur J Cancer 2002; 38:1708-1, Fogel M, Mechtersheimer S, Huszar M, Smirnov A, Abu D A, Tilgen W, et al. L1 adhesion molecule (CD 171) in development and progression of human malignant melanoma. Cancer Lett 2003; 189:237-47), renal carcinoma (Meli M L, Carrel F, Waibel R, Amstutz H, Crompton N, Jaussi R, Moch H, Schubiger P A, Novak-Hofer I. Anti-neuroblastoma antibody chCE7 binds to an isoform of L1-CAM present in renal carcinoma cells. Int J Cancer, 1999; 83: 401-408, Allory Y, Matsuoka Y, Bazille C, Christensen El, Ronco P, Debiec H. The L1 cell adhesion molecule is induced in renal cancer cells and correlates with metastasis in clear cell carcinomas. Clin Cancer Res 2005; 11:1190-7) and colon carcinoma (Gavert N, Conacci-Sorrell M, Gast D, Schneider A, Altevogt P, Brabletz T, et al. L1, a novel target of beta-catenin signaling, transforms cells and is expressed at the invasive front of colon cancers. J Cell Biol 2005; 168:633-42). Furthermore, it is known in the art that L1 is overexpressed in ovarian and endometrial carcinomas in a stage-dependent manner (Fogel M, Gutwein P, Mechtersheimer S, Riedle S, Stoeck A, Smirnov A, et al. L1 expression as a predictor of progression and survival in patients with uterine and ovarian carcinomas. Lancet 2003; 362:869-75).

In the art, it has been suggested to use anti-L1 antibodies for the treatment of ovarian and endometrial tumors (cf. WO 02/04952, WO 06/013051 and Arlt M J, Novak-Hofer I, Gast D, Gschwend V, Moldenhauer G, Grunberg J, et al. Efficient inhibition of intra-peritoneal tumor growth and dissemination of human ovarian carcinoma cells in nude mice by anti-L1-cell adhesion molecule monoclonal antibody treatment. Cancer Res 2006; 66:936-43). In the art, various anti-L1 antibodies are known (e.g. mAb 14.10: Huszar M, Moldenhauer G, Gschwend V, Ben-Arie A, Altevogt P, Fogel M: Expression profile analysis in multiple human tumors identifies L1 (CD171) as a molecular marker for differential diagnosis and targeted therapy. *Hum Pathol* 37:1000-1008, 2006, mab chCE7: Meli M L, Carrel F, Waibel R, Amstutz H, Crompton N, Jaussi R, Moch H, Schubiger P A, Novak-Hofer I: Anti-neuroblastoma antibody chCE7 binds to an isoform of L1-CAM present in renal carcinoma cells. *Int J Cancer* 83:401-408, 1999, mAb UJ127.11: Patel K, Kiely F, Phimister E, Melino G, Rathjen F, Kerashead J T: The 200/220 kDa antigen recognized by monoclonal antibody (MAb) UJ127.11 on neural tissues and tumors is the human L1 adhesion molecule. *Hybridoma* 10:481-491, 1991, mAb 5G3: Wolff J M, Frank R, Mujoo K, Spiro R C, Reisfeld R A, Rathjen F G: A human brain glycoprotein related to the mouse cell adhesion molecule L1. *J Biol Chem* 263:11943-11947, 1988). Furthermore, in Sebens Müelerkoster et al., Oncogene. 2007 Apr. 26; 26(19):2759-68, Epub 2006 Nov. 6, it has been suggested to use anti-L1 antibodies for sensitizing tumor cells for the treatment with a chemotherapeutic drug or with radiotherapy.

There is always a need for improved anti-tumor agents.

The present invention relates in one aspect to an anti-L1 monoclonal antibody which is capable of binding to the same L1 epitope recognized by the monoclonal antibody 9.3, produced by the hybridoma cell deposited under DSMZ ACC2841.

In the context of the present invention, it has been surprisingly found that the monoclonal antibody 9.3, produced by the hybridoma cell deposited under DSMZ ACC2841, has improved anti-tumor capacities (see examples). Especially, the monoclonal antibody 9.3 has the best ability to inhibit tumor growth and invasion of tumor cells of all antibodies tested. Furthermore, the monoclonal antibody 9.3 seems to abolish chemoresistance to a greater extend than the antibody 11A tested in WO 2008/046529 (see example 13).

Monoclonal antibodies and the production of monoclonal antibodies belongs to the state of the art and is also described in the references cited in the Materials and Methods section of the examples. In general, monoclonal antibodies can, for example, be prepared in accordance with the known method of Winter & Milstein (Winter, G. & Milstein, C. (1991) Nature, 349, 293-299). An alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; WO 92/18619; WO 91/17271; WO 92/20791; WO 92/15679; WO 93/01288; WO 92/01047; WO 92/09690; WO 90/02809; Fuchs et al., 1991, Bio/Technology 9:1370-1372; Hay et al., 1992, Hum. Antibod. Hybridomas 3:81-85; Huse et al., 1989, Science 246:1275-1281; Griffiths et al., 1993, EMBO J. 12:725-734.

Since the effect of an antibody is mediated by its capacity to bind a specific epitope, the invention relates to all monoclonal antibodies recognizing the same epitope as the antibody 9.3. Methods for determining the epitope of a given antibody are known in the art and include the preparation of synthetic linear peptides of a given region of interest and the subsequent testing whether the antibody binds to said peptides (see Epitope Mapping, A practical approach, Oxford University Press 2001, Editors: Olwyn Westwood and Frank Hay). Alternatively, different recombinant proteins covering the region of interest can be produced and tested for the binding of the antibody (Oleszewski, M., Gutwein, P., von der Lieth, W., Rauch, U., Altevogt, P. Characterization of the L1-neurocan binding site. Implications for L1-L1 homophilic binding. J. Biol. Chem. 275: 34478-34485 (2000).)

Furthermore, once a specific epitope of a monoclonal antibody is known, it is within the skill of the person skilled in the art to identify or prepare other antibodies, especially monoclonal antibodies, or binding molecules as defined below which bind to the same epitope. For example, it is possible to use the peptides or proteins described above in the context of the epitope mapping also for the identification or production of said antibodies or binding molecules.

As it can be taken from the examples, the epitope of the antibody 9.3 is with the first immunoglobulin-like domain of L1. Therefore also the epitope of the monoclonal antibody of the invention is preferably within the first immunoglobulin-like domain of L1.

In another aspect, the invention relates to an anti-L1 monoclonal antibody, having the same capacity to inhibit tumor growth as the monoclonal antibody 9.3, produced by the hybridoma cell deposited under DSMZ ACC2841. This capacity can be tested by using the same tumor growth assay as described in the Example 1, section 1.3.9. According to the invention, "the same capacity" means that the monoclonal antibody has a tumor growth inhibiting capacity which does not differ more than 5% from the tumor growth inhibiting capacity of the monoclonal antibody 9.3.

Preferably, this antibody of the invention also inhibits L1 dimerization, as it has been shown for the antibody 5G3 (see above).

In another aspect, the invention relates to an anti-L1 monoclonal antibody, characterized in that at least one of its complementarity determining regions (CDRs)
   a) has one of the following sequences RASQDISNYLN (SR) ID NO: 1), YTSRLHS (SEQ ID NO: 2), QQGNTLPWT (SEQ ID NO: 3), RYWML (SEQ ID NO: 4), EINPRNDRTNYNEKFKT (SEQ ID NO: 5), or GGGYAMDY (SEQ ID NO: 6) or
   b) has a sequence which, in comparison to the sequences mentioned under a) has at least one conservative amino acid exchange.

The above mentioned sequences show the CDRs of the monoclonal antibody 9.3 determined according to the method of Kabat (see Example 2). Such a monoclonal antibody of the invention can, e.g. be produced by CDR grafting or by recombinant production of the antibody. Such methods are known in the art (see e.g. Queen, U.S. Pat. No. 5,585,089 and Winter, U.S. Pat. No. 5,225,539, Cabilly U.S. Pat. No. 4,816,567).

In another aspect, the inventions also relates to an anti-L1 monoclonal antibody, characterized in that at least one of its complementarity determining regions (CDRs)
   a) has one of the following sequences QDISNY (SEQ ID NO: 7), YTS, QQGNTLPWT (SEQ ID NO: 8), GYTFTRYW (SEQ ID NO: 9), INPRNDRT (SEQ ID NO: 10), or ALGGGYAMDY (SEQ ID NO: 11) or
   b) has a sequence which, in comparison to the sequences mentioned under a) has at least
   one conservative amino acid exchange.

These sequences show again the CDRs of the monoclonal antibody 9.3 (see FIG. 12), but the CDRs have been determined using another method known in the art, namely according to the IMGT® method from the international ImMunoGeneTics information system®.

In an especially preferred aspect, the invention relates to a monoclonal antibody, produced by the hybridoma cell deposited under DSMZ ACC2841. This hybridoma cell has been deposited with the Deutsche Sammlung für Mikroorganismen and Zellen on Apr. 25, 2007 under the Budapest Treaty.

In another aspect, the invention relates to a humanized antibody based on the monoclonal antibody of the invention as described above.

Humanized antibodies are antibody molecules from non-human species having one or more complementarily determining regions (CDRs) from the non-human species and a framework region (FR) from a human immunoglobulin molecule (See, e.g., Queen, U.S. Pat. No. 5,585,089 and Winter, U.S. Pat. No. 5,225,539.) Such chimeric and humanized monoclonal antibodies can be produced by recombinant DNA techniques known in the art.

In general, in order to obtain a humanised antibody, nucleic acid sequences encoding human variable heavy chains and variable light chains may be altered by replacing one or more CDR sequences of the human (acceptor) sequence by sequence encoding the respective CDR in the mouse antibody sequence (donor sequence). The human acceptor sequence may comprise FR derived from different genes.

In a preferred embodiment, the humanized antibody of the invention has at least one non-human CDR and human framework region (FR) residues.

Sequences encoding full length antibodies can be subsequently obtained by joining the rendered variable heavy and variable light chain sequences to human constant heavy chain and constant light chain regions. Preferred human constant light chain sequences include kappa and lambda constant light chain sequences. Preferred human constant heavy chain sequences include IgG1, IgG2 and sequences encoding IgG1 mutants which have rendered immune-stimulating properties. Such mutants may have a reduced ability to activate complement and/or antibody dependent cellular cytotoxicity and are described in U.S. Pat. No. 5,624,821; WO 99/58572, U.S. Pat. No. 6,737,056. An especially preferred constant heavy chain is an IgG1 comprising the substitutions E233P, L234V, L235A, A327G, A330S, P331S and a deletion of residue 236.

In another embodiment, the full length antibody comprises an IgA, IgD, IgE, IgM, IgY or IgW sequence.

Suitable human donor sequences can be determined by sequence comparison of the peptide sequences encoded by the mouse donor sequences to a group of human sequences, preferably to sequences encoded by human germ line immuno globulin genes or mature antibody genes. A human sequence with a high sequence homology, preferably with the highest homology determined may serve as the acceptor sequence to for the humanization process.

In addition to the exchange of human CDRs for mouse CDRs, further manipulations in the human donor sequence may be carried out to obtain a sequence encoding a humanized antibody with optimized properties (such as affinity of the antigen).

In a preferred example, heavy chain residues 31-35, 50-58 and 95-102 and residues 6, 23, 24, and 49 in the human acceptor sequence are altered to correspond to the respective residues of the mouse sequence (Adair, U.S. Pat. No. 5,859, 205).

Furthermore the altered human acceptor antibody variable domain sequences may also be rendered to encode one or more amino acids (according to the Kabat numbering system) of position 4, 35, 38, 43, 44, 46, 58, 62, 64, 65, 66, 67, 68, 69, 73, 85, 98 of the light variable region and 2, 4, 36, 39, 43, 45, 69, 70, 74, 75, 76, 78, 92 of the heavy variable region corresponding to the mouse donor sequence (Carter and Presta, U.S. Pat. No. 6,407,213)

The humanisation of an mouse L1 antibody is described in Example 2.

Also the sequences of the CDRs may be altered, preferably by exchanges leading to a conservative amino acid exchange.

In general, manipulations may result in alterations in the FR as well as the CDR regions and include exchanges, deletions and insertion of residues. The alterations may be induced by random or directed mutagenesis. An antibody phage display system, as described before, may be employed for the selection of mutants with desired and/or improved properties In another aspect the invention relates to a human antibody capable of recognizing the same epitope as the antibody 9.3. Methods for generating human antibodies are known in the art. These methods employ for example mice in which the endogenous immunoglobuline genes have been partially or completely inactivated and human immunoglobulin loci were introduced. Upon immunization with an immunogenic epitope, these mice are capable of producing human antibodies (U.S. Pat. Nos. 5,545,807; 5,545,806; 5,569,825; 5,589, 369; 5,591,669; 5,625,126; 5,633,425; 5,661,016)

In a further preferred embodiment, the humanized antibody of the invention comprises the sequence of L1__9.3hu or L1__9.3hu3 as shown in FIGS. 8 a) and b).

In another aspect, the invention relates to a binding molecule comprising
  a) at least one of the following sequences RASQDISNYLN (SEQ ID NO: 1), YTSRLHS (SEQ ID NO: 2), QQGNTLPWT (SEQ ID NO: 3), RYWML (SEQ ID NO: 4), EINPRNDRTNYNEKFKT (SEQ ID NO: 5), or GGGYAMDY (SEQ ID NO: 6) or
  b) at least one sequence which has in comparison to the sequences given in a) at least one conservative amino acid exchange.

As explained above, these sequences show the CDRs of the antibody 9.3 (see Example 2).

In another aspect, the invention relates to a binding molecule comprising
  a) at least one of the following sequences QDISNY (SEQ ID NO: 7), YTS, QQGNTLPWT (SEQ ID NO: 8), GYTFTRYW (SEQ ID NO: 9), INPRNDRT (SEQ ID NO: 10), or ALGGGYAMDY (SEQ ID NO: 11) or
  b) at least one sequence which has in comparison to the sequences given in a) at least one conservative amino acid exchange.

As explained above, these sequences show again the CDRs of the monoclonal antibody 9.3, determined by another method known in the art.

According to the invention, a binding molecule is a molecule capable of binding L1. Preferably, the binding molecule is an immunoglobulin comprising molecule, i.e. comprises at least one Ig domain.

In a preferred embodiment, the binding molecule of the invention is selected from the group consisting of single chain antibodies (e.g. scFv, multimers of scFv like diabodies, triabodies or tetrabodies, antibody fragments (e.g. Fab), tandabs, flexibodies, bispecific antibodies, and chimeric antibodies.

The structure of an antibody and especially the function of its CDRs is known in the art (Carter P J. Potent antibody therapeutics by design. Nature Rev. Immunol. 6:343-357, 2006).

scFv and multimers thereof, tandabs, diabodies and flexibodies are standard antibody formats known in the art, e.g. from WO 88/1649, WO 93/11161, WO 99/57150 and EP1293514B1.

In single chain Fv (scFv) the two antigen binding variable regions of the light and heavy chain (VH Fv and VL Fv) of an antibody are artificially connected by a linker peptide, designated as single chain variable fragment or single chain antibody (Bird, et al. (1988) Science 242:423-426; Orlandi, et al (1989) Proc Natl Acad Sci USA 86:3833-3837; Clarkson et al., Nature 352: 624-628 (1991)). The antigen binding site is made up of the variable domains of light and heavy chains of a monoclonal antibody. Several investigations have shown that the Fv fragment has indeed the full intrinsic antigen binding affinity of one binding site of the whole antibody.

In the context of this invention, diabodies are scFv with two binding specificities and can either be monospecific and bivalent or bispecific and bivalent.

Tandabs and flexibodies are further antibody formats which are e.g. defined in US2007031436 and EP1293514, respectively.

Antibody fragments that contain the idiotypes of the protein can be generated by techniques known in the art. For example, such fragments include, but are not limited to, the F(ab')2 fragment which can be produced by pepsin digestion of the antibody molecule; the Fab' fragment that can be generated by reducing the disulfide bridges of the F(ab')2 fragment; the Fab fragment that can be generated by treating the antibody molecular with papain and a reducing agent; and Fv fragments.

A chimeric antibody is a molecule in which different portions are derived from different animal species, such as those having a variable region derived from a murine mAb and a human immunoglobulin constant region (See, e.g., Cabilly et al., U.S. Pat. No. 4,816,567; and Boss et al., U.S. Pat. No. 4,816,397).

Bifunctional, or bispecific, antibodies have antigen binding sites of different specificities. Various forms of bispecific antibodies have been produced. These include BSIgG, which are IgG molecules comprising two distinct heavy chains and two distinct light chains that are secreted by so-called "hybrid hybridomas", and heteroantibody conjugates produced by the chemical conjugation of antibodies or antibody fragments of different specificities (Segal D M, Weiner G J, Weiner L M. Bispecific antibodies in cancer therapy. Current Opin. Immunol. 11:558-562, 1999, Van Spriel A B, Van Ojik H H, Van de Winkel J G J. Immunotherapeutic perspective for bispecific antibodies. Immunology Today 21:391-397, 2000).

Bispecific antibodies have been generated to deliver cells, cytotoxins, or drugs to specific sites. An important use has been to deliver host cytotoxic cells, such as natural killer or cytotoxic T cells, to specific cellular targets (P. J. Lachmann, Clin. Exp. Immunol. 79: 315 (1990)). Another important use has been to deliver cytotoxic proteins to specific cellular targets (V. Raso, T. Griffin, Cancer Res. 41:2073 (1981); S. Honda, Y. Ichimori, S. Iwasa, Cytotechnology 4:59 (1990)). Another important use has been to deliver anti-cancer non-protein drugs to specific cellular targets (J. Corvalan, W. Smith, V. Gore, Intl. J. Cancer Suppl. 2:22 (1988); M. Pimm et al., British J. of Cancer 61:508 (1990)). Such bispecific antibodies have been prepared by chemical cross-linking (M. Brennan et al., Science 229:81 (1985)), disulfide exchange, or the production of hybrid-hybridomas (quadromas). Quadromas are constructed by fusing hybridomas that secrete two different types of antibodies against two different antigens (Kurokawa, T. et al., Biotechnology 7.1163 (1989)).

In a preferred embodiment of the invention, the antibody or binding molecule of the invention is linked to an active substance, preferably a toxin, a nanoparticle, a cytokine, or a radionucleotide. Such antibody conjugates are known in the art (Wu A M, Senter P D. Arming antibodies: prospects and challenges for immunoconjugates. Nature Biotechnol. 23:1137-1146, 2005, Pastan I, Hassan R, FitzGerald D J, Kreitman R J. Immunotoxin treatment of cancer. Annu. Rev. Med. 58:221-237, 2007, WO 90/12592, WO 2007/030642, WO 2004/067038, WO 2004/003183, US 2005/0074426, WO 94/04189).

In a preferred embodiment, the antibody or binding molecule of the invention binds L1 with an affinity (KD) of at least $10^{-8}$, preferably of at least $10^{-9}$, more preferably of at least $10^{-10}$ or $10^{-11}$.

Preferably, the antibody of the invention does not significantly bind to other members of the L1-protein family as for example CHL1 (close homolog of L1, accession number NM_006614), NrCAM (Neuronal cell adhesion protein, accession number NM_001037132 or NM_005010) and/or NFASC (Neurofascin, accession number NM_015090). Preferably the antibody binds the other members of the L1-family with an at least 100-fold lower affinity, more preferably at least 1000-fold lower affinity compared to the affinity for L1. The affinity of the antibody for the different proteins can be determined for example by measuring the binding affinity to recombinant proteins as described in example 6. The binding of the antibody to the different L1 family members of the L1-family may also be determined by expressing said proteins on CHO cells and measuring the antibody binding by FACS analysis as described in Example 1.2 and Example 7.

It is one aspect of the invention that the antibody does not significantly increase the release of cytokines, e.g. tumour necrosis factor-alpha or interferon gamma. Preferably the release is not increased by more than 30%, more preferably not more than 20% and most preferably not more than 10%. The release of cytokines can be tested as described in Example 8. Alternatively the concentration of cytokines can be determined in the blood of an animal before and after the ministration of the antibody. The cytokine concentration may be determined by an ELISA assay or other methods known in the art.

In another preferred embodiment the antibody does not significantly induce T-cell proliferation or inhibit T-cell proliferation. The effect of an antibody on T-cell proliferation can be determined as described in Example 9.

The invention further relates to a binding molecule which is capable of binding to the same L1 epitope recognized by the monoclonal antibody 9.3, produced by the hybridoma cell deposited under DSMZ ACC2841. Preferably, with respect to this binding molecule of the invention, the same embodiments defined with respect to the structure of the binding molecule described above also apply to this binding molecule of the invention.

Preferably, the binding of the antibody to the epitope is not significantly increased or decreased by the glycosylation state of the L1 protein. The influence of the glycosylation state on the antibody binding can be determined as described in Example 10.

Furthermore, the invention relates to a hybridoma cell that produces the monoclonal antibody of the invention.

Furthermore, the invention relates to the hybridoma cell deposited under DSMZ ACC2841.

As explained above and as described in the example section, the monoclonal antibody or binding molecule of the invention is especially suitable for the treatment of tumorigenic diseases.

Therefore, in another aspect, the invention relates to the use of the antibody of the invention or the binding molecule of the invention for the preparation of a medicament for the treatment of a tumorigenic disease.

Furthermore, the invention also relates to a method for treating a tumorigenic disease, wherein an antibody or binding molecule of the invention is administered to a subject in an effective amount to treat said disease. With respect to said method of the invention, all embodiments as defined below for the use of the invention also apply.

As mentioned above, in the art it has been suggested to use anti-L1 antibodies for sensitizing tumor cells for the treatment with a chemotherapeutic drug or with radiotherapy (see Sebens Müerkoster et al., Oncogene. 2007 Apr. 26; 26(19): 2759-68, Epub 2006 Nov. 6). Consequently, in another aspect, the present invention relates to the use of the antibody of the invention or the binding molecule of the invention for sensitizing tumor cells in a patient for the treatment with a chemotherapeutic drug or with radiotherapy.

This aspect of the present invention is especially useful in cases where the tumor cells are at least partially resistant to chemotherapy or to radiotherapy.

Therefore, in a preferred embodiment of the invention, the cells to be sensitized are at least partially resistant to the treatment with said chemotherapeutic drug or to radiotherapy.

In the context of the present invention, the term "sensitizing" is to be understood that after the treatment with the anti L1 antibody or binding molecule of the invention, the tumor cells are more susceptible to the treatment with a chemotherapeutic drug or with radiotherapy than before said treatment. This can e.g. be tested by isolating tumor cells from the patient and testing in vitro whether the treatment with said antibody or binding molecule of the invention results in a sensitization of the cells. This test can be performed as described in reference (Sebens Müerkoster et al., Oncogene. 2007 Apr. 26; 26(1 9):2759-68, Epub 2006 Nov. 6).

In a preferred embodiment, the cells, before the administration of the anti L1 antibody or binding molecule of the invention, were not susceptible to the treatment or only susceptible to an extend that the treatment with a chemotherapeutic drug or with radiotherapy would not result in the desired therapeutic effect.

Preferably, with the help of the anti-L1 antibody or binding molecule of the invention, the susceptibility is increased by at least 20%, more preferably by at least 40% and even more preferably by at least 100%.

An overview over chemotherapeutic drugs and radiotherapy is e.g. given in Remmington's Pharmaceutical Sciences, 5th ed., chapter 33, in particular pages 624 to 652.

Any of numerous chemotherapeutic drugs can be used in the methods or uses of the invention. These compounds fall into several different categories, including, for example, alkylating agents, antineoplastic antibiotics, antimetabolites, and natural source derivatives.

Examples of alkylating agents that can be used in the invention include busulfan, caroplatin, carmustine, chlorambucil, cisplatin, cyclophosphamide (i.e., cytoxan), dacarbazine, ifosfamide, lomustine, mecholarethamine, melphalan, procarbazine, streptozocin, and thiotepa.

Examples of antineoplastic antibiotics include bleomycin, dactinomycin, daunorubicin; doxorubicin, idarubicin; mitomycin (e.g., mitomycin C), mitoxantrone, pentostatin, and plicamycin.

Examples of antimetabolites include fluorodeoxyuridine, cladribine, cytarabine, floxuridine, fludarabine, fluorouracil (e.g., 5-fluorouracil (5FU)), gemcitabine, hydroxyurea, mercaptopurine, methotrexate, and thioguanine.

Examples of natural source derivatives include docetaxel, etoposide, irinotecan, taxanes (e.g. paclitaxel), teniposide, topotecan, vinblastine, vincristine, vinorelbine, prednisone, and tamoxifen.

Additional examples of chemotherapeutic agents that can be used in the invention include asparaginase and mitotane.

Furthermore, also C2 ceramide can be used.

In an especially preferred embodiment, the chemotherapeutic drug is selected from the group consisting of actinomycin-D, mitomycin C, cisplatin, doxorubicin, etoposide, verapamil, podophyllotoxin, 5-FU, taxans such as paclitaxel, and carboplatin.

According to the invention, the term "radiotherapy" refers to each radiation therapy which is commonly used to treat tumors cells. In a preferred embodiment, this therapy include γ-rays, X-rays, microwaves, UV radiation as well as the direct delivery of radio-isotopes to or next to tumor cells (brachytherapy).

As mentioned above, the object of this aspect of the invention is to sensitize tumor cells for the treatment with a chemotherapeutic drug or with radiotherapy. Consequently, in a preferred embodiment, after the sensitization with the anti L1 antibody or binding molecule of the invention, the patient is further treated with said chemotherapeutic drug or with said radiotherapy.

In the context of the present invention, it is envisaged to sensitize tumor cells of any cell type or to treat any tumorigenic disease. Preferably, the tumor cells or the tumorigenic disease are of a type selected from the group consisting of astrocytoma, oligodendroglioma, meningioma, neurofibroma, glioblastoma, ependymoma, Schwannoma, neurofibrosarcoma, medulloblastoma, melanoma, pancreatic cancer, prostate carcinoma, head and neck cancer, breast cancer, lung cancer, ovarian cancer, endometrial cancer, renal cancer, neuroblastomas, squamous cell carcinomas, medulloblastomas, hepatoma, colon cancer, and mesothelioma and epidermoid carcinoma.

Furthermore, it is preferred that the tumor cells are from an epithelial, tumor or the tumorigenic disease is an epithelial tumor, preferably wherein the epithelial tumor is pancreatic cancer, colon cancer, ovarian cancer or endometrial cancer.

In a preferred embodiment the antibody does not induce neuronal side effects when administered in a therapeutically effective amount.

As discussed above, the anti-L1 antibody or binding molecule are used for the preparation of a pharmaceutical composition.

In general, the pharmaceutical compositions of the present invention comprise a therapeutically effective amount of a therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

In a preferred embodiment, the composition is formulated, in accordance with routine procedures, as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water or saline for injection can be provided so that the ingredients may be mixed prior to administration.

The therapeutics of the invention can be formulated as neutral or salt forms. Pharmaceutically acceptable salts include those formed with free carboxyl groups such as those derived from hydrochloric, phosphoric, acetic, oxalic, tartaric acids, etc., those formed with free amine groups such as those derived from isopropylamine, triethylamine, 2-ethylamino ethanol, histidine, procaine, etc., and those derived from sodium, potassium, ammonium, calcium, and ferric hydroxides, etc.

The amount of the therapeutic of the invention, which will be effective in the treatment of a particular disorder or condition, will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems. In general, suppositories may contain active ingredient in the range of 0.5% to 10% by weight; oral formulations preferably contain 10% to 95% active ingredient.

Various delivery systems are known and can be used to administer a therapeutic of the invention, e.g., encapsulation in liposomes, microparticles, and microcapsules: use of recombinant cells capable of expressing the therapeutic, use of receptor-mediated endocytosis (e.g., Wu and Wu, 1987, J. Biol. Chem. 262:4429-4432); construction of a therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion, by bolus injection, by absorption through epithelial or mucocutaneous linings (e.g., oral, rectal and intestinal mucosa, etc.), and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the therapeutic can be delivered in a vesicle, in particular a liposome (Langer, 1990, Science 249:1527-1533), more particular a cationic liposome (WO 98140052).

In yet another embodiment, the therapeutic can be delivered via a controlled release system. In one embodiment, a pump may be used (Langer, supra). In yet another embodiment, a controlled release system can be placed in proximity of the therapeutic target, thus requiring only a fraction of the systemic dose.

Within the context of this aspect of the invention, the invention also includes a method for sensitizing tumor cells in a patient for the treatment with a chemotherapeutic drug or with radiotherapy, comprising administering to the patient an efficient amount of an anti-L1 antibody or binding molecule of the invention. All is embodiments described above also apply to this method of the invention.

Throughout the invention, the term "effective amount" means that a given molecule or compound is administered in an amount sufficient to obtain a desired therapeutic effect. In case that, throughout the invention, two compounds are administered in a therapeutic effective amount, this includes that one or each of the compounds is administered in a sub-therapeutic amount, i.e. that the amount of each compound on its own is not sufficient to provide a therapeutic effect, but that the combination of the compounds results in the desired therapeutic effect. However, it is also included within the present invention that each of the compounds on its own is administered in a therapeutically effective amount.

In another aspect of the invention, the invention relates to the use of the anti-L1 antibody or binding molecule of the invention for the preparation of a medicament for the treatment of tumor cells in a patient previously treated with a chemotherapeutic drug or with radiotherapy.

As mentioned above, the treatment of tumor cells with anti-L1 antibodies has already been described in WO 02/04952 and WO 06/013051, incorporated herein by reference.

In the context of the present invention, the term "previously treated" may include patients which have already been treated with a chemotherapeutic drug or with radiotherapy in the course of a separated regimen which has taken place e.g. within the last six or eight months.

In the course of tumor treatment with chemotherapeutic drugs or radiotherapy it is in most cases observed that after an initial response of the tumor to such therapy (tumor mass reduction or stabilization of the disease) the tumors start to progress again. Such progression usually starts upon weeks or months after such therapy. Typically these tumors are then resistant to further treatment with the previously applied chemotherapeutic drug and other treatment modalities are wanted. As described above it has been found that such resistant tumors express L1 and therefore become a target for anti-L1 antibodies.

Therefore, according to this embodiment of the invention, the term "previously treated" preferably means that the patient previously received such treatment, such treatment showed an initial effect and—at the time of therapy with the anti-L1 antibody or the binding molecule the tumor is progressing again.

Furthermore, the term "previously treated" may also be seen in a context where the L1 anti-L1 antibody or the binding molecule and the chemotherapeutic drug or radiotherapy are used within the same regimen, meaning that the treatments are given within one treatment schedule. In this context "in one treatment schedule" means that the treatment are applied at the same time, one after another or intermittently, but—in contrast to above—time distances between the individual treatments are short (within one week or within 2-4 days) and, if a treatment success is seen, one does not wait for tumor progression before the next treatment is applied.

Preferably, in this context, the invention includes the case where a patient is treated with a chemotherapeutic drug or with radiotherapy and subsequently, preferably within one week or less and more preferably within 2-4 days, a treatment with the anti-L1 antibody or the binding molecule of the invention is started. In a further preferred embodiment several cycles of chemotherapy or radiotherapy on one side and treatment with the anti-L1 antibody or the binding molecule are made, with intervals of preferably one week or less and more preferably within 2-4 days.

In a preferred embodiment, the patient is at least partially resistant to the treatment with said chemotherapeutic drug or with radiotherapy, an effect often observed in the course of said treatment types (see above).

In a further aspect, the invention relates to the use of the anti-L1 antibody or the binding molecule of the invention for the preparation of a medicament for the treatment of tumor cells in a patient at least partially resistant to treatment with a given chemotherapeutic drug or with radiotherapy.

In the context of the present invention, the term "resistant to treatment" means that the respective tumor cell does not react to the treatment with a chemotherapeutic drug or with radiotherapy in a complete manner. Rather, with respect to this tumor cell, treatment with said chemotherapeutic drug or radiotherapy is rather ineffective or even shows no effects.

In a further aspect of the invention, the invention relates to the use of the anti-L1 antibody or the binding molecule of the invention for the preparation of a medicament for the treatment of a tumorigenic disease, wherein the anti-L1 antibody or the binding molecule is administered in combination with a chemotherapeutic drug or with radiotherapy, preferably wherein the chemotherapeutic drug or the radiotherapy is administered prior to the anti-L1 antibody or binding molecule of the invention.

According to the invention, the term "treatment of tumorigenic disease" includes both the killing of tumor cells, the reduction of the proliferation of tumor cells (e.g. by at least 30%, at least 50% or at least 90%) as well as the complete inhibition of the proliferation of tumor cells. Furthermore, this term includes the prevention of a tumorigenic disease, e.g. by killing of cells that may or a prone to become a tumor cell in the future as well as the formation of metastases.

According to the invention, the terra "in combination with" includes any combined administration of the anti-L1 antibody or the binding molecule and the chemotherapeutic drug of radiotherapy. This may include the simultaneous application of the drugs or radiotherapy or, preferably, a separate administration. In case that a separate administration is envisaged, one would preferably ensure that a significant period of time would not expire between the time of delivery, such that the anti-L1 antibody or the binding molecule and the chemotherapeutic drug or radiotherapy would still be able to exert an advantageously combined effect on the cell. In such instances, it is preferred that one would contact the cell with both agents within about one week, preferably within about 4 days, more preferably within about 12-36 hours of each other.

The rational behind this aspect of the invention is that the administration of chemotherapeutic drugs or the treatment with radiotherapy leads to an increase of L1 expression on the surface of the tumor cells which in turn makes the tumor cells a better target for the anti-L1 antibody or the binding molecule.

Therefore, this aspect of the invention also encompasses treatment regimens where an the anti-L1 antibody or the binding molecule is administered in combination with the chemotherapeutic drug or radiotherapy in various treatment cycles wherein each cycle may be separated by a period of time without treatment which may last e.g. for two weeks and wherein each cycle may involve the repeated administration of the anti-L1 antibody or the binding molecule and/or the chemotherapeutic drug or radiotherapy. For example such treatment cycle may encompass the treatment with a chemotherapeutic drug or with radiotherapy, followed by e.g. the twice application of the anti-L1 antibody or the binding molecule within 2 days.

Throughout the invention, the skilled person will understand that the individual therapy to be applied will depend on the e.g. physical conditions of the patient or on the severity of the disease and will therefore have to be adjusted on a case to case basis.

Especially in the course of such repeated treatment cycles, it is also envisaged within the present invention that the anti-L1 antibody or the binding molecule is administered prior to the chemotherapeutic drug or the radiotherapy.

In the context of the above aspects of the invention, the invention also relates to a method for treating tumor cells in a patient previously treated with a chemotherapeutic drug or with radiotherapy, comprising administering to the patient a therapeutically effective amount of the anti-L1 antibody or binding molecule of the invention. Furthermore, the invention relates to a method for treating tumor cells in a patient at least partially resistant to treatment with a given chemotherapeutic drug or with radiotherapy, comprising administering to the patient a therapeutically effective amount of the anti-L1 antibody or binding molecule of the invention. Furthermore, the invention relates to a method for treating tumor cells in a patient, comprising administering to the patient a therapeutically effective amount of the anti-L1 antibody or binding molecule of the invention in combination with a chemotherapeutic drug or with radiotherapy. Furthermore, the invention relates to a method for treating tumor cells in a patient, comprising administering to the patient a therapeutically effective amount of the anti-L1 antibody or binding molecule of the invention.

The antibody of the invention may also be used in a method for a diagnostic method to determine the level of the L1 protein in body tissues or fluids.

With respect to these methods of the invention, all embodiments described above for the other uses or methods of the invention also apply.

The invention also relates to the antibody or the binding molecule of the invention for use as a medicament for the treatment of a tumorigenic disease or for sensitizing of tumor cells in a patient for the treatment with a chemotherapeutic drug or with radiotherapy.

In a preferred embodiment, said use exhibits further the features as defined for the uses of the invention.

The invention also relates to pharmaceutical compositions comprising the antibody or binding molecule of the invention. With respect to said pharmaceutical composition, all embodiments described above also apply.

The invention is further illustrated by the following figures and examples which are not intended to limit the scope of the invention.

LEGENDS TO FIGURES AND TABLES

FIG. 1

(A) FACS analysis of CHO, CHO-L1, SKOV3ip and OVMz cells. Cells were stained with the indicated mAbs (10 µg/ml) for 30 min, at 4° C. Followed by a secondary PE-conjugated mAb. (B) Western blot analysis. Cell lysates from CHO wt, CHO-L1, OVMz and SKOV3ip cells were transferred on a PVDF membrane and then incubated with the indicated mAb to L1 (1 µg/ml), followed by a POX-conjugated secondary mAb.

FIG. 2

(A) Effect of antibodies on Erk-phosphorylation in SKOV3ip cells. Cells were incubated for 24 h at 37° C. with the indicated purified antibodies to L1 (10 µg/ml) or isotype control IgG1. Cells were also treated with DMSO (vehicle), or the MEK-specific inhibitor PD59098. Cell lysates were examined for phosphorylation of Erk.

(B) Effect of antibodies on Eric phosphorylation in SKOV3ip cells. Fluorescent staining of antibody treated cells with a phospho-Erk specific antibody and an Alexa488-conjugated secondary mAb.

FIG. 3

Analysis of matrigel cell invasion. Antibody (10 μg/ml) treated SKOV3ip cells were seeded into a 4-well plate and allowed to invade into the matrigel for 20 h (5% $CO_2$; 37° C.).

FIG. 4

Differential gene expression in SKOV3ip cells. (A) SKOV3ip cells were transfected with L1-specific or scrambled siRNA and 72 h later mRNAs were isolated, transcribed to cDNA and used as template for qPCR (SYBRgreen analysis). (B) SKOV3ip cells were treated with the L1-9.3 mAb (10 μg/ml) or the control mAB IgG1 (10 μg/ml) and 96 h later mRNAs were isolated, transcribed to cDNA and analyzed by qPCR for the expression of the indicated genes (SYBRgreen analysis).

(C) Differential gene expression of residual tumor cells. mRNAs from residual tumors were isolated from antibody treated animals, transcribed into cDNA and analyzed by qPCR for the expression of the indicated genes.

FIG. 5

Tumor growth in nude mice. LacZ-tagged SKOV3ip cells were injected i.p. into nude mice and after tumor implantation animals were treated with the indicated L1 mAbs or control mAb EpCAM (Hea125). After 30 days the tumor volume was determined and is given as the ratio between X-Gal stained tumor mass and the total situs. 6 animals were analyzed per group.

FIG. 6

(A) Western blot analysis of L1-V5 constructs. Supernatant of transfected Sf9 insect cells were received from Ricardo Gouveia and analyzed by Western blot using L1-9.3 mAb and reprobed by anti-V5 mAb. (B) Western blot analysis of L1-FC constructs. L1-FC constructs were transfected into Cos-7 cells using Jet PEI™ transfection reagent as described. After 3 days supernatants were purified using SepharoseA and analyzed by Western blot using L1-9.3 mAb.

FIG. 7

Homophilic cell adhesion assay. (A) The binding of J558-L1 cells was analyzed by bright field microscopy. One example of each treatment is shown here. In the red box coating with L1-Fc (10 μg/ml) is highlighted and in the black box the both controls, fibronectin (10 μg/ml) and BSA, are shown. (B) The graph shows the mean±SD of bound cells after the indicated antibody or control treatment.

FIG. 8

The antibody light chain and heavy chain DNA sequences used to construct the humanized antibodies are provided in FIGS. 8a (SEQ ID NOS 17-21, respectively, in order of appearance) and 8b (SEQ ID NOS 22-25, respectively, in order of appearance) respectively.

FIG. 9

Amino acid sequences of the murine L1__9.3 scFv (SEC) ID NO: 26) (a) and the humanized L1__9.3Hu (SEQ ID NO: 27) (b) and L1__9.3Hu3 scFvs (SEQ ID NO: 28) (c).

FIG. 10

DNA and amino acid sequences of the expressed portions of L1__9.3 (SEQ ID NOS 29-30, respectively) (a), L1-9.3Hu (SEQ ID NOS 31-32, respectively) (b) and L1__9.3Hu3 scFv (SEQ ID NOS 33-34, respectively) (c) constructs.

FIG. 11

Binding of the L1__9.3, L1-9.3Hu and L1__9.3Hu3 scFvs to the human L1 cancer antigen. Rows A, B and C are coated with L1 and rows D, E and F are coated with streptavidin. The blue colour in the wells indicates binding of the individual scFv to the L1 on the plate. The lack of colour in the streptavidin coated rows shows that the single chain antibodies are specifically binding to L1

FIG. 12

Genomic sequences of the variable domains of the monoclonal antibody 9.3 a) Sequence of the kappa chain variable region (SEQ ID NO: 35) (dotted lines: CDR1, dashed lines: CDR2, underlined: CDR3)

b) Sequence of the heavy chain variable region (SEQ ID NO: 36) (dotted lines: CDR1, dashed lines: CDR2, underlined: CDR3)

FIG. 13

A) Human PBMC and L1-positive OVMZ tumor cells were incubated with L1-9.3 mAb for 24 h and the amount of bound antibody was determined by FACS analysis.

B) The dissociation constants $K_D$ were estimated from the regression curves using the concentration at half-maximal binding.

FIG. 14

L1-9.3 has no effect on the release of cytokines by resting and activated human PBMC. Cytokine levels of resting and OKT3-activated PBMC from three different donors were determined after an incubation for 24 h in presence or absence of 20 μg/ml L1-9.3. Ionomycin/PMA and LPS were used as stimulation controls. Results for IFN-γ (A) and TNF-α (B) are shown.

FIG. 15

L1-9.3 does not induce T cell proliferation and has no effect on OKT3-induced T cell proliferation. Proliferation of OKT3-activated PBMC from two different donors was determined in presence or absence of 20 μg/ml L1-9.3 using a BrdU incorporation assay 48 h post stimulation. There was no difference, whether the antibody was added prior, in parallel or after stimulation with 75 ng/ml OKT3. L1-9.3 by itself did not result in T cell activation.

FIG. 16

L1-9-3 was unaffected by deglycosylation of L1. The Western blot staining of L1 in untreated and deglycosylated cell lysate is shown using several different anti-L1 mAbs. The tested antibodies can be divided into three classes in respect to their glycosylation-dependency: First class (unaffected by glycosylation): L1-9.3. Second class (binding in WB was negatively affected by deglycosylation): 11A, 14.10, OV52.24 and OV549.20. Third class (binding in WB was positively affected by deglycosylation): 35.9 and 38.12.

FIG. 17

The figure shows in vivo binding of intravenously applied L1-9.3 to collecting ducts of the kidney. In vivo binding was only detectable using the amplification system CSA (FIG. 17A), while by using the conventional ABC-method, no signal was visible (FIG. 17B). Hence, L1-9.3 was detected in a range of 30-300 pmol in the tissue (L1-9.3 concentration is presumably higher than 5 ng/ml and below 50 ng/ml). Negative control did not show staining, thus, unspecific staining can be excluded (FIG. 17C). The staining pattern of in vivo bound L1-9.3 (FIG. 17A) corresponds to the L1 expression pattern in the kidney when directly staining tissue sections with L1-9.3 (FIG. 17D).

FIG. 18

FACS Analysis of Humanized L1-9.3 mAbs

Flow cytometry analysis of SKOV3ip pcDNA3.1 luciferase cells. Cells were stained with the indicated humanized mAbs (10 μg/ml) for 30 min 4° C., followed by a secondary PE-conjugated mAb.

FIG. 19

Mouse SKOV3ip Xenograft-Model

7*10⁶ SKOV3ip pcDNA3.1 luciferase cells were injected intraperitoneal into 6 weeks old CD1 nu/nu female mice. After 24 h mice were randomized in groups of 10 mice. Each group of mice was three times weekly injected with 300 μg either mAb L1-chi9.3, mAbL1-hu3 or PBS intraperitoneally.

On day 33 mice were imaged (FIG. 2). Tumor volume was determined using the XENOGEN IVIS 200 System. In brief, mice were anesthetised and injected with 100 μl Luciferin D (3 μg/mouse) intraperitoneally. Afterwards, luciferase activity of the tumor cells was measured by detecting light emission. The tumor volume is shown as photon per second (total flux). Statistical analysis was done using the student's t-test.

FIG. 20

In Vivo Total Tumor Mass

After 36 days mice were sacrificed and the tumor mass was determined. Tumor growth is given as a ratio of tumor mass to bodyweight. (A individual mice, B mean value). Statistical analysis was done using the student's t-test. Thus, the treatment of immunodeficient mice with L1 9.3 antibody could be reproduced with chimarised and humanized forms of the L1 9.3 mAb.

FIG. 21

PT45-P1res cells were either left untreated (w/o) or were treated with 20 μg/mL gemcitabone (A) or etoposide (B) in the absence (w/o) or presence of either 1 or 10 μg/mL anti L1CAM antibody 9.3 or 1 or 10 μg/mL isotype matched control antibody. After 24 hours, cells were analysed by caspase-3/-7 assay. Means±SD from three independent experiments are shown. * indicates p<0.05.

FIG. 22

Colo357 cells were either left untreated (w/o) or were treated with 20 μg/mL gemcitabone (A) or etoposide (B) in the absence (w/o) or presence of either 1 or 10 μg/mL anti L1 CAM antibody 9.3 or 1 or 10 μg/mL isotype matched control antibody. After 24 hours, cells were analysed by caspase-3/-7 assay. Means±SD from three independent experiments are shown. * indicates p<0.05.

TABLE 1

The table shows a summary of antibodies tested in the indicated assays.

EXAMPLES

1. Example 1

1.1 Summary of Example 1

The L1 adhesion molecule (L1-CAM) is a transmembrane cell adhesion molecule involved in cell migration and axon guidance in the developing nervous system. L1 is also over-expressed in ovarian and endometrial carcinomas. Here L1 expression is associated with poor prognosis. In carcinoma cell lines, L1 over-expression augments cell motility, tumor growth in mice and induces expression of Erk-dependent genes. Here we show that treatment with antibodies to L1 abrogates Erk-activation, blocks cell invasion to matrigel and decreases tumor growth in nude mice. In cells treated with L1 antibodies the induction of Erk-dependent genes such as HOX A9, β3 integrin and IER 3 are reversed in vitro and in vivo. In this report, we demonstrate that the antibody L1-9.3 is the best therapeutic antibody of all tested L1 antibodies. In all cases L1-9.3 showed the best results concerning the invasive phenotype or therapeutic effect on tumor growth. We could show that L1-9.3 binds to the first Ig-like domain of L1 and can block the L1-L1 homophilic binding. The blocking of homophilic binding was only observed with L1-9.3. We conclude, that L1-9.3 is superior in therapy as it combines two functions: it blocks erk activation and interferes with the binding function of L1.

1.2 Results of Example 1

1.2.1 FACS Analysis of the New L1 Antibodies

Using immunization with a recombinant L1-Fc fusion protein, we generated novel L1 antibodies L1-9.3, L1-14.10, L1-35.9 and L1-38.12. To elucidate the specificity for L1 the new L1 mAbs were tested these antibodies on the endogenous L1 expressing ovarian carcinoma cell lines OVMz and SKOV3ip and the Chinese hamster ovary cells CHO and stably transduced CHO-L1 cells by fluorescent staining (FIG. 1A) and Western blot analysis (FIG. 1B). All tested antibodies showed a positive staining of L1 in CHO-L1 cells (FIG. 1A). The staining pattern for the OVMz and the SKOV3ip cells was different for the antibodies. Interestingly, the L1-9.3 antibody showed bright staining of both ovarian carcinoma cell lines OVMz and SKOV3ip, whereas the L1-14.10 showed a very weak staining (FIG. 1A). The two L1 antibodies L1-35.9 and L1-38.12 could not bind to the endogenous L1 of these cells (FIG. 1A). As expected, no staining for L1 could be observed in CHO cells which we used as negative control. All new antibodies detected the full-length L1 in CHO-L1, OVMz and SKOV3ip cell lysates by Western blot analysis. The L1-negative CHO cells served again as negative control.

1.2.2 the Erk Phosphorylation is Decreased after Antibody Treatment

A recent report has shown that expression of L1 in cooperation with serum-derived growth factors lead to sustained Erk-activation and the induction of Erk-dependent genes (Silletti et al, 2004). We investigated if the suppressive effect of L1-antibodies might be due to interference with L1-mediated gene regulation. Therefore we examined the mode of action of L1 antibodies using SKOV3ip cells. The mAbs L1-11A, L1-9.3 and L1-14.10 efficiently blocked Erk-phosphorylation (FIG. 2A) in vitro. There was no inhibition with isotype matched control mAb, DMSO as vehicle or the L1 antibody L1-38.12 (FIG. 2A) that can bind only the neural isoform of L1. Fluorescent analysis with the phospho-specific Erk antibody confirmed a clear reduction of activated Erk. A depletion from the nucleus in L1-mAb treated cells (L1-11A, L1-9.3 and L1-14.10) could also be observed (FIG. 2B).

1.2.3 Antibody Treatment with L1-Antibodies Reduced Cell Invasion

Figure 3:
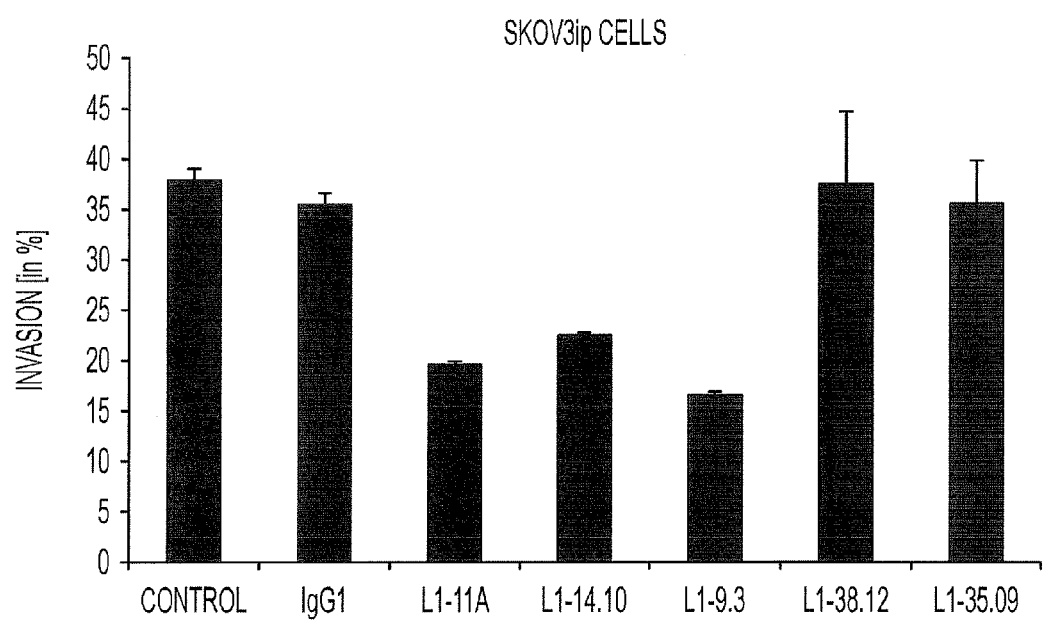

It has been demonstrated before that treatment with an antibody to L1 (L1-11A) reduced the haptotactic cell migration on fibronectin and the matrigel invasion of different cell lines (Arlt et al, 2006). We compared the invasion capacity of SKOV3ip cells treated with the different L1 antibodies. The antibodies L1-11A, L1-14.10 and especially L1-9.3 reduced the invasion of the SKOV3ip (FIG. 3). In sharp contrast, cells treated with the antibodies L1-35.9 or L1-38.12 did not show a reduction of invasion (FIG. 3).

1.2.4 Antibodies to L1 Affect Gene Expression In Vitro and In Vivo

We further examined whether antibodies to L1 affect the gene expression profile in SKOV3ip cells in vitro in a similar fashion as observed for siRNA-mediated depletion of L1 (FIG. 4A). Indeed, qRT-PCR analysis of cells treated with L1-9.3 or L1-11A versus control antibody showed significant changes in the expression of L1-regulated genes such as β3 integrin, the transcription factors HOXA9 and the apoptosis-related genes IER 3 and STK 39 (FIG. 4A). The same set of genes was down regulated in SKOV3ip cells transduced with a L1-specific siRNA (FIG. 4B).

We tested whether mAb L1-9.3 could also influence the gene expression profile of SKOV3ip cells in vivo similar to that observed in vitro. To this end, mRNA from residual tumors of L1-9.3 treated mice or IgG control treated mice were isolated and subjected to qRT-PCR analysis. L1-93 treatment led to significant regulation of L1-dependent genes as demonstrated for HOXA9, β3 integrin and IER 3 (FIG. 4C).

1.2.5 Analysis of Tumorigenicity in Nude Mice

Figure 5:
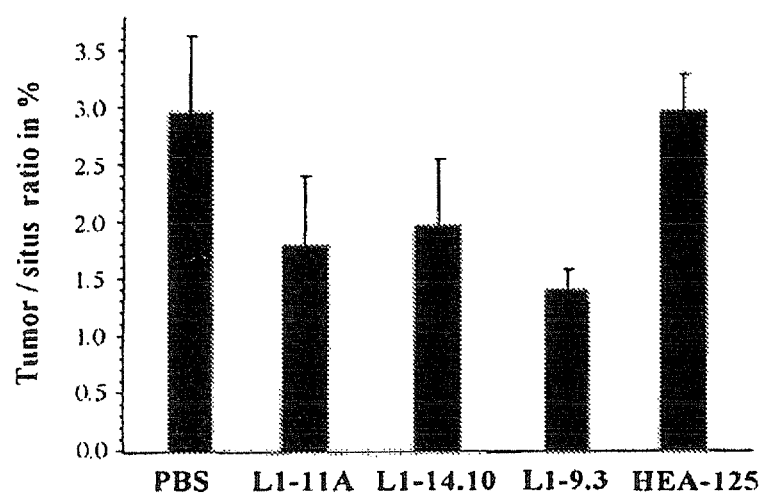

Next, we investigated whether the intraperitoneal growth of SKOV3ip in mice could be inhibited by treatment with the mAbs L1-11A, L1-9.3 or L1-14.10. SKOV3ip-lacZ cells were injected into the peritoneal cavity of female nude mice 2 days before the onset of therapy. Biweekly i.p. treatments were done using the 10 mg/kg antibody concentration. Control mice were treated with PBS or HEA125 (anti EpCAM) as a control antibody (biweekly 10 mg/kg i.p.). In all anti-L1 mAb treatment groups, a substantial decrease in the amount of tumor mass was visible compared with PBS or the control antibody HEA-125 (FIG. 5). Compared with the control, all anti-L1 mAbs led to a dose-dependent reduction of i.p. tumor burden [L1-11A (10 mg/kg), −40%; L1-14.10 (10 mg/kg), −30%; L1-9.3 (10 mg/kg), −450%; FIG. 5]. Tumor reduction in the group treated with the L1-9.3 (10 mg/kg) was statistically significant ($P_{L1-9.3(10\ mg/kg)}=0.004$) compared with the PBS control. Mice treated with the HEA125 control antibody revealed no detectable reduction of SKOV3ip-lacZ i.p. tumor burden compared with the PBS-treated group (FIG. 5), although EpCAM is present on the SKOV3ip cells and HEA125 can bind to the tumor cells. No side effects or severe toxicity of L1⁻mAbs L1-11A, L1-9.3 or L1-14.10 treatment was observed during the whole course of treatment.

Thus, treatment with antibodies to L1 reduced the tumor growth SKOV3ip cells (FIG. 5) suggesting that antibodies to L1 can regulate gene expression but also affect in vivo tumor growth.

1.2.6 Biacore Studie of the New L1 Antibodies

This study was performed by Avidex (Oxford) as described in Example 6. Table 1 summarizes these results concerning the binding kinetics of the new L1 antibodies (ka, kd and KD).

1.2.7 Epitop-Mopping of L1-9.3 Binding Site

An important factor for the characterization of novel L1 antibodies is to examine their binding sites in L1. Therefore, we constructed a variety of L1-Fc fusion proteins covering different parts of the molecule. PCR products were amplified coding different length of L1 ectodomain regions. These constructs were cloned into the pIg vector, and expressed as Fc-fusion proteins. After purification, products were used for Western blot analysis. For comparing the results, we analyzed other recombinant L1 protein fragments (obtained from Ricardo Gouveia, Oeiras, Portugal). L1-9.3 was found to bind to first Ig domain of L1 (FIG. 6). L1-14.10 binds in the third Ig domain whereas L1-11A binds between the FN3-5 site (FIG. 6).

1.2.8 mAB L1-9.3 Blocks L1-1.1 Homophilic Binding

We asked if the L1 antibodies could interfere with the homophilic binding function of L1. To address this question, we used a cell adhesion assay in which L1-transfected cells are allowed to bind to immobilized L1. After initial coating of glass slides with a recombinant L1-Fc fusion protein, fibronectin for positive control (to which cells bind in an integrin dependent mailer) or BSA as a negative control, we incubated J558-L1 cells with L1-11A, L1-9.3 or L1-14.10 antibody. For control, we used an IgG-control, PBS or an antibody to CD24 (SWA 11). The mAb L1-9.3 could completely block the L1-L1 homophilic binding, whereas all other tested antibodies could not interfere with the homophilic binding capacity. None of the antibodies interfered with the binding to fibronectin (data not shown).

1.3 Materials and Methods 1.3.1 Cell Lines and Cell Culture

The human ovarian carcinoma cell lines SKOV3ip (kindly provided by Ellen Vitetta, University of Texas, Dallas, Tex.) and OVMz were grown in DMEM (Biochrom, Berlin, Germany) with 10% FCS under cell culture conditions (5% $CO_2$, 95% relative humidity, 37° C.). For identification and quantification of tumor mass, the SKOV3ip cells were stably transduced with a lacZ-encoding retroviral vector (GeneSuppressor Retroviral System, Biocarta, Hamburg, Germany). The Chinese hamster ovary cell line CHO stably expressing human L1 (–hL1) were established by transfection with superfect (Stratagene, Heidelberg, Germany) and selection for L1 expression with mAb L1-11A and magnetic beads (Myltenyi Biotec, Bergisch Gladbach, Germany) or sorting with FACS Calibur. All cells were cultivated in DMEM supplemented with 10% FCS at 37° C., 5% $CO_2$ and 100% humidity. Human L1 encoding plasmids and J558-L1 cells were obtained from Dr. Vance Lemmon (University of Miami, Miami, Fla., USA).

1.3.2 Antibodies

HEA-125, a mouse IgG1 directed against EpCAM, was described before and binds to all human adenocarcinomas (Moldenhauer et al., 1987). Monoclonal antibody L1-14.10 (Huszar et al., 2006), L1-9.3, L1-35.9 and L1-38.12 were obtained after immunization of mice with human L1-Fc protein comprising the ectodomain of L1 (Oleszewski et al., 1999). Goat anti-mouse IgG was affinity purified and absorbed to human serum proteins (Zymed Laboratories, Inc., San Francisco, Calif.).

1.3.3 Biochemical Analysis

SDS-PAGE and transfer of separated proteins to Immobilon membranes using semi-dry blotting were described before (Gutwein et al., 2000). After blocking with 5% skim milk in TBS or 1% BSA in TBS/0.1% Tween-20, the blots were developed with the respective primary antibody followed by peroxidase conjugated secondary antibody and ECL detection.

1.3.4 FACS Analysis

The surface staining of cells with saturating amounts of mAbs, either hybridoma supernatants or purified antibodies, and PE-conjugated goat antibodies to mouse Ig (Dianova, Hamburg, Germany) has been described elsewhere (Ebeling et al., 1996). Stained cells were analyzed with a FACScan (Becton Dickinson).

1.3.5 Immunofluorescence

For immunofluorescent staining, cells were grown on coverslips, treated for 10 min with pervanadate and fixed for 20 min with 4% paraformaldehyde/PBS at room temperature. Cells were washed in PBS and permeabilized with 0.1% NP-40 in PBS containing 5% goat serum for 15 mm at room temperature. Cells were then incubated for 1 hour with first antibody (phospho-specific Erk1/2). After 3 washing steps with PBS cells were incubated 30 min in the dark to a second Alexa488-conjugated goat anti-mouse IgG. After washing the cells twice with PBS, stained cells were mounted on glass slides and examined with an epifluorescence microscope (Axioplan-2; Zeiss, Oberkochem).

1.3.6 Invasion Assay

Tumor cell invasion in vitro was determined in a double-filter assay as described previously in Erkell et al. (1988). Briefly, a Matrigel was layered between two filters, a lower 5 µm pore nitrocellulose filter and an upper 8 µm pore polycarbonate filter. Following incubation of $10^5$ cells with the filter sandwich for 20 h in 1 nil medium, the sandwich was fixed and the filters separated and stained with DAPI. Cells present in the gel on the lower filter were counted, and cell invasion was expressed as the ration of the cell number on the lower filter to the total number of cells present on both filters.

1.3.7 Quantitative PCR

For qPCR the cDNA was purified on Microspin G-50 columns (GE Healthcare, München, Germany) and quantitated by NanoDrop spectrophotometer (ND-1000. Kisker-Biotechnology, Steinfurt, Germany). Primers for qPCR were designed with the DNA Star Program and were produced by MWG (Ebersberg, Germany). β-actin was used as an internal standard. The PCR reaction was performed with the SYBRgreen mastermix (Applied biosystems, Darmstadt, Germany).

1.3.8 Cell Binding Assay

Cell binding assays to L1-Fc or fibronectin are described in detail in Oleszewski et al (JCB 2000).

1.3.9 Tumor Model and Therapy

Pathogen-free, female athymic CD1 nu/nu mice (7-9 weeks old; 20 g on average; Charles River) were inoculated with $5 \times 10^6$ human lacZ-tagged ovarian carcinoma cells (SKOV3ip-lacZ) into the peritoneal cavity at day 0, leading to i.p. tumor formation within 5 weeks. Anti-L1 mAbs were diluted in sterile PBS to the concentration needed for treatment. Tumor-bearing mice were treated i.p. twice weekly with a 300 µL solution of the respective dosage (10 mg/kg per application, respectively), vehicle (PBS), or Hea125 antibody control. Antibody treatments started from day 3 after tumor cell injection to give the tumor cells time to attach to the inner side of the abdominal wall and the surfaces of the i.p. organs. At autopsy (day 38), to ascites was sampled from all mice and the volume was determined. All i.p. organs (including tumor mass), the abdominal wall, and the diaphragm were removed, stained with β-galactosidase substrate (X-gal; Roche-Diagnostics, Penzberg, Germany), photographed, and weighed. The indigo blue tumor mass between the organs, on the diaphragm and the inner site of the abdominal wall, was removed and weighed alone. The relative tumor burden in each mouse was calculated by dividing tumor mass weight by total situs weight.

2. Example 2

Humanization of the Anti-L1 Murine Antibody L1_93

In order to humanize the murine anti-L1 antibody L1__9.3, the genes of human v-kappa 1 (humκ1), and variable heavy chain family III (humIII) were utilised as the acceptor sequences. The numbering system used herein for these genes is adopted from Wu and Kabat (Kabat, E. A, Wu, T. T., Perry, H M, Gottesman, K S and Foeller, C (1992) *Sequences of proteins of immunological interest*, Diane Books Publishing company). The murine L1__9.3 antibody light and heavy chain amino acid sequences were aligned against the amino acid sequences of the humκ1 light chain and the humIII heavy chain respectively. Two humanized L1__9.3 antibodies (L1__9.3Hu and L1__9.3Hu3) were generated by replacing the six CDRs of the human antibody with the corresponding CDRs from the murine L1__9.3 antibody.

Locations of the Six Complementarity Determining Regions (CDRs)

| Loop | Kabat numbering scheme |
| --- | --- |
| LCDR1 | L24-L34 |
| LCDR2 | L50-L56 |
| LCDR3 | L89-L97 |
| HCDR1 | H31-H35B |
| HCDR2 | H50-H65 |
| HCDR3 | H93-H101 |

A number of framework residues of the murine L1__9.3 antibody were transferred to the humanized L1__9.3 antibodies:

Version 1 (L1__9.3Hu) humanized antibody—heavy chain residue numbers 6, 23, 27, 30, 43, 49, 71, 73, 76, 78 and 94, and light chain residue number 100 were transferred from the murine L1__9.3 antibody and light chain residue number 73 was replaced with the corresponding (Phe) found at this position in the human REI antibody light chain.

Version 2 (L1__9.3Hu3) humanized antibody—heavy chain residue numbers 6, 23, 27, 30, 71, 73, and 94, and light chain residue number 100 were transferred from the murine L1__9.3 antibody.

DNA sequences encoding single-chain variable fragment (scFv) analogues of the murine L1__9.3 antibody and the two humanised versions of this antibody (L1__9.3Hu, and L1__9.3Hu3) for expression in *E. coli* were then generated. All of these scFvs contain the same linker (TSGPGDGGKG-GPGKGPGGEGTKGTGPGG (SEQ ID NO: 12)). The scFv genes were synthesized by GeneArt AG, Germany.

The antibody light chain and heavy chain DNA sequences used to construct the humanized antibodies are provided in FIGS. 8a and 8b respectively.

FIGS. 9a-9c provide the amino acid sequences of the murine L1__9.3 scFv and the humanized L1__9.3Hu and L19.3Hu3 scFvs respectively.

3. Example 3

Cloning of DNA Encoding the L1__9.3, L1-9.3Hu and L1__9.3Hu3 scFvs into *E. coli* Periplasmic Expression Vectors and Transformation of *E. coli* with these Vectors Periplasmic expressed of scFvs is beneficial for a number of reasons. Firstly, such scFvs leak into the bacterial supernatant and from there can conveniently be assayed for binding to their cognate antigen (The L1 cancer antigen in this case). Secondly, periplasmic expression allows for purification of soluble active scFvs.

The DNA sequences encoding the L1__9.3, L1-9.3Hu and L1__9.3Hu3 scFvs as synthesized by GeneArt AG, Germany were not supplied in an *E. coli* periplasmic expression vector. Therefore, these DNA sequences where cloned into an *E. coli* periplasmic expression vector using the following methods.

The DNA encoding the synthesized scFvs were PCR rescued with the following primer pairs using standard PCR conditions and reagents:

| scFv | Primer pair |
| --- | --- |
| L1__9.3 | Yol811 and Yol812 |
| L1-9.3Hu | Yol813 and Yol814 |
| L1__9.3Hu3 | Yol813 and Yol814 |

The primer sequences are shown below.

(SEQ ID NO: 13)
Yol811
AGCCGGCCATGGCCGATATTCAGATGACCCAGAC (SEQ ID NO: 14)
Yol812
TCTATGCAGCGGCGGCACCGCCGCTGCTCACGGTAACGCTG (SEQ ID NO: 15)
Yol813
AGCCGGCCATGGCCGATATTCAGATGACCCAGAG (SEQ ID NO: 16)
Yol814
TCTATGCAGCGGCCGCACCGCCGCTGCTCACGGTAACCAGGGTG

The PCR products were run on a 1.6% agarose gel and bands of the correct size excised and purified. The PCR products were double digested with Nco1 and Not1 restriction enzymes under standard conditions followed by re-purification. The PCR products were ligated into an IPTG inducible periplasmic expression vector which contained:
a pelB leader sequence to direct the encoded polypeptides to the periplasm where this leader sequence is then cleaved off
Nco1/Not1 cloning sites
the human antibody kappa chain constant region The ligated vectors were transformed into *E. coli* TG1 cells and plated on of 2xTY agar (Bacto Trypton 16 g/L, yeast extract 10 g/L, 15 g/L bactoagar and NaCl 5 g/L) supplemented with 100 µg/ml ampicillin and 2% glucose. The DNA and amino acid sequences of the expressed portions of L1_9.3, L1-9.3Hu and L1_9.3Hu3 scFv constructs are shown in FIGS. 10a, 10b and 10c respectively.

4. Example 4

Expression of L1_9.3, L1-9.3Hu and L1_9.3Hu3 Single-Chain Antibodies in *E. coli*

The polypeptides expressed by these vectors include the human antibody c kappa constant region fused to the C termini of the scFvs. These c kappa constant chain containing constructs are referred to herein as single chain antibodies.

Eight *E. coli* clones for each single chain antibody construct, L1_9.3, L1_9.3Hu, and L1_9Hu3, (24 clones in total) were picked into separate wells of a 96 well plate containing 300 µl of 2xTY (Bacto Trypton 16 g/L, yeast extract 10 g/L and NaCl 5 g/L) supplemented with 100 µg/ml ampicillin and 2% glucose. Each well has a 1 ml volume. The cultures were grown with shaking (200 rpm) at 37° C. until the cultures reached an $OD_{600}$ of approximately 0.5. The 96 well plates were then spun down at 3200 rpm for 10 min and the supernatant was aspirated and discarded. The bacterial pellets were resuspended in fresh 2XTY 400 µl supplemented with 100 µg/ml ampicillin and 1 mM IPTG to induce expression of the single chain antibodies. The cultures were shaken at 204 rpm overnight at 25° C.

The following day the 96 well plate was spun down at 3200 rpm for 10 min to pellet the cells. The supernatant containing the expressed L1 single chain antibodies was kept for ELISA analysis.

5. Example 5

ELISA Assay of Binding of the L1_9.3, 13-9.3Hu and L1_9.3Hu3 scFvs to Human L1 Cancer Antigen This ELISA assay was carried out in order to confirm that the humanisation process had not lead to a loss of antibody binding to the L1 cancer antigen and to identify which of the clones picked correctly expressed the single chain antibody constructs.

Three rows of a 96 well plate were coated with 100 µl L1 antigen comprising the extracellolar domain of the L1 protein fused to an Fc fragment (5 µg/ml) in PBS for 1 hr at room temperature. A further three rows were coated with streptavidin (5 µg/ml) in PBS as a control.

The wells were washed three times with 370 µl of PBS and blocked with 3% milk powder in PBS for 1 hr at room temperature.

50 µl of each overnight bacterial supernatant was mixed with 50 µl of 6% milk powder in PBS for 1 hour.

The blocked ELISA plate was washed twice with PBS as described above and the blocked supernatants containing single chain antibody were added and incubated for 1 hp at room temperature.

The 96 well plate was washed four times with PBS 0.1% tween followed by the addition of 100 µl of anti-human kappa light chains bound and free antibody HRP conjugate (Sigma A7164) 1:5000 dilution in PBS 1% BSA. The conjugate was incubated for 1 hr at room temperature followed by five washes with PBS 0.1% tween.

The ELISA was developed by the addition of TMB 2-Component Microwell Peroxidase Substrate Kit (Kirkegaard and Perry Laboratories Inc., USA) according to the manufacturer's protocol. An image of the ELISA plate is shown in FIG. 4. At least four L1 binding clones have been observed for each of three single chain antibody versions. These L1 binding single chain antibody clones do not bind to streptavidin.

Figure 11:
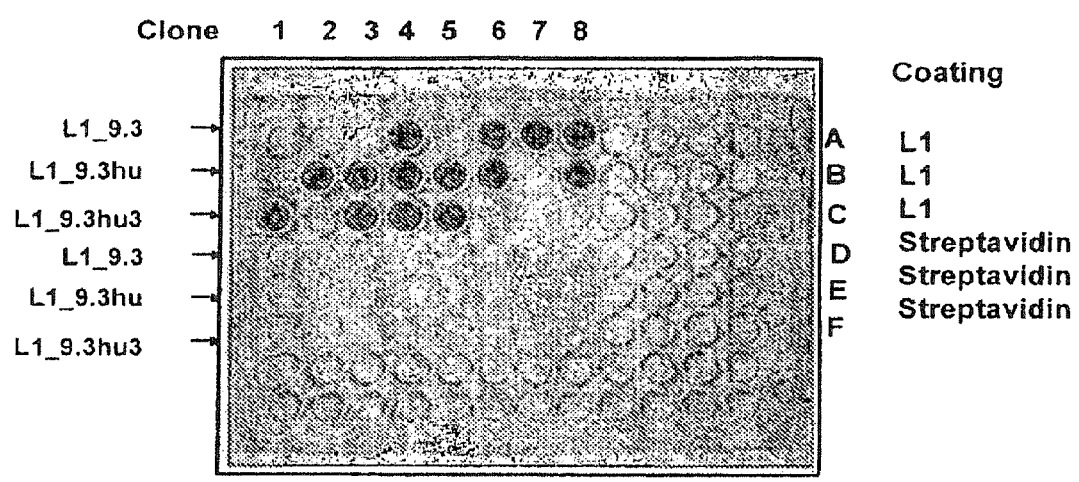

FIG. 11 shows the binding of the L1_9.3, L1-9.3Hu and L1_9.3Hu3 scFvs to the human L1 cancer antigen. Rows A, B and C are coated with L1 and rows D, E and F are coated with streptavidin. The blue colour in the wells indicates binding of the individual scFv to the L1 on the plate. The lack of colour in the streptavidin coated rows shows that the single chain antibodies are specifically binding to L1.

6. Example 6

Determination of Binding Affinity

Mouse antibody L1-9.3 and humanised antibody L1-hu3 were assayed by Biacore analysis (Biacore AB, Uppsala, Sweden) to determine binding kinetics.

A BIAcore CM5 sensor chip was activated with EDC/NHS and purified recombinant L1-Fc extracellular fragment (515 µg/ml in PBS) was coupled to the CM5 sensor chip to between 200 and 3000 RU. The remaining active sites were blocked by ethanolamine/HCl. Antibody binding was measured by adding antibody at concentrations from 6 to 3333 nM at a flow rate of 10 ul/min using the Kinject function. The chip was regenerated with 10 mM Glycine pH2.0 with 500 mM NaCl to remove the bound antibodies.

The binding curves were fit to a Langmuir binding model using BIA evaluation software (Biacore AB, Uppsala, Sweden). Determined KD values are shown in Table 2.

TABLE 2

Table 2: The humanized variant L1-hu3 displays a similar high target affinity as the parent antibody L1-9.3.

| Antibody | L1-9.3 | L1-hu3 |
|---|---|---|
| Ka [1/Ms] | $2.6 \times 10^5$ | $8.0 \times 10^5$ |
| Kd [1/s] | $2.2 \times 10^{-5}$ | $6.5 \times 10^{-5}$ |
| KD [M] | $8.5 \times 10^{-11}$ | $8.1 \times 10^{-11}$ |

7. Example 7

Antibody Binding to PBMCs and Cancer Cells

PBMC were obtained by density gradient centrifugation from EDTA whole blood of healthy human donors. Cultured OVMZ tumor cells were harvested by trypsination. $1 \times 10^5$ cells/well (75 µl) were seeded into FACS tubes. Dilutions of L1-9.3 mAb were prepared in culture medium with 10 mM EDTA and 75 µl/well of L1-mAb dilution were added, to PBMCs and OVMZ cells to result in final concentrations between $6.6 \times 10^{-13}$ to $6.6 \times 10^{-8}$ Mol. Subsequently cells were incubated over night (~24 h) at 37° C./5% $CO_2$ in an incubator. Cells were washed directly in FACS tubes using 2 ml of FACS buffer followed by centrifugation at 300 g/5 min/4° C. The supernatant was removed by pipetting. For staining, a PE-labelled donkey anti-mouse secondary antibody (Dako) was added at a volume of 150 µl/well followed by incubation for 30 min at 4° C. Washing steps were repeated as above and cells were fixed in 200 µl PBS/1% formaldehyde. Sample mean fluorescence was then measured by FACS analysis.

Figure 13:
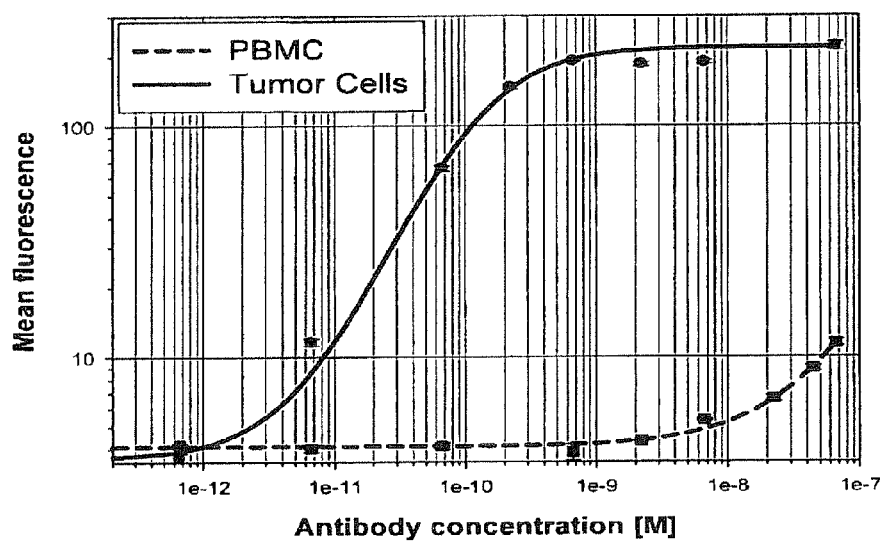

As shown in FIG. 13, L1-9.3 mAb displays a strongly reduced affinity to L1 on PBMC compared to tumor L1. L1-9.3 binding to PBMC was detected in the nanomolar range (dashed line), while binding to tumor cells could be observed at picomolar concentrations (solid line). B) The dissociation constants $K_D$ were estimated from the regression curves using the concentration at half-maximal binding. $K_D$ of L1-9.3 on PBMC was at least 400-fold lower than on tumor cells.

8. Example 8

Determination of Cytokine Release

PBMC were obtained by density gradient centrifugation from citrate whole blood of healthy human donors. Cells were resuspended in RPMI 1640/5% human serum/5 ml NEAA/5 ml L-Glutamin/5 ml Natrium-Pyruvat. $1 \times 10^5$ cells per 100 µl were seeded in round bottom 96 well plates. In a second step, 100 µl medium containing LPS (10 ng/ml), L1-9.3 mAb (20 µg/ml), OKT3 mAB (ebioscience) (75 ng/ml) or Ionomycin/PMA (1 µg/ml/5 ng/ml) were added in triplicates followed by an incubation for 24 h at 37° C., 5% $CO_2$. As negative control, untreated PBMC were used. After 24 h, levels of the cytokines interferone-gamma and tumor necrosis factor were measured by FACS analysis using the CBA-Cytokin-Flex-Sets (BD) according to manufacturers information.

The resulting cytokine levels are depicted in FIG. 14. In contrast to OKT3 mAB, Ionomycin/PMA, and LPS, L1-9.3 did not significantly increase the TNF or IFN-gamma release by PBMCs.

9. Example 9

T-Cell Proliferation Assay

PBMC were obtained by density gradient centrifugation from citrate whole blood of two healthy human donors. $1 \times 10^5$ cells per well were seeded in flat bottom 96 well plates. In a second step, 100 µl medium containing either L1-9.3 mAb (20 µg/ml) and OKT3 (ebioscience, 75 ng/ml) or L1-9.3 mAb (20 µg/ml) or OKT3 (75 ng/ml) was added in triplicates. After 1 h, the latter two were supplemented with OKT3 or L1-9.3, respectively. To exclude any antibody related activation, PBMC with or without L1-9.3 were incubated in absence of OKT3. Following an incubation for 24 h at 37° C., 5% $CO_2$ T cell proliferation was assessed using a BrdU incorporation assay (Roche) according to manufacturers information.

Figure 15:
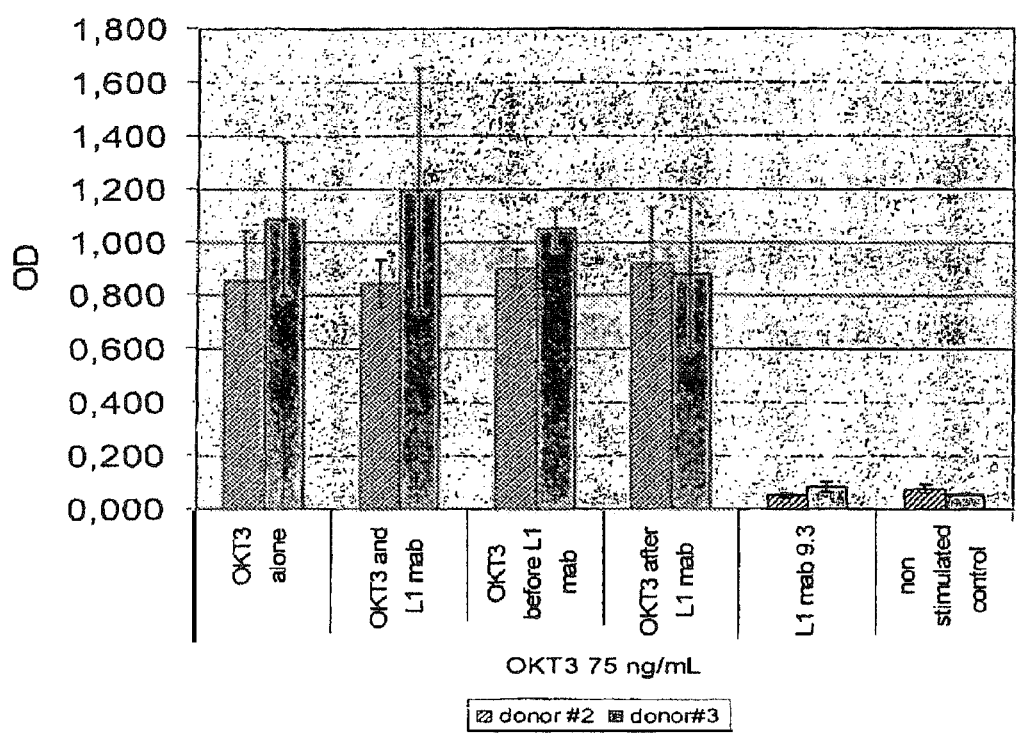

It can be concluded from the results shown in FIG. 15, that L1-9.3 mAb does neither induce T-cell proliferation or inhibit OKT3 induced T-cell proliferation.

10. Example 10

Glycosylation Dependency of Antibody Binding $2 \times 10^6$ SKOV3ip cells were seeded in a 10 cm petri dish and incubated for 24 h at 37° C., 5% $CO_2$. After 24 h, cells were washed with PBS and lysed with 500 µl M-PER reagent (Pierce) according to the protocol described in the Seize Classic Mammalian Immunoprecipitation Kit (Pierce). SkOv3ip cell lysate were deglycosylated as described in the *Enzymatic CarboRelease Kit* (QA_Bio). Briefly, 2.5 µl denaturation solution was added to 35 µl of cell lysate. The sample was incubated in a thermoblock at 100° C. for 5 min and then chilled on ice. Finally 2.5 µl Triton-X and 1 µl of each glycosidase contained in the *Enzymatic CarboRelease Kit* (QA_Bio) (PGNase F, O-Glycosidase, Sialidase, β-Galactosidase, Glucoaminidase) were added according to manufacturers protocol followed by an incubation at 37° C. for 3 h. Glycosylated and deglycosylated were subjected to SDS PAGE and subsequent Western blotting. Western blots were incubated with different L1 antibodies in dependence of their staining performance. Concentrations of 1 µg/ml (9.3, 11A and 14.10), 5 µg/ml (35.9) or 10 µg/ml (OV52.24, OV543.18, 38.12, OV549.20) were used. L1 antibody binding to western blot was detected with HRP-labeled anti-mouse antibody (Dianova).

Figure 16:
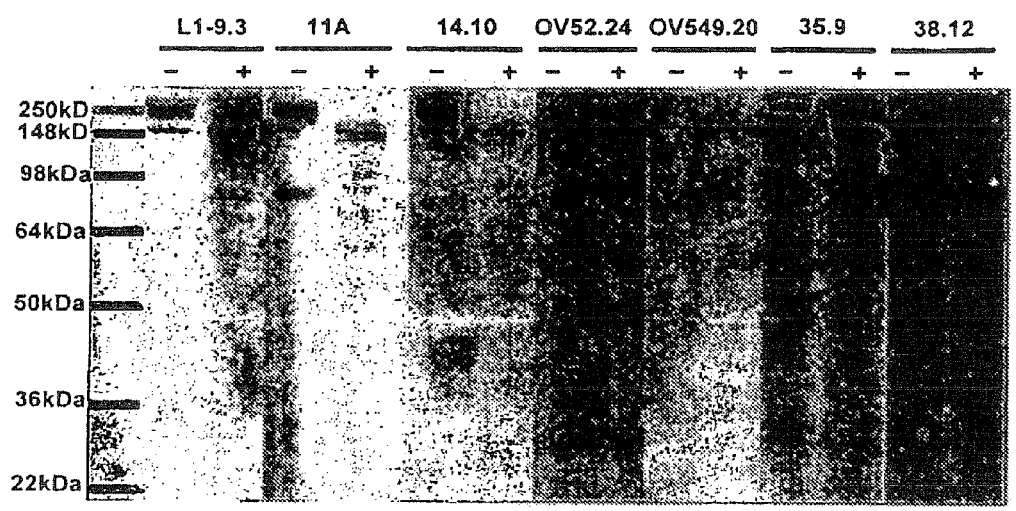

As shown in FIG. 16, the tested anti L1 antibodies can be divided into three classes in respect to their glycosylation-dependency: First class (unaffected by glycosylation): L1-9.3. Second class (binding in WB was negatively affected by deglycosylation): 11A, 14.10, OV52.24 and OV549.20. Third class (binding in WB was positively affected by deglycosylation): 35.9 and 38.12.

11. Example 11

Biodistribution of L1-9.3 in Rabbit

A female rabbit (White Himalayan) was twice injected with L1-9.3 (0 h, 24 h) via the intravenous application route at a dose of 10 mg/kg. 1 control animal received a comparable volume of PBS. Animals were necropsied 72 h after the first application. Organs were fixed in 4% buffered formalin and embedded in paraffin. Histological slides were prepared and immunohistochemistry was performed. Tissue sections of the L1-9.3-treated and control animal were stained with an anti-mouse antibody to detect binding of L1-9.3 after intravenous application. Signals were visualized by DAB (Sigma). Two different detection systems, conventional Avidin/Biotin Complex method or tyramide signal amplification system CSA II method (Dako) were used, which allowed rough estimation of the amount of in vivo bound L1-9.3. The conventional Avidin/Biotin Complex method (Vector Laboratories) is able to detect L1-9.3 concentrations of 50 ng/ml or higher, while the biotin-free tyramide signal amplification system CSA II (Dako) has a detection limit of 5 ng/ml. To determine the L1 expression pattern, tissues of the control animal were incubated with primary antibody L1-9.3 and with the detection antibody. For ABC method a biotinylated anti-mouse antibody (Dianova, dilution 1:3000) was used as detection antibody, for CSA method was performed according to manufacturers protocol.

Figure 17:
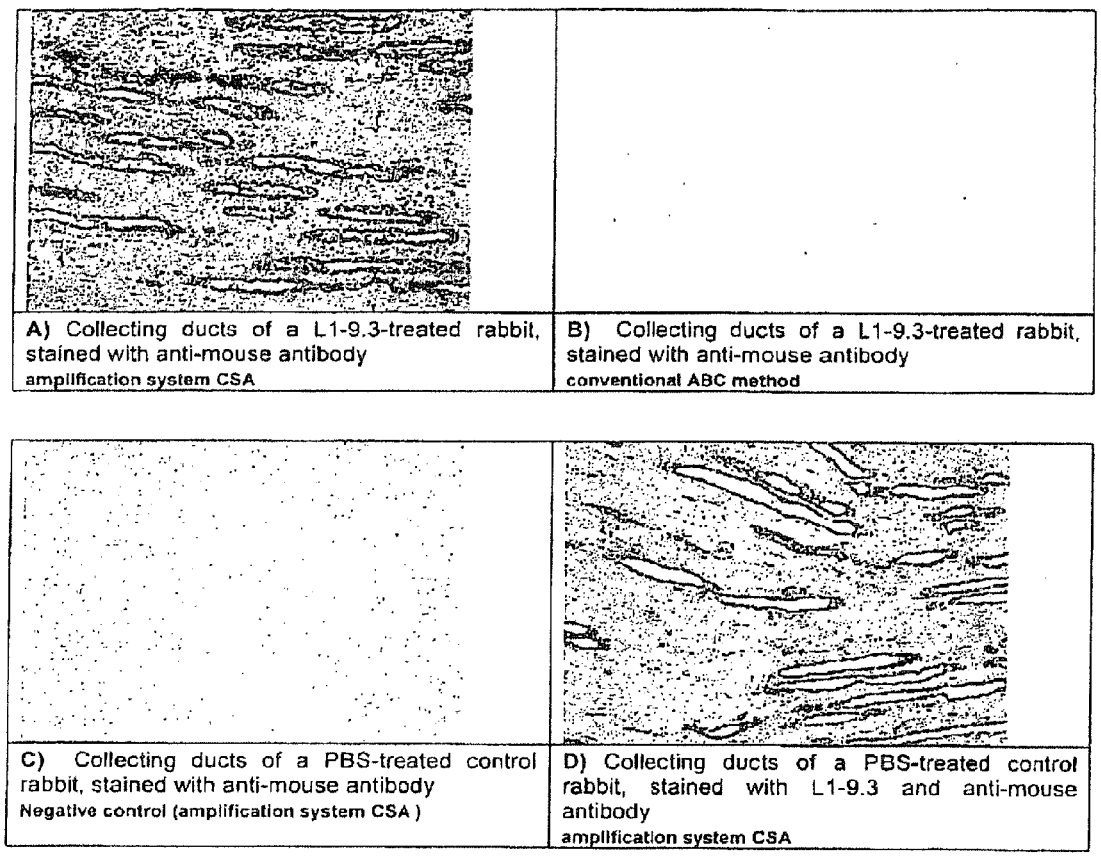

FIG. 17 shows the in vivo binding of intravenously applied L1-9.3 to collecting ducts of the kidney. In vivo binding was only detectable using the amplification system CSA (FIG. 17A), while by using the conventional ABC-method, no signal was visible (FIG. 17B). Hence, L1-9.3 was detected in a range of 30-300 pmol in the tissue (L1-9.3 concentration is presumably higher than 5 ng/ml and below 50 ng/ml). Negative control did not show staining, thus, unspecific staining can be excluded (FIG. 17C). The staining pattern of in vivo bound L1-9.3 (FIG. 17A) corresponds to the L1 expression pattern in the kidney when directly staining tissue sections with L1-9.3 (FIG. 17D). It can be concluded that intravenously administered L1-93 antibody is able to extravasate to peripheral tissue.

12. Example 12

Function of Humanized Forms of L19.3 mAb in Nude Mice

Figure 18:
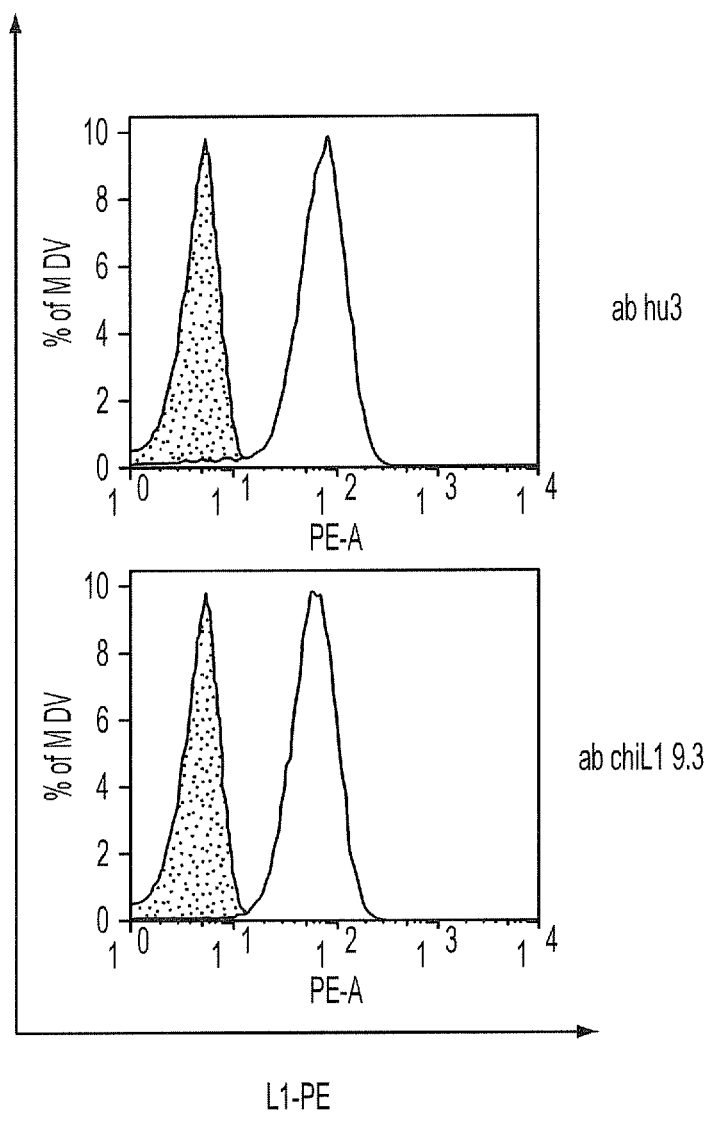

We investigated whether the humanized form of the mAb L19.3 could also inhibit the tumor growth of ovarian carcinoma in vivo. First we analysed the binding of the two humanized forms of L1 9.3 to the selected cell line. Therefore, flow cytometry was performed on SKOV3ip pcDNA3.1 Luciferase cells. (FIG. 18). Both mAbs showed strong binding to the tumor cell line, and gave similar binding results as the native L1 9.3 mAb.

Figure 19:
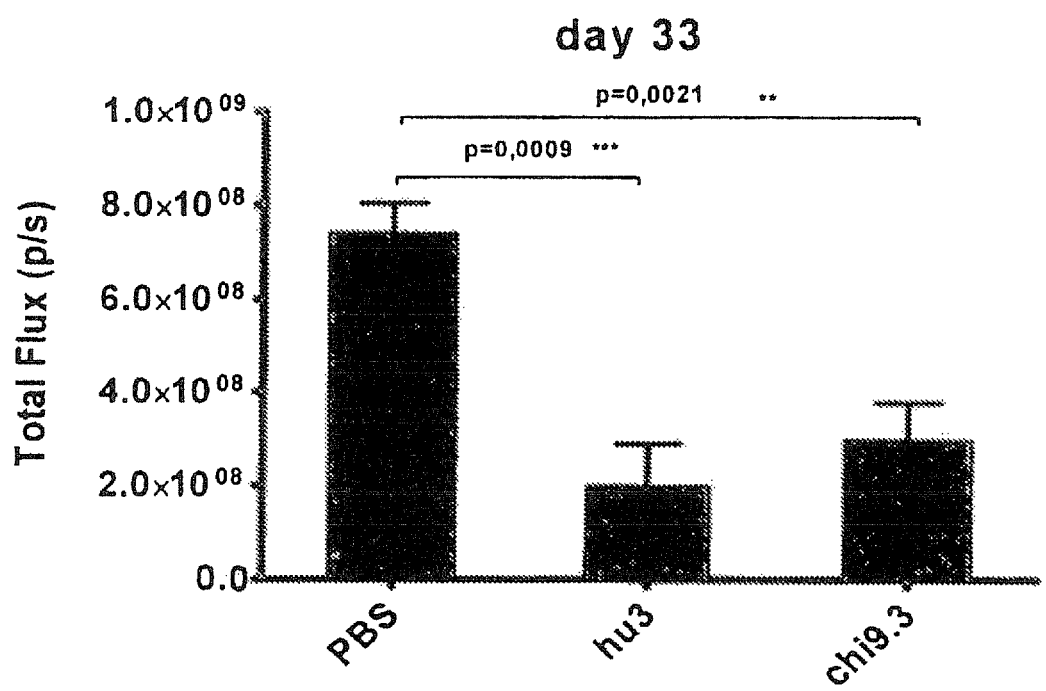
Figure 20:
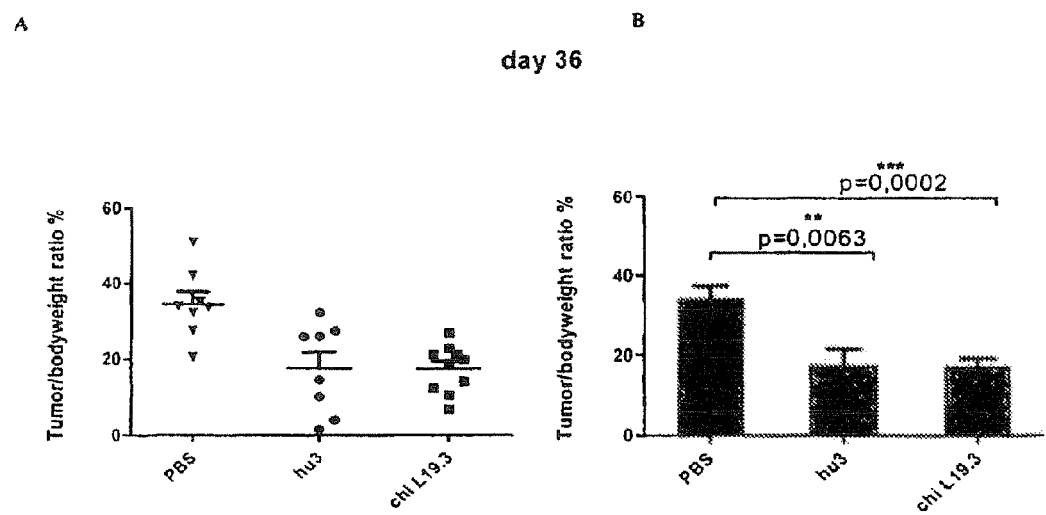

SKOV3ip pcDNA3.1 Luciferase cells were injected into immunodeficient mice 24 h before starting the therapy. Humanized antibodies (300 μg) or PBS were injected three times per week intraperitoneally. To detect the tumor growth in vivo, mice were imaged once weekly using the Xenogen IVIS 200 System. Mice were anesthetised and injected with Luciferin D, followed by detecting the light emission which is produced during luciferase activity of the tumor cells. During the time course we detected a slower tumor growth in the group of mice treated with humanized mAb compared to the control. At day 33 the last imaging data were taken. Imaging results gave a decreased tumor volume of around 80% using the hu3 mAb and approximately of 50% for chiL1 9.3. Both results were strongly significant (FIG. 19). After 36 days mice were sacrificed and tumor mass has determined. In both humanized anti-L1 mAbs treated groups a substantial decreased tumor mass was measured compared to the PBS group (FIG. 20 (A, B)).

13. Example 13

Figure 21:
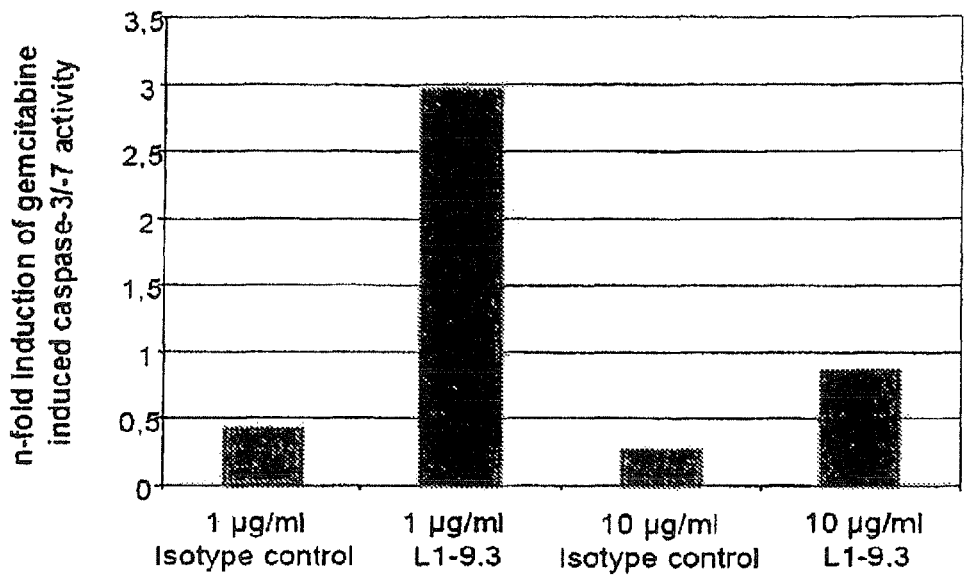
Figure 21:
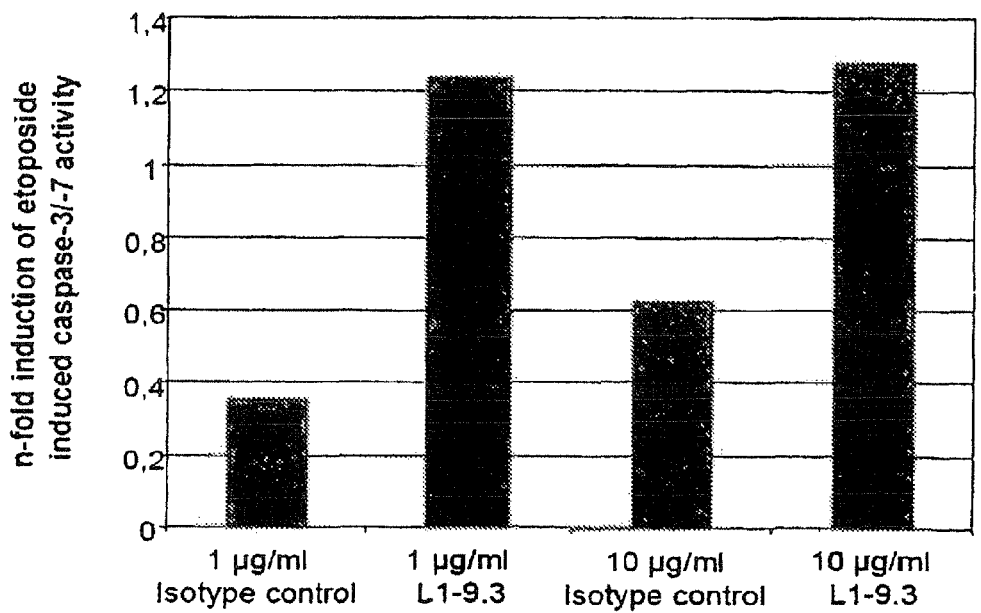
Figure 22:
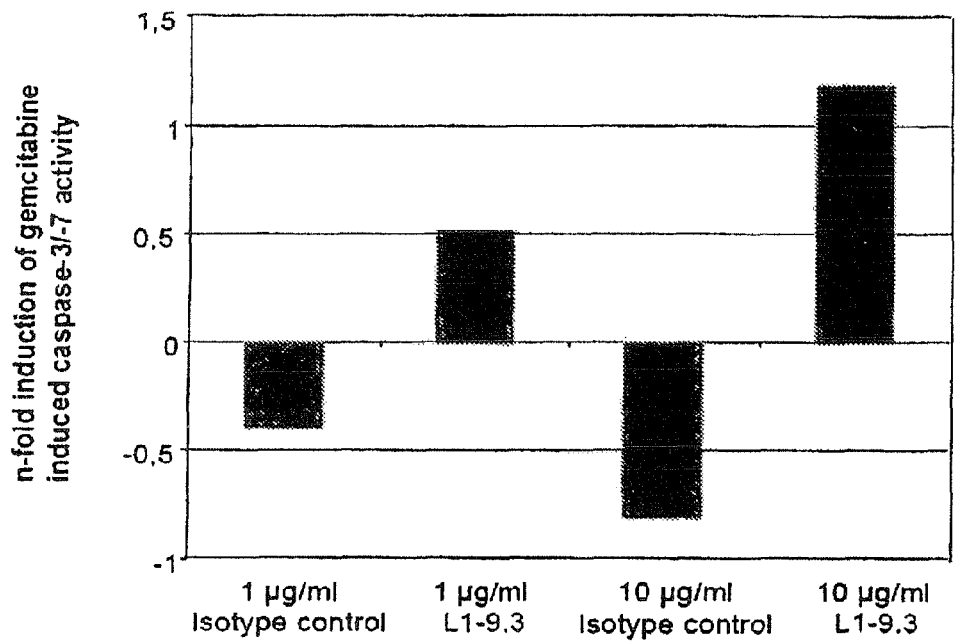
Figure 22:
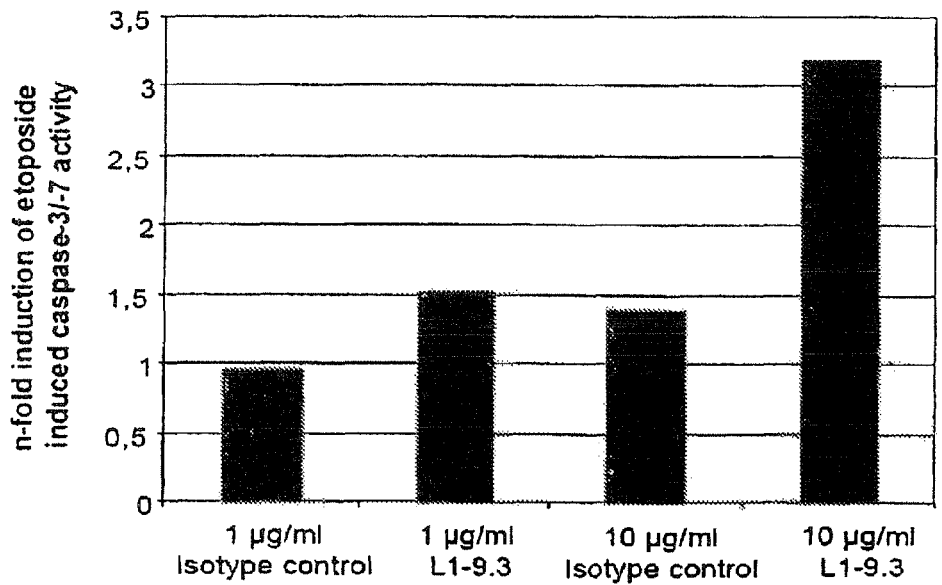

Abolishment of chemoresistance by treatment with anti L1 CAM monoclonal antibody 9.3 was tested as described in WO 2008/046529, Example 3 (see also FIG. 17e of WO 2008/046529). The results are shown in FIGS. 21 and 22. It could be demonstrated that the monoclonal antibody 9.3 abolishes chemoresistance. Its effect seems to be stronger than those of the antibody 11A tested in WO 2008/046529.

TABLE 1

| mAb | FACS | Western blot | IP | L1-Fc | Invasion | phospho-Erk | ka (1/Ms) | kd (1/s) | KD (M) | tumor growth |
|---|---|---|---|---|---|---|---|---|---|---|
| L1-9.3 | +++ | +++ | +++ | +++ | −60% | −50% | 2.6E+05 | 2.2E−05 | 8.5E−11 | −60% |
| L1-11A | +++ | +++ | +++ | +++ | −50% | −40% | 1.0E+05 | 4.0E−06 | 4.0E−11 | −40% |
| L1-14.10 | + | ++ | + | +++ | −40% | −40% | 1.4E+04 | 1.0E−06 | 7.1E−11 | −30% |
| L1-38.12 | + | +++ | + | +++ | 0 | 0 | 3.7E+04 | 2.0E−06 | 5.4E−11 | |
| L1-35.9 | + | +++ | + | +++ | 0 | 0 | 4.0E+04 | 1.2E−05 | 3.0E−10 | |
| L1-N15.17 | ++ | − | ++ | ++ | 0 | 0 | 5.3E+04 | 1.0E−03 | 1.9E−08 | |
| L1-1D12.22 | − | − | + | ++ | 0 | −20% | 2.3E+04 | 1.0E−04 | 4.3E−09 | |
| L1-1D17.3 | − | − | + | ++ | 0 | 0 | 2.3E+04 | 1.0E−04 | 4.3E−09 | |
| L1-1D64.8 | − | +++ | + | +++ | 0 | 0 | 8.5E+04 | 1.5E−04 | 1.8E−09 | |
| L1-1D74.8 | − | +++ | + | +++ | −10% | 0 | 3.0E+04 | 2.0E−03 | 6.7E−08 | |

The invention claimed is:

1. A purified binding molecule capable of binding L1CAM
   (i) comprising the following six CDR sequences RASQDISNYLN (SEQ ID No: 1), YTSRLHS (SEQ ID No: 2), QQGNTLPWT (SEQ ID No: 3), RYWML (SEQ ID No: 4), EINPRNDRTNYNEKFKT (SEQ ID No: 5), and GGGYAMDY (SEQ ID No: 6), or
   (ii) which is capable of binding to the same L1CAM epitope recognized by the monoclonal antibody 9.3, produced by the hybridoma cell deposited under DSMZ ACC2841, or
   (iii) comprising the following six CDR sequences QDISNY (SEQ ID No: 7), YTS, QQGNTLPWT (SEQ ID No: 8), GYTFTRYW (SEQ ID No: 9), INPRNDRT (SEQ ID No: 10), and ALGGGYAMDY (SEQ ID No: 11),
      wherein the purified binding molecule capable of binding L1CAM is selected from the group consisting of single chain antibody (scFv), a multimer of scFv, a diabody, a triabody, a tetrabody, an antigen-binding fragment of a monoclonal antibody, a Fab, a tandab, a flexibody, a bispecific antibody, and a chimeric antibody.

2. The purified binding molecule capable of binding L1CAM of claim 1, wherein the binding molecule binds L1CAM with an affinity (KD) of at least $10^{-8}$ M, $10^{-9}$ M, $10^{-10}$ M, or $10^{-11}$ M.

3. The purified binding molecule capable of binding L1CAM of claim 1, linked to an active substance.

4. The purified binding molecule capable of binding L1CAM of claim 3, wherein the active substance is a toxin, a cytokine, a nanoparticle or a radionuclide.

5. The purified binding molecule capable of binding L1CAM of claim 1, wherein the epitope is within the first immunoglobulin-like domain of L1CAM.

6. A method for treating a tumor disease, wherein a binding molecule capable of binding L1CAM of claim 1 is administered to a subject in an effective amount to treat said disease.

7. The method of claim 6 for sensitizing tumor cells in a patient for the treatment with a chemotherapeutic drug or with radiotherapy.

8. The method of claim 6 for sensitizing tumor cells in a patient for the treatment with a chemotherapeutic drug or with radiotherapy, wherein the cells are at least partially resistant to the treatment with said chemotherapeutic drug or to radiotherapy.

9. The method of claim 6 for sensitizing tumor cells in a patient for the treatment with a chemotherapeutic drug or with radiotherapy, wherein after the sensitization with the binding molecule the patient is further treated with said chemotherapeutic drug or with radiotherapy.

10. The method of claim 6 for the treatment of a tumor disease in a patient previously treated with a chemotherapeutic drug or with radiotherapy.

11. The method of claim 10 for the treatment of a tumorigenic disease in a patient at least partially resistant to the treatment with said chemotherapeutic drug or with radiotherapy.

12. The method of claim 6, wherein the binding molecule is administered in combination with a chemotherapeutic drug or with radiotherapy.

13. The method of claim 6, wherein the binding molecule is administered in combination with a chemotherapeutic drug or with radiotherapy, wherein the chemotherapeutic drug or the radiotherapy is administered prior to the binding molecule.

14. The method of claim 6, wherein the tumor disease is selected from the group consisting of astrocytoma, oligodendroglioma, meningioma, neurofibroma, glioblastoma, ependymoma, Schwannoma, neurofibrosarcoma, medulloblastoma, melanoma, pancreatic cancer, prostate carcinoma, head and neck cancer, breast cancer, lung cancer, ovarian cancer, endometrial cancer, renal cancer, neuroblastomas, squamous carcinomas, hepatoma, colon cancer and mesothelioma and epidermoid carcinoma.

15. The method of claim 6, wherein the tumor disease bears the tumor cells from an epithelial tumor or the tumor disease is an epithelial tumor.

16. The method of claim 15, wherein the epithelial tumor is pancreatic cancer, colon cancer, ovarian cancer or endometrial cancer.

17. The method of claim 6 for sensitizing tumor cells in a patient for the treatment with a chemotherapeutic drug or with radiotherapy, wherein the chemotherapeutic drug is a DNA damaging agent.

18. The method of claim 17, wherein the DNA damaging agent is selected from the group consisting of actinomycin-D, mitomycin C, cisplatin, doxorubicin, etoposide, verapamil, podophyllotoxin, 5-FU and taxans, paclitaxel and carboplatin.

19. The method of claim 6 for sensitizing tumor cells in a patient for the treatment with a chemotherapeutic drug or with radiotherapy, wherein the radiotherapy is selected from the group consisting of X-ray radiation, UV-radiation, γ-irradiation, α- or β-irradiation, and microwaves.

20. A pharmaceutical composition, comprising a purified binding molecule capable of binding L1CAM of claim 1.

* * * * *

SEQUENCE LISTING

```
<160> NUMBER OF SEQ ID NOS: 36

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala Ser Gln Asp Ile Ser Asn Tyr Leu Asn
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Thr Ser Arg Leu His Ser
1               5

<210> SEQ ID NO 3
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Gly Asn Thr Leu Pro Trp Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Tyr Trp Met Leu
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Ile Asn Pro Arg Asn Asp Arg Thr Asn Tyr Asn Glu Lys Phe Lys
1               5                   10                  15

Thr

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Tyr Ala Met Asp Tyr
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Asp Ile Ser Asn Tyr
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

```
Gln Gln Gly Asn Thr Leu Pro Trp Thr
1               5
```

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Gly Tyr Thr Phe Thr Arg Tyr Trp
1               5
```

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Ile Asn Pro Arg Asn Asp Arg Thr
1               5
```

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Ala Leu Gly Gly Gly Tyr Ala Met Asp Tyr
1               5                   10
```

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Thr Ser Gly Pro Gly Asp Gly Gly Lys Gly Pro Gly Lys Gly Pro
1               5                   10                  15

Gly Gly Glu Gly Thr Lys Gly Thr Gly Pro Gly Gly
            20                  25
```

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agccggccat ggccgatatt cagatgaccc agac                            34

<210> SEQ ID NO 14
<211> LENGTH: 41

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tctatgcagc ggcggcaccg ccgctgctca cggtaacgct g                     41

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agccggccat ggccgatatt cagatgaccc agag                              34

<210> SEQ ID NO 16
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tctatgcagc ggccgcaccg ccgctgctca cggtaaccag ggtg                   44

<210> SEQ ID NO 17
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Met Thr Gln Thr Thr Ser Ser Leu Ser Ala Phe Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys Arg
            100                 105

<210> SEQ ID NO 18
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Asp Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Ser Leu Glu Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Asn Ser Leu
            85                  90                  95

Pro Tyr Thr Phe Gly Gln Gly Thr Lys Val Glu Ile Lys
        100                 105
```

<210> SEQ ID NO 19
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ile Lys Tyr
            20                  25                  30

Leu Asn Trp Tyr Gln Gln Thr Pro Gly Lys Ala Pro Lys Leu Leu Ile
        35                  40                  45

Tyr Glu Ala Ser Asn Leu Gln Ala Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Gln Ser Leu Pro Tyr
            85                  90                  95

Thr Phe Gly Gln Gly Thr Lys Leu Gln Ile Thr Arg
        100                 105
```

<210> SEQ ID NO 20
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80
```

```
Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys Arg
            100                 105

<210> SEQ ID NO 21
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys Arg
            100                 105

<210> SEQ ID NO 22
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Gln Pro Gly Ala Glu Leu Val Lys Ser Gly Ala
1               5                   10                  15

Ser Val Asn Leu Ser Cys Arg Ala Ser Gly Tyr Thr Phe Thr Arg Tyr
            20                  25                  30

Trp Met Leu Trp Val Arg Gln Arg Pro Gly His Gly Leu Glu Trp Val
        35                  40                  45

Gly Glu Ile Asn Pro Arg Asn Asp Arg Thr Asn Tyr Asn Glu Lys Phe
    50                  55                  60

Lys Thr Lys Ala Thr Leu Thr Val Asp Arg Ser Ser Ser Thr Ala Tyr
65                  70                  75                  80

Met Gln Leu Thr Ser Leu Thr Ser Glu Asp Ser Ala Val Tyr Phe Cys
                85                  90                  95

Ala Leu Gly Gly Gly Tyr Ala Met Asp Tyr Trp Gly Gln Gly Thr Ser
            100                 105                 110

Val Thr Val Ser Ser
        115

<210> SEQ ID NO 23
<211> LENGTH: 118
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Lys Asp
            20                  25                  30

Tyr Ala Met Ser Ile Trp Val Arg Gln Ala Pro Gly Lys Gly Leu Glu
        35                  40                  45

Trp Val Ala Val Ile Ser Asn Gly Ser Asp Thr Tyr Tyr Ala Asp Ser
    50                  55                  60

Val Lys Gly Arg Phe Thr Ile Ser Arg Asp Asp Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ser Arg Phe Phe Asp Val Ile Trp Gly Gln Gly Thr
            100                 105                 110

Leu Val Thr Val Ser Ser
        115

<210> SEQ ID NO 24
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 24

Glu Val Gln Leu Val Gln Ser Gly Gly Gly Leu Val Gln Ser Gly Gly
1               5                   10                  15

Ser Leu Arg Leu Ser Cys Arg Ala Ser Gly Tyr Thr Phe Thr Arg Tyr
            20                  25                  30

Trp Met Leu Trp Val Arg Gln Arg Pro Gly His Gly Leu Glu Trp Val
        35                  40                  45

Gly Glu Ile Asn Pro Arg Asn Asp Arg Thr Asn Tyr Asn Glu Lys Phe
    50                  55                  60

Lys Thr Arg Phe Thr Ile Ser Val Asp Arg Ser Lys Ser Thr Ala Tyr
65                  70                  75                  80

Leu Gln Met Asp Ser Leu Arg Ala Glu Asp Thr Ala Val Tyr Phe Cys
                85                  90                  95

Ala Leu Gly Gly Gly Tyr Ala Met Asp Tyr Trp Gly Gln Gly Thr Leu
            100                 105                 110

Val Thr Val Ser Ser
        115

<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 25

Glu Val Gln Leu Val Gln Ser Gly Gly Gly Leu Val Gln Ser Gly Gly
1               5                   10                  15

Ser Leu Arg Leu Ser Cys Arg Ala Ser Gly Tyr Thr Phe Thr Arg Tyr

```
            20                  25                  30
Trp Met Leu Trp Val Arg Gln Arg Pro Gly Lys Gly Leu Glu Trp Val
        35                  40                  45

Ala Glu Ile Asn Pro Arg Asn Asp Arg Thr Asn Tyr Asn Glu Lys Phe
 50                  55                  60

Lys Thr Arg Phe Thr Ile Ser Val Asp Arg Ser Lys Asn Thr Leu Tyr
 65                  70                  75                  80

Leu Gln Met Asp Ser Leu Arg Ala Glu Asp Thr Ala Val Tyr Phe Cys
                85                  90                  95

Ala Leu Gly Gly Gly Tyr Ala Met Asp Tyr Trp Gly Gln Gly Thr Leu
           100                 105                 110

Val Thr Val Ser Ser
           115

<210> SEQ ID NO 26
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Thr Thr Ser Ser Leu Ser Ala Phe Leu Gly
 1                  5                  10                  15

Asp Arg Val Thr Ile Ser Cys Arg Ala Ser Gln Asp Ile Ser Asn Tyr
                 20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
     50                  55                  60

Ser Gly Ser Gly Thr Asp Tyr Ser Leu Thr Ile Ser Asn Leu Glu Gln
 65                  70                  75                  80

Glu Asp Phe Ala Thr Tyr Phe Cys Gln Gln Gly Asn Thr Leu Pro Trp
                 85                  90                  95

Thr Phe Gly Gly Gly Thr Lys Leu Glu Ile Lys Arg Thr Ser Gly Pro
            100                 105                 110

Gly Asp Gly Gly Lys Gly Gly Pro Gly Lys Gly Pro Gly Gly Glu Gly
        115                 120                 125

Thr Lys Gly Thr Gly Pro Gly Gly Gln Val Gln Leu Gln Gln Pro Gly
130                 135                 140

Ala Glu Leu Val Lys Ser Gly Ala Ser Val Asn Leu Ser Cys Arg Ala
145                 150                 155                 160

Ser Gly Tyr Thr Phe Thr Arg Tyr Trp Met Leu Trp Val Arg Gln Arg
                165                 170                 175

Pro Gly His Gly Leu Glu Trp Val Gly Glu Ile Asn Pro Arg Asn Asp
            180                 185                 190

Arg Thr Asn Tyr Asn Glu Lys Phe Lys Thr Lys Ala Thr Leu Thr Val
        195                 200                 205

Asp Arg Ser Ser Ser Thr Ala Tyr Met Gln Leu Thr Ser Leu Thr Ser
    210                 215                 220

Glu Asp Ser Ala Val Tyr Phe Cys Ala Leu Gly Gly Gly Tyr Ala Met
225                 230                 235                 240

Asp Tyr Trp Gly Gln Gly Thr Ser Val Thr Val Ser Ser
                245                 250
```

<210> SEQ ID NO 27
<211> LENGTH: 253
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys Arg Thr Ser Gly Pro
            100                 105                 110

Gly Asp Gly Gly Lys Gly Gly Pro Gly Lys Pro Gly Gly Glu Gly
            115                 120                 125

Thr Lys Gly Thr Gly Pro Gly Gly Glu Val Gln Leu Val Gln Ser Gly
130                 135                 140

Gly Gly Leu Val Gln Ser Gly Gly Ser Leu Arg Leu Ser Cys Arg Ala
145                 150                 155                 160

Ser Gly Tyr Thr Phe Thr Arg Tyr Trp Met Leu Trp Val Arg Gln Arg
                165                 170                 175

Pro Gly His Gly Leu Glu Trp Val Gly Glu Ile Asn Pro Arg Asn Asp
            180                 185                 190

Arg Thr Asn Tyr Asn Glu Lys Phe Lys Thr Arg Phe Thr Ile Ser Val
        195                 200                 205

Asp Arg Ser Lys Ser Thr Ala Tyr Leu Gln Met Asp Ser Leu Arg Ala
    210                 215                 220

Glu Asp Thr Ala Val Tyr Phe Cys Ala Leu Gly Gly Gly Tyr Ala Met
225                 230                 235                 240

Asp Tyr Trp Gly Gln Gly Thr Leu Val Thr Val Ser Ser
                245                 250
```

<210> SEQ ID NO 28
<211> LENGTH: 253
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

```
Tyr Tyr Thr Ser Arg Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Phe Cys Gln Gln Gly Asn Thr Leu Pro Trp
                 85                  90                  95

Thr Phe Gly Gly Gly Thr Lys Leu Glu Ile Lys Arg Thr Ser Gly Pro
            100                 105                 110

Gly Asp Gly Gly Lys Gly Gly Pro Gly Lys Gly Pro Gly Gly Glu Gly
        115                 120                 125

Thr Lys Gly Thr Gly Pro Gly Gly Glu Val Gln Leu Val Gln Ser Gly
130                 135                 140

Gly Gly Leu Val Gln Ser Gly Gly Ser Leu Arg Leu Ser Cys Arg Ala
145                 150                 155                 160

Ser Gly Tyr Thr Phe Thr Arg Tyr Trp Met Leu Trp Val Arg Gln Arg
                165                 170                 175

Pro Gly Lys Gly Leu Glu Trp Val Ala Glu Ile Asn Pro Arg Asn Asp
            180                 185                 190

Arg Thr Asn Tyr Asn Glu Lys Phe Lys Thr Arg Phe Thr Ile Ser Val
        195                 200                 205

Asp Arg Ser Lys Asn Thr Leu Tyr Leu Gln Met Asp Ser Leu Arg Ala
210                 215                 220

Glu Asp Thr Ala Val Tyr Phe Cys Ala Leu Gly Gly Tyr Ala Met Asp
225                 230                 235                 240

Tyr Trp Gly Gln Gly Thr Leu Val Thr Val Ser Ser
                245                 250

<210> SEQ ID NO 29
<211> LENGTH: 1178
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (5)..(1171)

<400> SEQUENCE: 29 acat atg aaa tac cta ttg cct acg gca gcc gct gga ttg tta tta ctc       49
     Met Lys Tyr Leu Leu Pro Thr Ala Ala Ala Gly Leu Leu Leu Leu
      1               5                  10                  15 gcg gcc cag ccg gcc atg gcc gat att cag atg acc cag acc acg agc       97
Ala Ala Gln Pro Ala Met Ala Asp Ile Gln Met Thr Gln Thr Thr Ser
             20                  25                  30 agc ctg agc gcg ttt ctg ggc gat cgt gtg acc att agc tgc cgt gcg      145
Ser Leu Ser Ala Phe Leu Gly Asp Arg Val Thr Ile Ser Cys Arg Ala
         35                  40                  45 agc cag gat att agc aac tat ctg aac tgg tat cag cag aaa ccg gat      193
Ser Gln Asp Ile Ser Asn Tyr Leu Asn Trp Tyr Gln Gln Lys Pro Asp
     50                  55                  60 ggc acc gtg aaa ctg ctg att tat tat acc agc cgt ctg cat agc ggt      241
Gly Thr Val Lys Leu Leu Ile Tyr Tyr Thr Ser Arg Leu His Ser Gly
 65                  70                  75 gtg ccg agc cgt ttt agc ggc agc ggt agc ggc acc gat tat agc ctg      289
Val Pro Ser Arg Phe Ser Gly Ser Gly Ser Gly Thr Asp Tyr Ser Leu
 80                  85                  90                  95 acc att tct aac ctg gaa cag gaa gat ttt gcg acc tat ttt tgc cag      337
Thr Ile Ser Asn Leu Glu Gln Glu Asp Phe Ala Thr Tyr Phe Cys Gln
```

```
                  100                 105                 110
cag ggc aac acg ctg ccg tgg acc ttt ggc ggt ggc acc aaa ctg gaa      385
Gln Gly Asn Thr Leu Pro Trp Thr Phe Gly Gly Gly Thr Lys Leu Glu
            115                 120                 125 att aaa cgt act agt ggt ccg ggc gat ggc ggt aaa ggc ggt ccg ggc      433
Ile Lys Arg Thr Ser Gly Pro Gly Asp Gly Gly Lys Gly Gly Pro Gly
        130                 135                 140 aaa ggt ccg ggt ggc gaa ggc acc aaa ggc act ggg ccc ggg ggt cag      481
Lys Gly Pro Gly Gly Glu Gly Thr Lys Gly Thr Gly Pro Gly Gly Gln
145                 150                 155 gtt cag ctg cag cag ccg ggt gcg gaa ctg gtg aaa agc ggc gcg agc      529
Val Gln Leu Gln Gln Pro Gly Ala Glu Leu Val Lys Ser Gly Ala Ser
160                 165                 170                 175 gtg aac ctg agc tgt cgt gcg agc ggc tat acc ttt acc cgt tat tgg      577
Val Asn Leu Ser Cys Arg Ala Ser Gly Tyr Thr Phe Thr Arg Tyr Trp
                180                 185                 190 atg ctg tgg gtg cgt cag cgt ccg ggc cac ggc ctg gaa tgg gtg ggc      625
Met Leu Trp Val Arg Gln Arg Pro Gly His Gly Leu Glu Trp Val Gly
            195                 200                 205 gaa att aat ccg cgt aac gat cgt acc aac tat aac gaa aaa ttc aaa      673
Glu Ile Asn Pro Arg Asn Asp Arg Thr Asn Tyr Asn Glu Lys Phe Lys
        210                 215                 220 acc aaa gcg acc ctg acc gtg gat cgt agc agc agc acc gcg tat atg      721
Thr Lys Ala Thr Leu Thr Val Asp Arg Ser Ser Ser Thr Ala Tyr Met
225                 230                 235 cag ctg acg agc ctg acc tct gaa gat agc gcg gtg tat ttc tgc gcg      769
Gln Leu Thr Ser Leu Thr Ser Glu Asp Ser Ala Val Tyr Phe Cys Ala
240                 245                 250                 255 ctg ggc ggt ggc tat gcg atg gat tat tgg ggc cag ggc acc agc gtt      817
Leu Gly Gly Gly Tyr Ala Met Asp Tyr Trp Gly Gln Gly Thr Ser Val
                260                 265                 270 acc gtg agc agc ggc ggt gcg gcc gct gca cca tct gtc ttc atc ttc      865
Thr Val Ser Ser Gly Gly Ala Ala Ala Ala Pro Ser Val Phe Ile Phe
            275                 280                 285 ccg cca tct gat gag cag ttg aaa tct gga act gcc tct gtt gtg tgc      913
Pro Pro Ser Asp Glu Gln Leu Lys Ser Gly Thr Ala Ser Val Val Cys
        290                 295                 300 ctg ctg aat aac ttc tat ccc aga gag gcc aaa gta cag tgg aag gtg      961
Leu Leu Asn Asn Phe Tyr Pro Arg Glu Ala Lys Val Gln Trp Lys Val
305                 310                 315 gat aac gcc ctc caa tcg ggt aac tcc cag gag agt gtc aca gag cag      1009
Asp Asn Ala Leu Gln Ser Gly Asn Ser Gln Glu Ser Val Thr Glu Gln
320                 325                 330                 335 gac agc aag gac agc acc tac agc ctc agc agc acc ctg acg ctg agc      1057
Asp Ser Lys Asp Ser Thr Tyr Ser Leu Ser Ser Thr Leu Thr Leu Ser
                340                 345                 350 aaa gca gac tac gag aaa cac aaa gtc tac gcc tgc gaa gtc acc cat      1105
Lys Ala Asp Tyr Glu Lys His Lys Val Tyr Ala Cys Glu Val Thr His
            355                 360                 365 cag ggc ctg agt tcg ccc gtc aca aag agc ttc aac cgc gga gag tca      1153
Gln Gly Leu Ser Ser Pro Val Thr Lys Ser Phe Asn Arg Gly Glu Ser
        370                 375                 380 cac cac cac cac cac cac tagtaat                                      1178
His His His His His His
    385

<210> SEQ ID NO 30
<211> LENGTH: 389
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 30

```
Met Lys Tyr Leu Leu Pro Thr Ala Ala Ala Gly Leu Leu Leu Leu Ala
1               5                   10                  15

Ala Gln Pro Ala Met Ala Asp Ile Gln Met Thr Gln Thr Thr Ser Ser
            20                  25                  30

Leu Ser Ala Phe Leu Gly Asp Arg Val Thr Ile Ser Cys Arg Ala Ser
        35                  40                  45

Gln Asp Ile Ser Asn Tyr Leu Asn Trp Tyr Gln Gln Lys Pro Asp Gly
50                  55                  60

Thr Val Lys Leu Leu Ile Tyr Tyr Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Phe Ala Thr Tyr Phe Cys Gln Gln
            100                 105                 110

Gly Asn Thr Leu Pro Trp Thr Phe Gly Gly Gly Thr Lys Leu Glu Ile
        115                 120                 125

Lys Arg Thr Ser Gly Pro Gly Asp Gly Gly Lys Gly Gly Pro Gly Lys
130                 135                 140

Gly Pro Gly Gly Glu Gly Thr Lys Gly Thr Gly Pro Gly Gly Gln Val
145                 150                 155                 160

Gln Leu Gln Gln Pro Gly Ala Glu Leu Val Lys Ser Gly Ala Ser Val
            165                 170                 175

Asn Leu Ser Cys Arg Ala Ser Gly Tyr Thr Phe Thr Arg Tyr Trp Met
        180                 185                 190

Leu Trp Val Arg Gln Arg Pro Gly His Gly Leu Glu Trp Val Gly Glu
    195                 200                 205

Ile Asn Pro Arg Asn Asp Arg Thr Asn Tyr Asn Glu Lys Phe Lys Thr
210                 215                 220

Lys Ala Thr Leu Thr Val Asp Arg Ser Ser Thr Ala Tyr Met Gln
225                 230                 235                 240

Leu Thr Ser Leu Thr Ser Glu Asp Ser Ala Val Tyr Phe Cys Ala Leu
            245                 250                 255

Gly Gly Gly Tyr Ala Met Asp Tyr Trp Gly Gln Gly Thr Ser Val Thr
        260                 265                 270

Val Ser Ser Gly Gly Ala Ala Ala Pro Ser Val Phe Ile Phe Pro
    275                 280                 285

Pro Ser Asp Glu Gln Leu Lys Ser Gly Thr Ala Ser Val Val Cys Leu
290                 295                 300

Leu Asn Asn Phe Tyr Pro Arg Glu Ala Lys Val Gln Trp Lys Val Asp
305                 310                 315                 320

Asn Ala Leu Gln Ser Gly Asn Ser Gln Glu Ser Val Thr Glu Gln Asp
            325                 330                 335

Ser Lys Asp Ser Thr Tyr Ser Leu Ser Ser Thr Leu Thr Leu Ser Lys
        340                 345                 350

Ala Asp Tyr Glu Lys His Lys Val Tyr Ala Cys Glu Val Thr His Gln
    355                 360                 365

Gly Leu Ser Ser Pro Val Thr Lys Ser Phe Asn Arg Gly Glu Ser His
370                 375                 380

His His His His
```

<210> SEQ ID NO 31
<211> LENGTH: 1179
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (5)..(1171)

<400> SEQUENCE: 31

```
acat atg aaa tac cta ttg cct acg gca gcc gct gga ttg tta tta ctc        49
     Met Lys Tyr Leu Leu Pro Thr Ala Ala Ala Gly Leu Leu Leu Leu
     1               5                   10                  15 gcg gcc cag ccg gcc atg gcc gat att cag atg acc cag agc ccg agc        97
Ala Ala Gln Pro Ala Met Ala Asp Ile Gln Met Thr Gln Ser Pro Ser
                 20                  25                  30 agc ctg agc gcg agc gtg ggt gat cgt gtg acc att acc tgc cgt gcg       145
Ser Leu Ser Ala Ser Val Gly Asp Arg Val Thr Ile Thr Cys Arg Ala
             35                  40                  45 agc cag gat att agc aac tat ctg aac tgg tat cag cag aaa ccg ggc       193
Ser Gln Asp Ile Ser Asn Tyr Leu Asn Trp Tyr Gln Gln Lys Pro Gly
         50                  55                  60 aaa gcg ccg aaa ctg ctg att tat tat acc agc cgt ctg cat agc ggt       241
Lys Ala Pro Lys Leu Leu Ile Tyr Tyr Thr Ser Arg Leu His Ser Gly
 65                  70                  75                  80 gtg ccg agc cgt ttt agc ggc agc ggt agc ggc acc gat tat acc ttt       289
Val Pro Ser Arg Phe Ser Gly Ser Gly Ser Gly Thr Asp Tyr Thr Phe
                 85                  90                  95 acc att agc agc ctg cag ccg gaa gat ttt gcg acc tat ttt tgc cag       337
Thr Ile Ser Ser Leu Gln Pro Glu Asp Phe Ala Thr Tyr Phe Cys Gln
            100                 105                 110 cag ggc aac acg ctg ccg tgg acc ttt ggc ggt ggc acc aaa ctg gaa       385
Gln Gly Asn Thr Leu Pro Trp Thr Phe Gly Gly Gly Thr Lys Leu Glu
        115                 120                 125 att aaa cgt act agt ggt ccg ggc gat ggc ggt aaa ggc ggt ccg ggc       433
Ile Lys Arg Thr Ser Gly Pro Gly Asp Gly Gly Lys Gly Gly Pro Gly
    130                 135                 140 aaa ggt ccg ggt ggc gaa ggc acc aaa ggc act ggg ccc ggg ggt gaa       481
Lys Gly Pro Gly Gly Glu Gly Thr Lys Gly Thr Gly Pro Gly Gly Glu
145                 150                 155 gtt cag ctg gtg cag agc ggc ggt ggt ctg gtt cag agc ggt ggc agc       529
Val Gln Leu Val Gln Ser Gly Gly Gly Leu Val Gln Ser Gly Gly Ser
160                 165                 170                 175 ctg cgt ctg agc tgt cgt gcg agc ggc tat acc ttc acc cgt tat tgg       577
Leu Arg Leu Ser Cys Arg Ala Ser Gly Tyr Thr Phe Thr Arg Tyr Trp
                180                 185                 190 atg ctg tgg gtg cgt cag cgt ccg ggc cac ggc ctg gaa tgg gtg ggc       625
Met Leu Trp Val Arg Gln Arg Pro Gly His Gly Leu Glu Trp Val Gly
            195                 200                 205 gaa att aat ccg cgt aac gat cgt acc aac tat aac gaa aaa ttt aaa       673
Glu Ile Asn Pro Arg Asn Asp Arg Thr Asn Tyr Asn Glu Lys Phe Lys
        210                 215                 220 acc cgc ttc acc att agc gtg gat cgt agc aaa agc acc gcg tat ctg       721
Thr Arg Phe Thr Ile Ser Val Asp Arg Ser Lys Ser Thr Ala Tyr Leu
    225                 230                 235 cag atg gat agc ctg cgt gcg gaa gat acc gcg gtg tat ttt tgc gcg       769
Gln Met Asp Ser Leu Arg Ala Glu Asp Thr Ala Val Tyr Phe Cys Ala
240                 245                 250                 255
```

```
ctg ggc ggt ggc tat gcg atg gat tat tgg ggc cag ggc acc ctg gtt      817
Leu Gly Gly Gly Tyr Ala Met Asp Tyr Trp Gly Gln Gly Thr Leu Val
                260                 265                 270 acc gtg agc agc ggc ggt gcg gcc gct gca cca tct gtc ttc atc ttc      865
Thr Val Ser Ser Gly Gly Ala Ala Ala Ala Pro Ser Val Phe Ile Phe
            275                 280                 285 ccg cca tct gat gag cag ttg aaa tct gga act gcc tct gtt gtg tgc      913
Pro Pro Ser Asp Glu Gln Leu Lys Ser Gly Thr Ala Ser Val Val Cys
        290                 295                 300 ctg ctg aat aac ttc tat ccc aga gag gcc aaa gta cag tgg aag gtg      961
Leu Leu Asn Asn Phe Tyr Pro Arg Glu Ala Lys Val Gln Trp Lys Val
    305                 310                 315 gat aac gcc ctc caa tcg ggt aac tcc cag gag agt gtc aca gag cag     1009
Asp Asn Ala Leu Gln Ser Gly Asn Ser Gln Glu Ser Val Thr Glu Gln
320                 325                 330                 335 gac agc aag gac agc acc tac agc ctc agc agc acc ctg acg ctg agc     1057
Asp Ser Lys Asp Ser Thr Tyr Ser Leu Ser Ser Thr Leu Thr Leu Ser
                340                 345                 350 aaa gca gac tac gag aaa cac aaa gtc tac gcc tgc gaa gtc acc cat     1105
Lys Ala Asp Tyr Glu Lys His Lys Val Tyr Ala Cys Glu Val Thr His
            355                 360                 365 cag ggc ctg agt tcg ccc gtc aca aag agc ttc aac cgc gga gag tca     1153
Gln Gly Leu Ser Ser Pro Val Thr Lys Ser Phe Asn Arg Gly Glu Ser
        370                 375                 380 cac cac cac cac cac cac tagtaatt                                     1179
His His His His His His
    385

<210> SEQ ID NO 32
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Lys Tyr Leu Leu Pro Thr Ala Ala Ala Gly Leu Leu Leu Leu Ala
1               5                   10                  15

Ala Gln Pro Ala Met Ala Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Ser Asn Tyr Leu Asn Trp Tyr Gln Gln Lys Pro Gly Lys
    50                  55                  60

Ala Pro Lys Leu Leu Ile Tyr Tyr Thr Ser Arg Leu His Ser Gly Val
65                  70                  75                  80

Pro Ser Arg Phe Ser Gly Ser Gly Ser Gly Thr Asp Tyr Thr Phe Thr
                85                  90                  95

Ile Ser Ser Leu Gln Pro Glu Asp Phe Ala Thr Tyr Phe Cys Gln Gln
            100                 105                 110

Gly Asn Thr Leu Pro Trp Thr Phe Gly Gly Gly Thr Lys Leu Glu Ile
        115                 120                 125

Lys Arg Thr Ser Gly Pro Gly Asp Gly Lys Gly Gly Pro Gly Lys
    130                 135                 140

Gly Pro Gly Gly Glu Gly Thr Lys Gly Thr Gly Pro Gly Gly Glu Val
145                 150                 155                 160

Gln Leu Val Gln Ser Gly Gly Gly Leu Val Gln Ser Gly Gly Ser Leu
```

```
                    165                 170                 175
Arg Leu Ser Cys Arg Ala Ser Gly Tyr Thr Phe Thr Arg Tyr Trp Met
                180                 185                 190

Leu Trp Val Arg Gln Arg Pro Gly His Gly Leu Glu Trp Val Gly Glu
            195                 200                 205

Ile Asn Pro Arg Asn Asp Arg Thr Asn Tyr Asn Glu Lys Phe Lys Thr
        210                 215                 220

Arg Phe Thr Ile Ser Val Asp Arg Ser Lys Ser Thr Ala Tyr Leu Gln
225                 230                 235                 240

Met Asp Ser Leu Arg Ala Glu Asp Thr Ala Val Tyr Phe Cys Ala Leu
                245                 250                 255

Gly Gly Gly Tyr Ala Met Asp Tyr Trp Gly Gln Gly Thr Leu Val Thr
            260                 265                 270

Val Ser Ser Gly Gly Ala Ala Ala Ala Pro Ser Val Phe Ile Phe Pro
        275                 280                 285

Pro Ser Asp Glu Gln Leu Lys Ser Gly Thr Ala Ser Val Val Cys Leu
290                 295                 300

Leu Asn Asn Phe Tyr Pro Arg Glu Ala Lys Val Gln Trp Lys Val Asp
305                 310                 315                 320

Asn Ala Leu Gln Ser Gly Asn Ser Gln Glu Ser Val Thr Glu Gln Asp
                325                 330                 335

Ser Lys Asp Ser Thr Tyr Ser Leu Ser Ser Thr Leu Thr Leu Ser Lys
            340                 345                 350

Ala Asp Tyr Glu Lys His Lys Val Tyr Ala Cys Glu Val Thr His Gln
        355                 360                 365

Gly Leu Ser Ser Pro Val Thr Lys Ser Phe Asn Arg Gly Glu Ser His
    370                 375                 380

His His His His
385

<210> SEQ ID NO 33
<211> LENGTH: 1179
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (5)..(1171)

<400> SEQUENCE: 33 acat atg aaa tac cta ttg cct acg gca gcc gct gga ttg tta tta ctc      49
     Met Lys Tyr Leu Leu Pro Thr Ala Ala Ala Gly Leu Leu Leu Leu
     1               5                  10                  15 gcg gcc cag ccg gcc atg gcc gat att cag atg acc cag agc ccg agc      97
Ala Ala Gln Pro Ala Met Ala Asp Ile Gln Met Thr Gln Ser Pro Ser
                20                  25                  30 agc ctg agc gcg agc gtg ggt gat cgt gtg acc att acc tgc cgt gcg     145
Ser Leu Ser Ala Ser Val Gly Asp Arg Val Thr Ile Thr Cys Arg Ala
            35                  40                  45 agc cag gat att agc aac tat ctg aac tgg tat cag cag aaa ccg ggc     193
Ser Gln Asp Ile Ser Asn Tyr Leu Asn Trp Tyr Gln Gln Lys Pro Gly
        50                  55                  60 aaa gcg ccg aaa ctg ctg att tat tat acc agc cgt ctg cat agc ggt     241
Lys Ala Pro Lys Leu Leu Ile Tyr Tyr Thr Ser Arg Leu His Ser Gly
65                  70                  75 gtg ccg agc cgt ttt agc ggc agc ggt agc ggc acc gat tat acc ctg     289
```

|   |   |   |   |   |   |   |   |   |   |   |   |   |   |   |   |   |
|---|---|---|---|---|---|---|---|---|---|---|---|---|---|---|---|---|
| Val | Pro | Ser | Arg | Phe | Ser | Gly | Ser | Gly | Ser | Gly | Thr | Asp | Tyr | Thr | Leu | |
| 80 | | | | 85 | | | | 90 | | | | | | 95 | | |

| acc | att | agc | agc | ctg | cag | ccg | gaa | gat | ttt | gcg | acc | tat | ttt | tgc | cag | 337 |
|---|---|---|---|---|---|---|---|---|---|---|---|---|---|---|---|---|
| Thr | Ile | Ser | Ser | Leu | Gln | Pro | Glu | Asp | Phe | Ala | Thr | Tyr | Phe | Cys | Gln | |
| | | | | 100 | | | | | 105 | | | | | 110 | | |

| cag | ggc | aac | acg | ctg | ccg | tgg | acc | ttt | ggc | ggt | ggc | acc | aaa | ctg | gaa | 385 |
|---|---|---|---|---|---|---|---|---|---|---|---|---|---|---|---|---|
| Gln | Gly | Asn | Thr | Leu | Pro | Trp | Thr | Phe | Gly | Gly | Gly | Thr | Lys | Leu | Glu | |
| | | | 115 | | | | | 120 | | | | | 125 | | | |

| att | aaa | cgt | act | agt | ggt | ccg | ggc | gat | ggc | ggt | aaa | ggc | ggt | ccg | ggc | 433 |
|---|---|---|---|---|---|---|---|---|---|---|---|---|---|---|---|---|
| Ile | Lys | Arg | Thr | Ser | Gly | Pro | Gly | Asp | Gly | Gly | Lys | Gly | Gly | Pro | Gly | |
| | | | 130 | | | | | 135 | | | | | 140 | | | |

| aaa | ggt | ccg | ggt | ggc | gaa | ggc | acc | aaa | ggc | act | ggg | ccc | ggg | ggt | gaa | 481 |
|---|---|---|---|---|---|---|---|---|---|---|---|---|---|---|---|---|
| Lys | Gly | Pro | Gly | Gly | Glu | Gly | Thr | Lys | Gly | Thr | Gly | Pro | Gly | Gly | Glu | |
| | 145 | | | | | 150 | | | | | 155 | | | | | |

| gtt | cag | ctg | gtg | cag | agc | ggc | ggt | ggt | ctg | gtt | cag | agc | ggt | ggc | agc | 529 |
|---|---|---|---|---|---|---|---|---|---|---|---|---|---|---|---|---|
| Val | Gln | Leu | Val | Gln | Ser | Gly | Gly | Gly | Leu | Val | Gln | Ser | Gly | Gly | Ser | |
| 160 | | | | | 165 | | | | | 170 | | | | | 175 | |

| ctg | cgt | ctg | agc | tgt | cgt | gcg | agc | ggc | tat | acc | ttt | acc | cgt | tat | tgg | 577 |
|---|---|---|---|---|---|---|---|---|---|---|---|---|---|---|---|---|
| Leu | Arg | Leu | Ser | Cys | Arg | Ala | Ser | Gly | Tyr | Thr | Phe | Thr | Arg | Tyr | Trp | |
| | | | | 180 | | | | | 185 | | | | | 190 | | |

| atg | ctg | tgg | gtg | cgt | cag | cgt | ccg | ggt | aaa | ggc | ctg | gaa | tgg | gtg | gcg | 625 |
|---|---|---|---|---|---|---|---|---|---|---|---|---|---|---|---|---|
| Met | Leu | Trp | Val | Arg | Gln | Arg | Pro | Gly | Lys | Gly | Leu | Glu | Trp | Val | Ala | |
| | | | 195 | | | | | 200 | | | | | 205 | | | |

| gaa | att | aat | ccg | cgt | aac | gat | cgt | acc | aac | tat | aac | gaa | aaa | ttt | aaa | 673 |
|---|---|---|---|---|---|---|---|---|---|---|---|---|---|---|---|---|
| Glu | Ile | Asn | Pro | Arg | Asn | Asp | Arg | Thr | Asn | Tyr | Asn | Glu | Lys | Phe | Lys | |
| | | | 210 | | | | | 215 | | | | | 220 | | | |

| acc | cgc | ttc | acc | att | agc | gtg | gat | cgt | agc | aaa | aac | acc | ctg | tat | ctg | 721 |
|---|---|---|---|---|---|---|---|---|---|---|---|---|---|---|---|---|
| Thr | Arg | Phe | Thr | Ile | Ser | Val | Asp | Arg | Ser | Lys | Asn | Thr | Leu | Tyr | Leu | |
| | 225 | | | | | 230 | | | | | 235 | | | | | |

| cag | atg | gat | agc | ctg | cgt | gcg | gaa | gat | acc | gcg | gtg | tat | ttt | tgc | gcg | 769 |
|---|---|---|---|---|---|---|---|---|---|---|---|---|---|---|---|---|
| Gln | Met | Asp | Ser | Leu | Arg | Ala | Glu | Asp | Thr | Ala | Val | Tyr | Phe | Cys | Ala | |
| 240 | | | | | 245 | | | | | 250 | | | | | 255 | |

| ctg | ggc | ggt | ggc | tat | gcg | atg | gat | tat | tgg | ggc | cag | ggc | acc | ctg | gtt | 817 |
|---|---|---|---|---|---|---|---|---|---|---|---|---|---|---|---|---|
| Leu | Gly | Gly | Gly | Tyr | Ala | Met | Asp | Tyr | Trp | Gly | Gln | Gly | Thr | Leu | Val | |
| | | | 260 | | | | | 265 | | | | | 270 | | | |

| acc | gtg | agc | agc | ggc | ggt | gcg | gcc | gct | gca | cca | tct | gtc | ttc | atc | ttc | 865 |
|---|---|---|---|---|---|---|---|---|---|---|---|---|---|---|---|---|
| Thr | Val | Ser | Ser | Gly | Gly | Ala | Ala | Ala | Ala | Pro | Ser | Val | Phe | Ile | Phe | |
| | | | 275 | | | | | 280 | | | | | 285 | | | |

| ccg | cca | tct | gat | gag | cag | ttg | aaa | tct | gga | act | gcc | tct | gtt | gtg | tgc | 913 |
|---|---|---|---|---|---|---|---|---|---|---|---|---|---|---|---|---|
| Pro | Pro | Ser | Asp | Glu | Gln | Leu | Lys | Ser | Gly | Thr | Ala | Ser | Val | Val | Cys | |
| | | | 290 | | | | | 295 | | | | | 300 | | | |

| ctg | ctg | aat | aac | ttc | tat | ccc | aga | gag | gcc | aaa | gta | cag | tgg | aag | gtg | 961 |
|---|---|---|---|---|---|---|---|---|---|---|---|---|---|---|---|---|
| Leu | Leu | Asn | Asn | Phe | Tyr | Pro | Arg | Glu | Ala | Lys | Val | Gln | Trp | Lys | Val | |
| | 305 | | | | | 310 | | | | | 315 | | | | | |

| gat | aac | gcc | ctc | caa | tcg | ggt | aac | tcc | cag | gag | agt | gtc | aca | gag | cag | 1009 |
|---|---|---|---|---|---|---|---|---|---|---|---|---|---|---|---|---|
| Asp | Asn | Ala | Leu | Gln | Ser | Gly | Asn | Ser | Gln | Glu | Ser | Val | Thr | Glu | Gln | |
| 320 | | | | | 325 | | | | | 330 | | | | | 335 | |

| gac | agc | aag | gac | agc | acc | tac | agc | ctc | agc | agc | acc | ctg | acg | ctg | agc | 1057 |
|---|---|---|---|---|---|---|---|---|---|---|---|---|---|---|---|---|
| Asp | Ser | Lys | Asp | Ser | Thr | Tyr | Ser | Leu | Ser | Ser | Thr | Leu | Thr | Leu | Ser | |
| | | | 340 | | | | | 345 | | | | | 350 | | | |

| aaa | gca | gac | tac | gag | aaa | cac | aaa | gtc | tac | gcc | tgc | gaa | gtc | acc | cat | 1105 |
|---|---|---|---|---|---|---|---|---|---|---|---|---|---|---|---|---|
| Lys | Ala | Asp | Tyr | Glu | Lys | His | Lys | Val | Tyr | Ala | Cys | Glu | Val | Thr | His | |
| | | | 355 | | | | | 360 | | | | | 365 | | | |

| cag | ggc | ctg | agt | tcg | ccc | gtc | aca | aag | agc | ttc | aac | cgc | gga | gag | tca | 1153 |
|---|---|---|---|---|---|---|---|---|---|---|---|---|---|---|---|---|
| Gln | Gly | Leu | Ser | Ser | Pro | Val | Thr | Lys | Ser | Phe | Asn | Arg | Gly | Glu | Ser | |
| | | 370 | | | | | 375 | | | | | 380 | | | | |

| cac | cac | cac | cac | cac | cac | tagtaatt | 1179 |
|---|---|---|---|---|---|---|---|
| His | His | His | His | His | His | | |
| | | 385 | | | | | |

```
<210> SEQ ID NO 34
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Lys Tyr Leu Leu Pro Thr Ala Ala Gly Leu Leu Leu Leu Ala Ala
1               5                   10                  15

Ala Gln Pro Ala Met Ala Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Ser Asn Tyr Leu Asn Trp Tyr Gln Lys Pro Gly Lys
    50                  55                  60

Ala Pro Lys Leu Leu Ile Tyr Tyr Thr Ser Arg Leu His Ser Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Thr Tyr Phe Cys Gln Gln
            100                 105                 110

Gly Asn Thr Leu Pro Trp Thr Phe Gly Gly Gly Thr Lys Leu Glu Ile
        115                 120                 125

Lys Arg Thr Ser Gly Pro Gly Asp Gly Gly Lys Gly Gly Pro Gly Lys
130                 135                 140

Gly Pro Gly Gly Glu Gly Thr Lys Gly Thr Gly Pro Gly Gly Glu Val
145                 150                 155                 160

Gln Leu Val Gln Ser Gly Gly Gly Leu Val Gln Ser Gly Gly Ser Leu
                165                 170                 175

Arg Leu Ser Cys Arg Ala Ser Gly Tyr Thr Phe Thr Arg Tyr Trp Met
            180                 185                 190

Leu Trp Val Arg Gln Arg Pro Gly Lys Gly Leu Glu Trp Val Ala Glu
        195                 200                 205

Ile Asn Pro Arg Asn Asp Arg Thr Asn Tyr Asn Glu Lys Phe Lys Thr
    210                 215                 220

Arg Phe Thr Ile Ser Val Asp Arg Ser Lys Asn Thr Leu Tyr Leu Gln
225                 230                 235                 240

Met Asp Ser Leu Arg Ala Glu Asp Thr Ala Val Tyr Phe Cys Ala Leu
                245                 250                 255

Gly Gly Gly Tyr Ala Met Asp Tyr Trp Gly Gln Gly Thr Leu Val Thr
            260                 265                 270

Val Ser Ser Gly Gly Ala Ala Ala Pro Ser Val Phe Ile Phe Pro
        275                 280                 285

Pro Ser Asp Glu Gln Leu Lys Ser Gly Thr Ala Ser Val Val Cys Leu
    290                 295                 300

Leu Asn Asn Phe Tyr Pro Arg Glu Ala Lys Val Gln Trp Lys Val Asp
305                 310                 315                 320

Asn Ala Leu Gln Ser Gly Asn Ser Gln Glu Ser Val Thr Glu Gln Asp
                325                 330                 335

Ser Lys Asp Ser Thr Tyr Ser Leu Ser Ser Thr Leu Thr Leu Ser Lys
            340                 345                 350

Ala Asp Tyr Glu Lys His Lys Val Tyr Ala Cys Glu Val Thr His Gln
        355                 360                 365
```

Gly Leu Ser Ser Pro Val Thr Lys Ser Phe Asn Arg Gly Glu Ser His
    370                 375                 380

His His His His His
385

<210> SEQ ID NO 35
<211> LENGTH: 713
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gaagagttag ccttgcagct gtgctcagcc ctaaatagtt cccaaaaatt tgcatgctct      60
cacttcctat ctttgggtac tttttcatat accagtcaga ttgtgagcca ttgtaattga    120
agtcaagact cagcctggac atgatgtcct ctgctcagtt ccttggtctc ctgttgctct    180
gtcttcaagg taaaagttac tacaatggga attttgctgt tgcacagtga ttcttgttga    240
ctggaatttt ggaggggtcc tttcttttcc tgcttaactc tgtgggtatt tattgtgtct    300
ccactcctag gtaccagatg tgatatccag atgacacaga ctacatcctc cctgtctgcc    360
tttctgggag acagagtcac catcagttgc agggcaagtc aggacattag caattattta    420
aactggtatc agcagaaacc agatggaact gttaaactcc ttatctatta cacatcaaga    480
ttacactcag gagtcccctc aaggttcagt ggcagtgggt ctggaacaga ttattctctc    540
accattagca acctggagca agaagatttt gccacttact tttgccaaca gggtaatacg    600
cttccgtgga cattcggtgg aggcaccaag ctggaaatca aacgtaaata gaatccaaag    660
tctctttctt ccgttgtcta tgtctgtggc ttctatgtct acaaatgatg tat           713

<210> SEQ ID NO 36
<211> LENGTH: 839
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
ttcagcatcc tgattcctga cccaggtgtc ccttcttctc cagcaggagt aggtgctcat     60
ctaatatgta tcctgctcat gaatatgcaa atcctctgaa tctacatggt aaatgtaggt    120
ttgtctatat cacacacaga aaacatgag atcacagttc tctctacagt tactgaacac     180
acaggacctc accatgggat ggagctatat catcctcttt ttggtagcaa cagctacagg    240 taagggctc acagtagaag gcttgaggtc tggccatata catgggtgac agtgacatcc    300
actttgcctt tctttccaca gatgtccact cccaggtcca actgcagcag cctggggctg    360
aactggtgaa gtctggggct tcagtgaacc tgtcctgcag ggcttctggc tacaccttca    420
ccagatactg gatgctctgg gtgaggcaga ggcctggaca tggccttgag tgggttggag    480
agattaatcc tcgcaacgat cgtactaatt acaatgagaa attcaagacc aaggccacac    540
tgactgtaga ccgatcctcc agcacagcct acatgcaact caccagcctg acatctgagg    600
actctgcggt ctatttctgt gccctggggg ggggctatgc tatggactat ggggtcaag    660 gaacctcagt caccgtctcc tcaggtaaga atggcctctc caggtcttaa tttttaacct    720

```
ttgttatgga gttttctgag cattgcagac taatcttgga tatttgtccc tgagggagcc    780
ggctgagaga agttgggaaa taaactgtct agggatctca gagcctttag gacagatta     839
```